US009503692B2

(12) United States Patent
Morita et al.

(10) Patent No.: US 9,503,692 B2
(45) Date of Patent: Nov. 22, 2016

(54) IMAGE PROCESSING DEVICE, ELECTRONIC APPARATUS, ENDOSCOPE SYSTEM, INFORMATION STORAGE DEVICE, AND METHOD OF CONTROLLING IMAGE PROCESSING DEVICE

(75) Inventors: Yasunori Morita, Hachiouji (JP); Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1122 days.

(21) Appl. No.: 13/465,155

(22) Filed: May 7, 2012

(65) Prior Publication Data

US 2012/0220840 A1    Aug. 30, 2012

Related U.S. Application Data

(63) Continuation of application No. PCT/JP2010/069944, filed on Nov. 9, 2010.

(30) Foreign Application Priority Data

Nov. 13, 2009  (JP) ................................. 2009-260388

(51) Int. Cl.
*G06K 9/00* (2006.01)
*H04N 7/18* (2006.01)
(Continued)

(52) U.S. Cl.
CPC ............. *H04N 7/18* (2013.01); *A61B 1/00009* (2013.01); *A61B 1/043* (2013.01); *A61B 1/0638* (2013.01);
(Continued)

(58) Field of Classification Search
CPC ................ G06T 7/0012; G06T 7/0081; G06T 7/0083; G06T 7/0079; G06T
(Continued)

(56) References Cited

U.S. PATENT DOCUMENTS 5,512,940 A     4/1996  Takasugi et al.
2002/0016533 A1*  2/2002  Marchitto et al. ............ 600/310
(Continued)

FOREIGN PATENT DOCUMENTS

EP     1 875 855 A1    1/2008
JP     A-06-319695     11/1994
(Continued)

OTHER PUBLICATIONS

International Search Report dated Feb. 22, 2011 issued in PCT/JP2010/069944.
(Continued)

*Primary Examiner* — Elmer Chao
(74) *Attorney, Agent, or Firm* — Scully, Scott, Murphy & Presser, PC

(57) ABSTRACT

The image processing device includes: a first image acquisition section that acquires a first image, the first image being an image that includes an object image including information within a wavelength band of white light; a second image acquisition section that acquires a second image, the second image being an image that includes an object image including information within a specific wavelength band; a candidate attention area detection section that detects a candidate attention area based on a feature quantity of each pixel within the second image, the candidate attention area being a candidate for an attention area; a reliability calculation section that calculates reliability that indicates a likelihood that the candidate attention area is the attention area; and a display mode setting section that performs a display mode setting process that sets a display mode of an output image corresponding to the reliability calculated by the reliability calculation section.

34 Claims, 35 Drawing Sheets

(51) Int. Cl.
*A61B 1/00* (2006.01)
*A61B 1/04* (2006.01)
*A61B 1/06* (2006.01)
*G06T 7/00* (2006.01)
*A61B 5/00* (2006.01)

(52) U.S. Cl.
CPC ........... *A61B 1/0646* (2013.01); *G06T 7/0012* (2013.01); *A61B 5/0084* (2013.01); *G06T 2207/10068* (2013.01); *G06T 2207/10152* (2013.01)

(58) Field of Classification Search
CPC ............. 2207/30101;G06T 2207/30004; G06T 2207/20104; A61B 6/504; A61B 8/0891; A61B 8/5223
See application file for complete search history.

(56) References Cited

U.S. PATENT DOCUMENTS

| | | |
|---|---|---|
| 2006/0252988 A1 | 11/2006 | Ayame et al. |
| 2007/0213593 A1 | 9/2007 | Nakaoka |
| 2008/0039692 A1* | 2/2008 | Hirakawa .......... A61B 1/00045 600/160 |
| 2009/0202124 A1 | 8/2009 | Matsuda et al. |

FOREIGN PATENT DOCUMENTS

| | | |
|---|---|---|
| JP | A-2000-115553 | 4/2000 |
| JP | 2000148987 A * | 5/2000 |
| JP | A-2000-148987 | 5/2000 |
| JP | 2005-157902 A | 6/2005 |
| JP | A-2006-068113 | 3/2006 |
| JP | A-2006-255324 | 9/2006 |
| JP | 2006-304993 A | 11/2006 |
| JP | A-2006-525494 | 11/2006 |
| JP | A-2007-229053 | 9/2007 |
| JP | A-2008-093172 | 4/2008 |
| JP | 2011-104011 A | 6/2011 |
| WO | WO 2004/098398 A2 | 11/2004 |

OTHER PUBLICATIONS

Japanese Office Action dated Jan. 28, 2014 from related Japanese Application No. 2009-260388, together with an English language translation.

Extended Supplementary European Search Report dated Feb. 3, 2015 from related European Application No. 10 82 9932.2.

* cited by examiner

FIG. 4
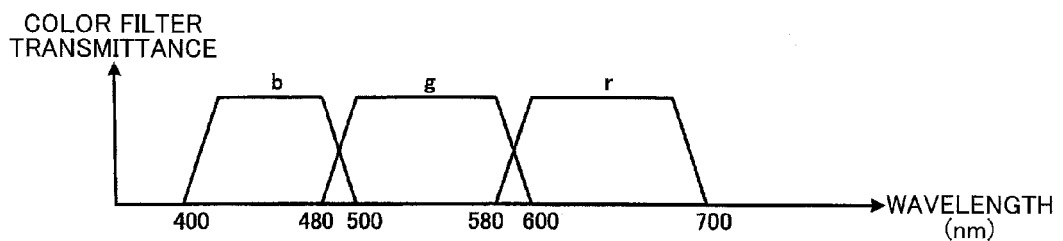
FIG. 5
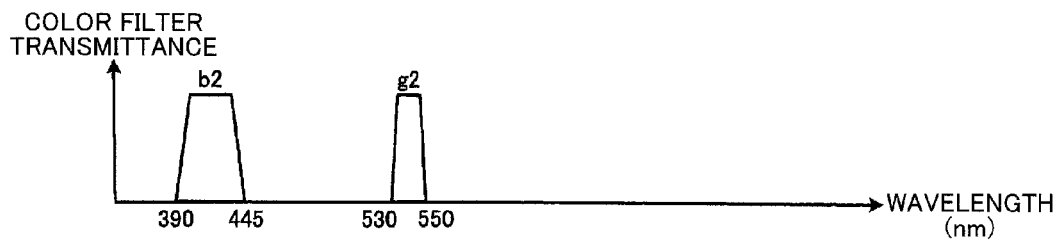
FIG. 6
| g2(0,0) | b2(1,0) | g2(2,0) | b2(3,0) | g2(4,0) | b2(5,0) |
| b2(0,1) | g2(1,1) | b2(2,1) | g2(3,1) | b2(4,1) | g2(5,1) |
| g2(0,2) | b2(1,2) | g2(2,2) | b2(3,2) | g2(4,2) | b2(5,2) |
| b2(0,3) | g2(1,3) | b2(2,3) | g2(3,3) | b2(4,3) | g2(5,3) |

IMAGE PROCESSING DEVICE, ELECTRONIC APPARATUS, ENDOSCOPE SYSTEM, INFORMATION STORAGE DEVICE, AND METHOD OF CONTROLLING IMAGE PROCESSING DEVICE

CROSS REFERENCE TO RELATED APPLICATION

This application is a continuation of International Patent Application No. PCT/JP2010/69944, having an international filing date of Nov. 9, 2010, which designated the United States, the entirety of which is incorporated herein by reference, Japanese Patent Application No. 2009-260388 filed on Nov. 13, 2009 is also incorporated herein by reference in its entirety.

BACKGROUND

The present invention relates to an image processing device, an electronic apparatus, an endoscope system, an information storage device, a method of controlling an image processing device, and the like.

A frame-sequential endoscope system has been widely used. The frame-sequential endoscope system sequentially applies three colors of light (R1, G1, and B1) to tissue inside a body cavity using a rotary filter, and allows diagnosis using an image (normal light image) generated from images of the reflected light. An endoscope system has been proposed that sequentially applies narrow-band light (G2 and B2) that differs in properties from the three colors of light to tissue inside a body cavity, and allows diagnosis using a narrow-band image generated from images of the reflected light (see Patent JP-A-2006-68113, for example). An endoscope system has also been proposed that applies narrow-band excitation light to tissue inside a body cavity, and allows diagnosis using a fluorescent image generated by acquiring intrinsic fluorescence or fluorescence from a fluorescent agent produced from the tissue due to the excitation light (see Patent JP-A-2007-229053, for example).

When using an endoscope system that acquires a narrow-band image (e.g., JP-A-200668113), a lesion area (e.g., epidermoid cancer) that is difficult to observe using normal light is visualized as a brown area differing from a normal area, so that the lesion area can be easily found.

When using an endoscope system that acquires a fluorescent image (e.g., JP-A-2007-229053), only a lesion area (e.g., tumor) produces fluorescence by utilizing a fluorescent agent that is specifically accumulated in such a lesion area, so that the lesion area can be easily found.

SUMMARY

According to one aspect of the invention, there is provided an image processing device comprising:

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

a candidate attention area detection section that detects a candidate attention area based on a feature quantity of each pixel within the second image, the candidate attention area being a candidate for an attention area;

a reliability calculation section that calculates reliability that indicates a likelihood that the candidate attention area detected by the candidate attention area detection section is the attention area; and a display mode setting section that performs a display mode setting process that sets a display mode of an output image corresponding to the reliability calculated by the reliability calculation section.

According to another aspect of the invention, there is provided an electronic apparatus comprising:

the image processing device.

According to another aspect of the invention, there is provided an endoscope system comprising:

a first light source that applies white light to an in vivo object;

a second light source that applies light within a specific wavelength band to an in vivo object;

a first image acquisition section that acquires a first in vivo image, the first in vivo image being an image that is obtained using the first light source and includes an object image including information within a wavelength band of white light;

a second image acquisition section that acquires a second in vivo image, the second in vivo image being an image that is obtained using the second light source and includes an object image including information within the specific wavelength band;

a candidate attention area detection section that detects a candidate attention area based on a feature quantity of each pixel within the second in vivo image, the candidate attention area being a candidate for an attention area;

a reliability calculation section that calculates reliability that indicates a likelihood that the candidate attention area detected by the candidate attention area detection section is the attention area;

a display mode setting section that performs a display mode setting process that sets a display mode of an output image corresponding to the reliability calculated by the reliability calculation section; and a display section that displays the output image according to the display mode set by the display mode setting section.

According to another aspect of the invention, there is provided an image processing device comprising:

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

an attention area detection section that detects an attention area based on a feature quantity of each pixel within the second image; and a display mode setting section that displays an alert area in a corresponding attention area within an output image that corresponds to the attention area, the alert area indicating information about an attention area detection result.

According to another aspect of the invention, there is provided an information storage device storing a program that causes a computer to function as:

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

a candidate attention area detection section that detects a candidate attention area based on a feature quantity of each pixel within the second image, the candidate attention area being a candidate for an attention area;

a reliability calculation section that calculates reliability that indicates a likelihood that the candidate attention area detected by the candidate attention area detection section is the attention area; and a display mode setting section that performs a display mode setting process that sets a display mode of an output image corresponding to the reliability calculated by the reliability calculation section.

According to another aspect of the invention, there is provided an information storage device storing a program that causes a computer to function as:

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

an attention area detection section that detects an attention area based on a feature quantity of each pixel within the second image; and a display mode setting section that displays an alert area in a corresponding attention area within an output image that corresponds to the attention area, the alert area indicating information about an attention area detection result.

According to another aspect of the invention, there is provided a method of controlling an image processing device, the method comprising:

acquiring a first image, the first image being a color image that includes a plurality of channels, and includes an object image including information within a wavelength band of white light;

acquiring a second image, the second image being an image that includes an object image including information within a specific wavelength band, and differs from the plurality of channels included in the first image;

detecting a candidate attention area based on a feature quantity of each pixel within the second image, the candidate attention area being a candidate for an attention area;

calculating reliability that indicates a likelihood that the candidate attention area is the attention area; and performing a display mode setting process that sets a display mode of an output image corresponding to the reliability.

According to another aspect of the invention, there is provided a method of controlling an image processing device, the method comprising:

acquiring a first image, the first image being a color image that includes a plurality of channels, and includes an object image including information within a wavelength band of white light;

acquiring a second image, the second image being an image that includes an object image including information within a specific wavelength band, and differs from the plurality of channels included in the first image;

detecting an attention area based on a feature quantity of each pixel within the second image; and displaying an alert area in a corresponding attention area within an output image that corresponds to the attention area, the alert area indicating information about an attention area detection result.

BRIEF DESCRIPTION OF THE DRAWINGS

FIG. 4 illustrates the RGB spectral characteristics of color filters.

FIG. 5 illustrates the spectral characteristics of color filters g2 and b2.

FIG. 6 is a view illustrating color filters g2 and b2.

DESCRIPTION OF EXEMPLARY EMBODIMENTS

Figure 1A:
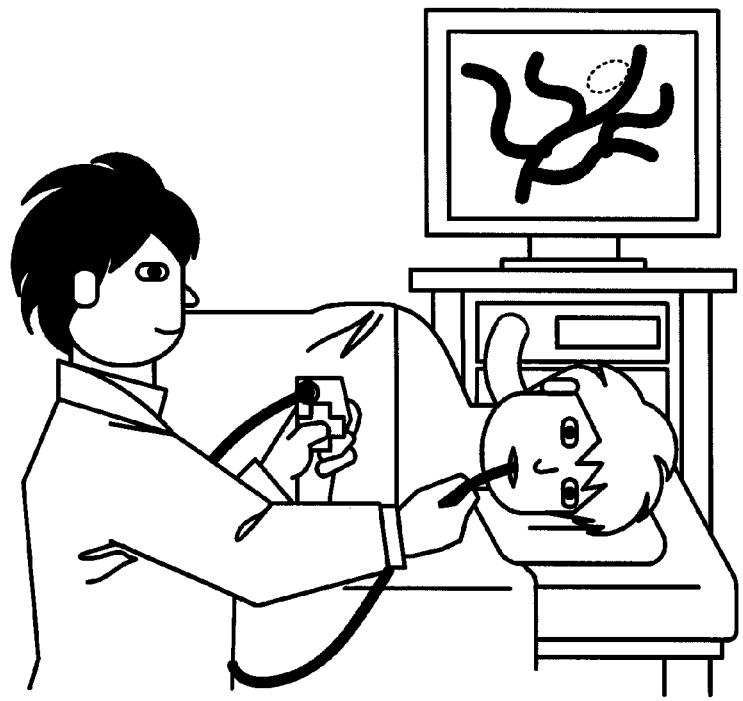
FIGS. 1A and 1B illustrate a related-art method.

According to one embodiment of the invention, there is provided an image processing device comprising:

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

a candidate attention area detection section that detects a candidate attention area based on a feature quantity of each pixel within the second image, the candidate attention area being a candidate for an attention area;

a reliability calculation section that calculates reliability that indicates a likelihood that the candidate attention area detected by the candidate attention area detection section is the attention area; and a display mode setting section that performs a display mode setting process that sets a display mode of an output image corresponding to the reliability calculated by the reliability calculation section.

According to one embodiment of the invention, the first image that corresponds to the wavelength band of white light, and the second image that corresponds to the specific wavelength band are acquired, and the candidate attention area is detected based on the feature quantity of the second image. Since the display mode is set taking account of the reliability calculated by the reliability calculation section, an appropriate display mode can be set as compared with the case where the reliability is not used.

According to another embodiment of the invention, there is provided an image processing device comprising;

a first image acquisition section that acquires a first image, the first image being a color image that includes a plurality of channels, and includes an object image including information within a wavelength band of white light;

a second image acquisition section that acquires a second image, the second image being an image that includes an object image including information within a specific wavelength band, and differs from the plurality of channels included in the first image;

an attention area detection section that detects an attention area based on a feature quantity of each pixel within the second image; and a display mode setting section that displays an alert area in a corresponding attention area within an output image that corresponds to the attention area, the alert area indicating information about an attention area detection result.

According to another embodiment of the invention, there is provided an electronic apparatus comprising:

the image processing device.

According to another embodiment of the invention, there is provided an endoscope system comprising:

a first light source that applies white light to an in vivo object;

a second light source that applies light within a specific wavelength band to an in viva object;

a first image acquisition section that acquires a first in vivo image, the first in vivo image being an image that is obtained using the first light source and includes an object image including information within a wavelength band of white light;

a second image acquisition section that acquires a second in vivo image, the second in vivo image being an image that is obtained using the second light source and includes an object image including information within the specific wavelength band;

a candidate attention area detection section that detects a candidate attention area based on a feature quantity of each pixel within the second in vivo image, the candidate attention area being a candidate for an attention area;

a reliability calculation section that calculates reliability that indicates a likelihood that the candidate attention area detected by the candidate attention area detection section is the attention area;

a display mode setting section that performs a display mode setting process that sets a display mode of an output image corresponding to the reliability calculated by the reliability calculation section; and a display section that displays the output image according to the display mode set by the display mode setting section.

According to the above embodiment of the invention, the first in vivo image and the second in vivo image are acquired, and the candidate attention area is detected based on the feature quantity of the second image. Since the display mode is set taking account of the reliability calculated by the reliability calculation section, an appropriate display mode can be set as compared with the case where the reliability is not used. This makes it possible to implement an endoscope system that displays an image on a display section according to the display mode that has been set.

According to another embodiment of the invention, there is provided an information storage device storing a program that causes a computer to function as above sections.

According to another embodiment of the invention, there is provided a method of controlling an image processing device, the method comprising:

acquiring a first image, the first image being a color image that includes a plurality of channels, and includes an object image including information within a wavelength band of white light;

acquiring a second image, the second image being an image that includes an object image including information within a specific wavelength band, and differs from the plurality of channels included in the first image;

detecting a candidate attention area based on a feature quantity of each pixel within the second image, the candidate attention area being a candidate for an attention area;

calculating reliability that indicates a likelihood that the candidate attention area is the attention area; and performing a display mode setting process that sets a display mode of an output image corresponding to the reliability.

According to another embodiment of the invention, there is provided a method of controlling an image processing device, the method comprising:

acquiring a first image, the first image being a color image that includes a plurality of channels, and includes an object image including information within a wavelength band of white light;

acquiring a second image, the second image being an image that includes an object image including information within a specific wavelength band, and differs from the plurality of channels included in the first image;

detecting an attention area based on a feature quantity of each pixel within the second image; and displaying an alert area in a corresponding attention area within an output image that corresponds to the attention area, the alert area indicating information about an attention area detection result. Exemplary embodiments of the invention are described below. Note that the following exemplary embodiments do not in any way limit the scope of the invention laid out in the claims. Note also that all of the elements of the following exemplary embodiments should not necessarily be taken as essential elements of the invention.

1. Method

A method according to several embodiments of the invention is described below with reference to FIGS. 1A, 1B, and 2.

Figure 1B:
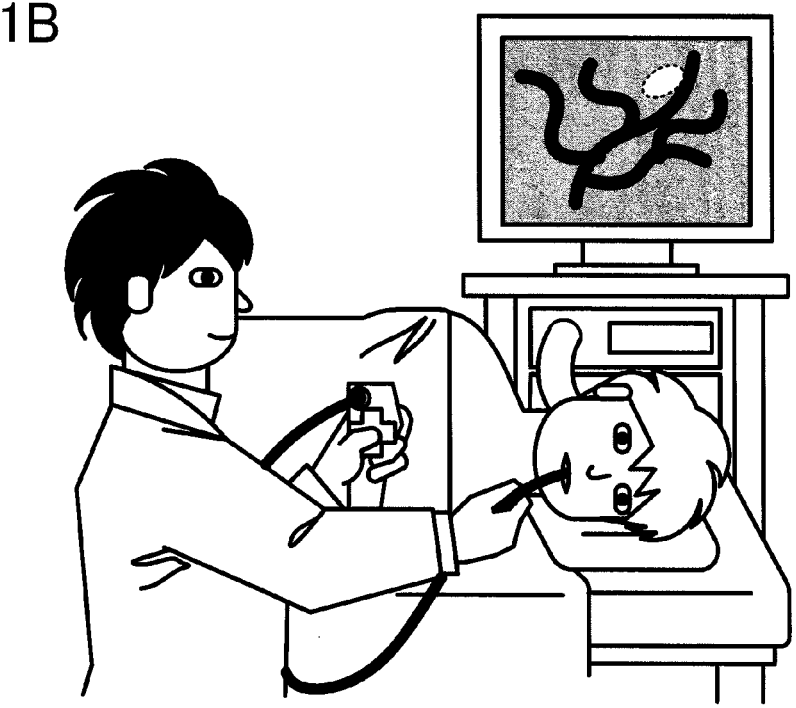

FIGS. 1A and 1B illustrate a related-art method. FIG. 1A illustrates the state of observation using normal light. A bright image that can be easily observed is obtained using normal light. However, it is difficult to observe some lesion (e.g., epidermoid cancer) when using normal light. FIG. 1B illustrates the state of observation using special light (e.g., narrow-band light or fluorescence). In this case, the visibility of some lesion can be improved (e.g., a lesion such as epidermoid cancer is displayed in brown) as compared with observation using normal light. However, a dark image that is difficult to observe is obtained using special light.

In order to solve these problems, diagnosis or treatment may be performed while selectively displaying the normal light image or the special light image by operating the system (e.g., switch). According to this method, however, the burden on the doctor increases since it is necessary to operate the system and observe the screen while moving the insertion section of the endoscope. Moreover, since the normal light image and the special light image have drawbacks, it is necessary to appropriately select the display image depending on the situation. This may require skill.

The normal light image and the special light image may be displayed side by side. In this case, since it is necessary to observe two screens (images) at the same time, the burden on the doctor increases. As a result, a lesion area may be missed, for example.

Figure 2:
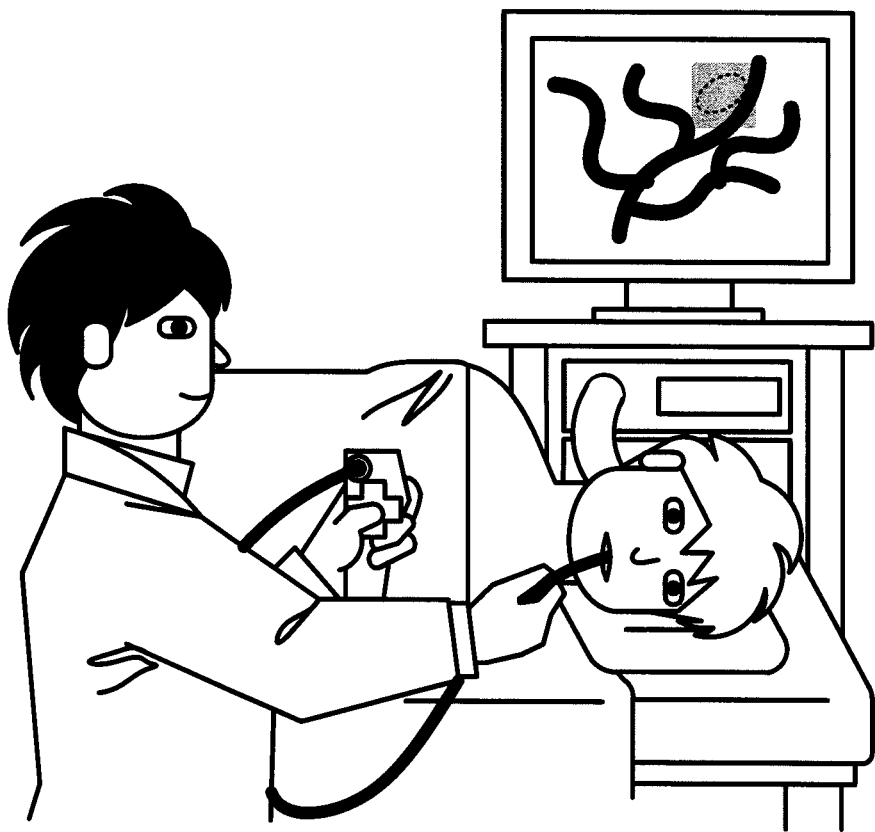
FIG. 2 is a view illustrating a method according to one embodiment of the invention.

In order to deal with the above problems, several embodiments of the invention propose a system illustrated in FIG. 2. Specifically, the visibility of a lesion area (e.g., epidermoid cancer) is improved by specifying the position of the lesion area from the special light image, and processing the normal light image based on the information about the position of the lesion area. For example, the target color is superimposed on (displayed within) the normal light image (see FIG. 2), or the lesion area is enclosed by an area in the target color, or the normal light image and the special light image are blended in the lesion area.

Since the advantage (i.e., high visibility of a lesion area) of the special light image is thus added to the advantage (i.e., bright and easy to observe) of the normal light image, smooth diagnosis or treatment can be implemented by preventing a situation in which a lesion area is missed, and reducing the burden on the doctor.

Note that the special light image can also be displayed by operating the system (e.g., switch). For example, the processed normal light image may be used when searching for a lesion area, and the special light image may be used when checking the lesion area in detail (i.e., the images may be selectively used).

2. First Embodiment

Figure 3:
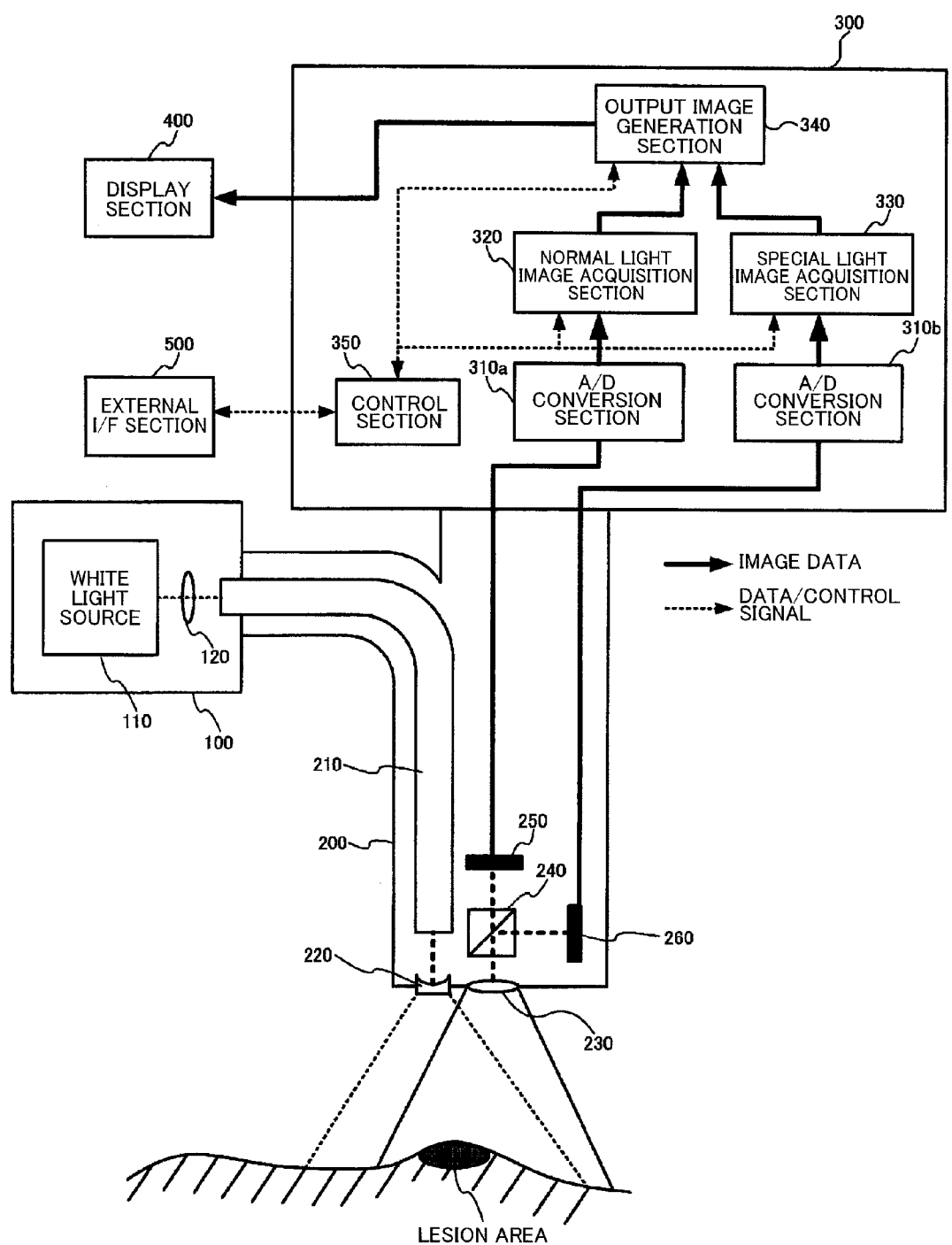
FIG. 3 illustrates a system configuration example according to one embodiment of the invention.

An endoscope system according to a first embodiment of the invention is described below with reference to FIG. 3. The endoscope system according to the first embodiment includes a light source section 100, an insertion section 200, an image processing section 300, a display section 400, and an external I/F section 500.

The light source section 100 includes a white light source 110 that emits white light, and a condenser lens 120 that focuses white light on a light guide fiber 210.

The insertion section 200 is formed to be elongated and flexible (i.e., can be curved (bent)) so that the insertion section 200 can be inserted into a body cavity or the like. The insertion section 200 includes the light guide fiber 210 that guides light focused by the light source section 100, an illumination lens 220 that diffuses light that has been guided by the light guide fiber 210, and illuminates an observation target, an objective lens 230 that focuses light reflected by the observation target, a half mirror 240 that divides (separates) the focused reflected light into two parts, and a first imaging element 250 and a second imaging element 260 that detect the reflected light divided by the half mirror 240.

The first imaging element 250 includes a Bayer color filter array that is used to capture a normal light image. Color filters R, G, and B of the first imaging element 250 have spectral characteristics illustrated in FIG. 4, for example. The second imaging element 260 captures a narrow-band image. As illustrated in FIG. 6, the second imaging element 260 is configured so that color filters g2 that allow narrow-band light G2 to pass through and color filters b2 that allow narrowband light B2 to pass through are disposed in a staggered arrangement, for example. As illustrated in FIG. 5, the color filter g2 of the second imaging element 260 allows light within a wavelength band of 530 to 550 nm to pass through, and the color filter b2 of the second imaging element 260 allows light within a wavelength band of 390 to 445 nm to pass through, for example.

The image processing section 300 (image processing device) includes A/D conversion sections 310a and 310b, a normal light image acquisition section 320, a special light image acquisition section 330, an output image generation section 340, and a control section 350. The control section 350 is bidirectionally connected to the normal light image acquisition section 320, the special light image acquisition section 330, and the output image generation section 340, and controls the normal light image acquisition section 320, the special light image acquisition section 330, and the output image generation section 340.

The external I/F section 500 is an interface that allows the user to perform an input operation or the like on the endoscope system (imaging apparatus). The external I/F section 500 includes a power switch (power ON/OFF switch), a shutter button (capture operation start button), a mode (e.g., capture mode) switch button, and the like. The external I/F section 500 outputs input information to the control section 350.

The A/D conversion section 310a converts an analog signal output from the first imaging element 250 into a digital signal, and outputs the digital signal. The A/D conversion section 310b converts an analog signal output from the second imaging element 260 into a digital signal, and outputs the digital signal.

The normal light image acquisition section 320 (first image acquisition section in abroad sense) acquires a normal light image (first image in a broad sense) from the digital signal output from the A/D conversion section 310a, for example. The special light image acquisition section 330 (second image acquisition section in a broad sense) acquires a special light image (second image in a broad sense) from the digital signal output from the A/D conversion section 310b, for example. The details of the normal light image acquisition section 320 and the special light image acquisition section 330 are described later.

The normal light image acquired by the normal light image acquisition section 320 and the special light image acquired by the special light image acquisition section 330 are output to the output image generation section 340. The output image generation section 340 generates one output image from the normal light image and the special light image, and outputs the output image to the image display section 400. The details of the output image generation section 340 are described later.

The details of the normal light image acquisition section 320 are described below with reference to FIG. 7. The normal light image acquisition section 320 includes a normal light image generation section 321 and a normal light image storage section 322. The normal light image generation section 321 processes the digital signal input from the A/D conversion section 310a to generate a normal light image. More specifically, the normal light image generation section 321 performs an interpolation process, a white balance process, a color conversion process, a grayscale transformation process, and the like on the digital signal to generate a normal light image, and outputs the normal light image. The normal light image storage section 322 stores the normal light image output from the normal light image generation section 321.

The details of the special light image acquisition section 330 are described below with reference to FIG. 8. The special light image acquisition section 330 includes a special light image generation section 331 and a special light image storage section 332. The special light image generation section 331 processes the digital image signal input from the A/D conversion section 310b to generate a special light image. In the first embodiment, the special light image is a narrow-band light image.

The special light image generation section 331 generates the narrow-band light image as described below. A digital image signal input to the special light image generation section has a configuration in which the color filters g2 and b2 are disposed in a staggered arrangement (see FIG. 6). The special light image generation section 331 performs an interpolation process on the image signal to generate a G2 image in which all of the pixels have a signal value of the filter g2, and a B2 image in which all of the pixels have a signal value of the filter b2. The pixel value calculated by the interpolation process may be the average value of the pixel values of the four peripheral pixels. For example, the pixel value b2(1, 1) at the position g2(1, 1) and the pixel value g2(1, 2) at the position b2(1, 2) illustrated in FIG. 6 are calculated by the following expressions (1) and (2).

$$b2(1,1)=[b2(0,1)+b2(1,0)+b2(1,2)+b2(2,1)]/4 \quad (1)$$

$$g2(1,2)=[g2(0,2)+g2(1,1)+g2(1,3)+g2(2,2)]/4 \quad (2)$$

A color image that includes R, G, and B channels is generated from the G2 image and the B2 image obtained by the interpolation process. For example, a color image is generated by inputting the G2 image to the R channel, and inputting the B2 image to the G channel and the B channel. The special light image generation section 331 performs a white balance process, a grayscale transformation process, and the like on the generated color image, and outputs the resulting color image as a narrow-band light image. The special light image storage section 332 stores the special light image output from the special light image generation section 331.

Figure 9:
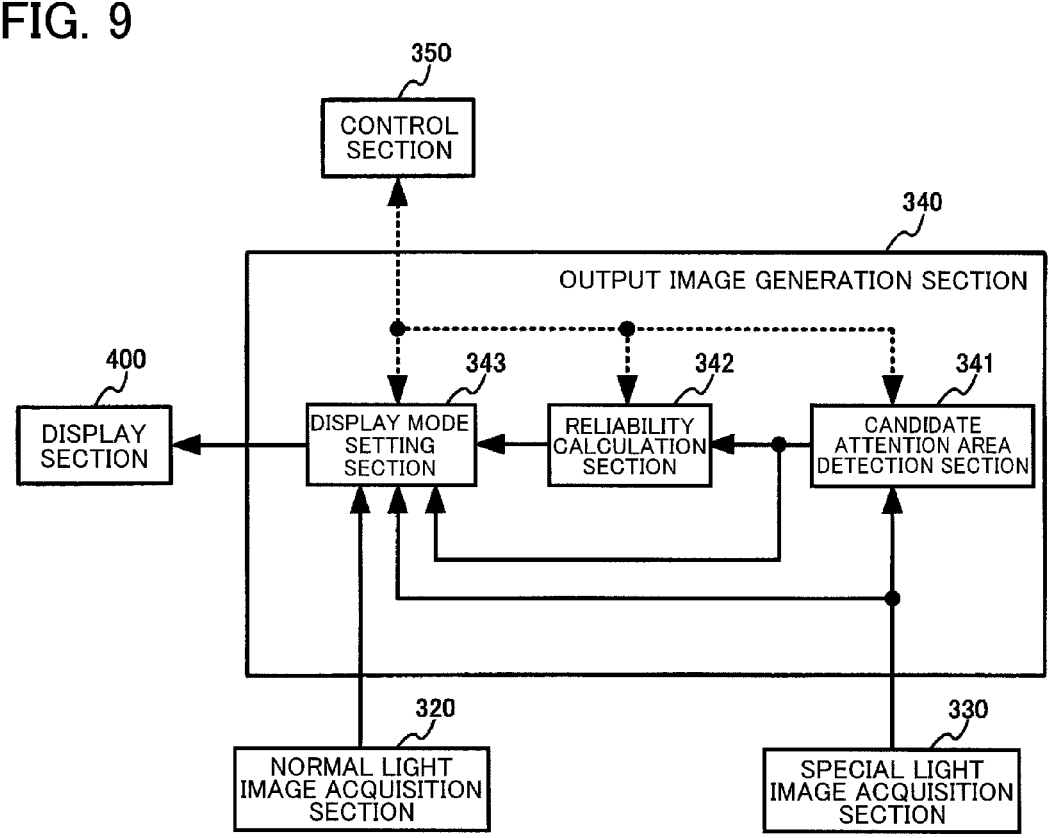
FIG. 9 illustrates a configuration example of an output image generation section.

The configuration of the output image generation section 340 is described below. FIG. 9 is a block diagram illustrating an example of the configuration of the output image generation section 340 according to the first embodiment. The output image generation section 340 includes a candidate attention area detection section 341, a reliability calculation section 342, and a display mode setting section 343.

The image signal output from the normal light image acquisition section 320 is input to the display mode setting section 343. The image signal output from the special light image acquisition section 330 is input to the candidate attention area detection section 341 and the display mode setting section 343. The candidate attention area detection section 341 is connected to the reliability calculation section 342 and the display mode setting section 343. The details of the candidate attention area detection section 341 are described later. The reliability calculation section 342 is connected to the display mode setting section 343. The display mode setting section 343 is connected to the display section 400. The control section 350 is bidirectionally connected to the candidate attention area detection section 341, the reliability calculation section 342, and the display mode setting section 343, and controls the candidate attention area detection section 341, the reliability calculation section 342, and the display mode setting section 343.

Figure 10:
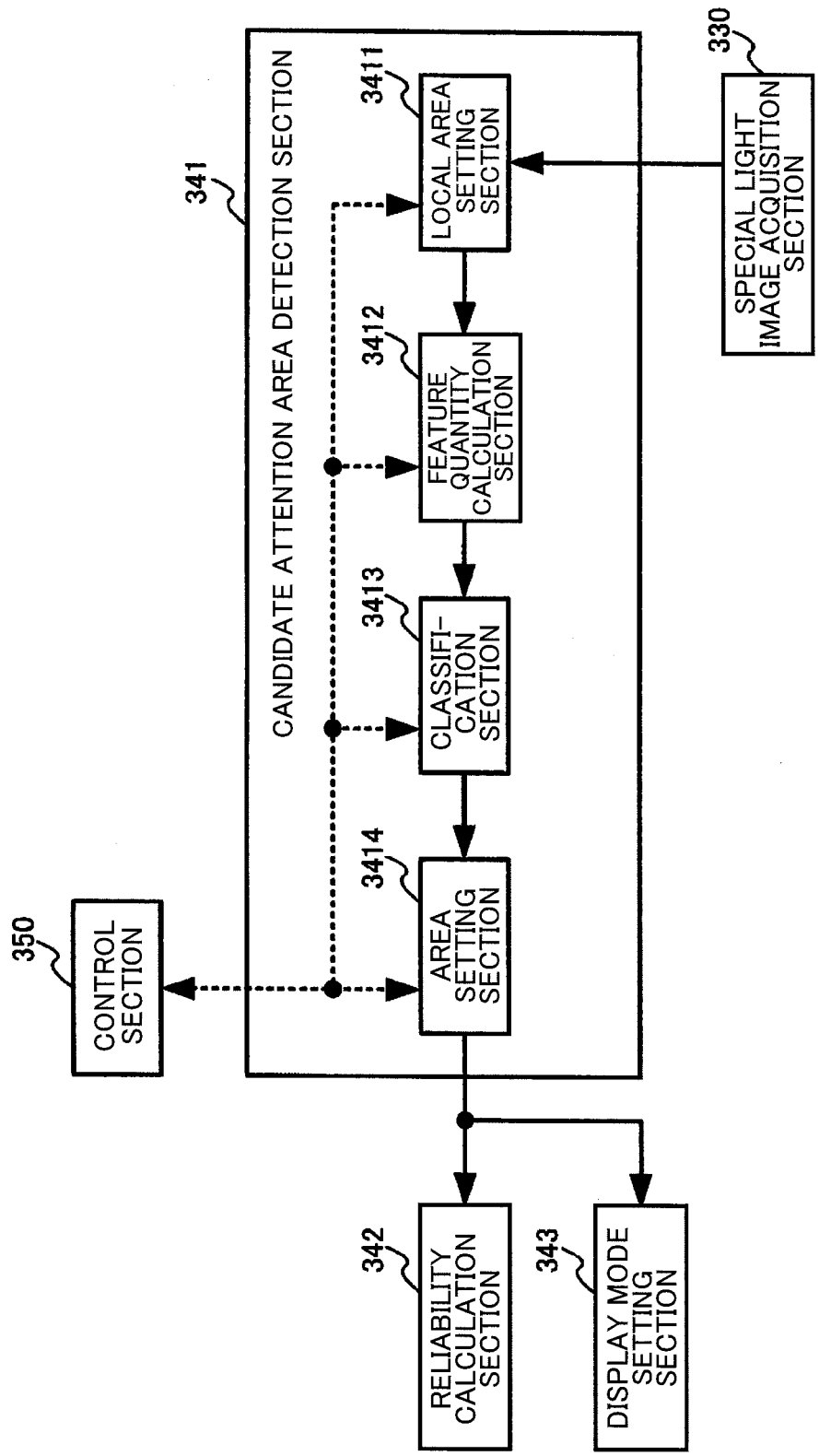
FIG. 10 illustrates a configuration example of a candidate attention area detection section.

The candidate attention area detection section 341 detects the candidate attention area (i.e., a candidate for an attention area) from the special light image under control of the control section 350. The configuration of the candidate attention area detection section 341 is described below. FIG. 10 is a block diagram illustrating an example of the configuration of the candidate attention area detection section 341 according to the first embodiment. As illustrated in FIG. 10, the candidate attention area detection section 341 includes a local area setting section 3411, a feature quantity calculation section 3412, a classification section 3413, and an area setting section 3414.

The special light image acquisition section 330 is connected to the local area setting section 3411. The local area setting section 3411 is connected to the feature quantity calculation section 3412. The feature quantity calculation section 3412 is connected to the classification section 3413. The classification section 3413 is connected to the area setting section 3414. The area setting section 3414 is connected to the reliability calculation section 342 and the display mode setting section 343. The control section 350 is bidirectionally connected to the local area setting section 3411, the feature quantity calculation section 3412, the classification section 3413, and the area setting section 3414, and controls the local area setting section 3411, the feature quantity calculation section 3412, the classification section 3413, and the area setting section 3414.

Figure 13:
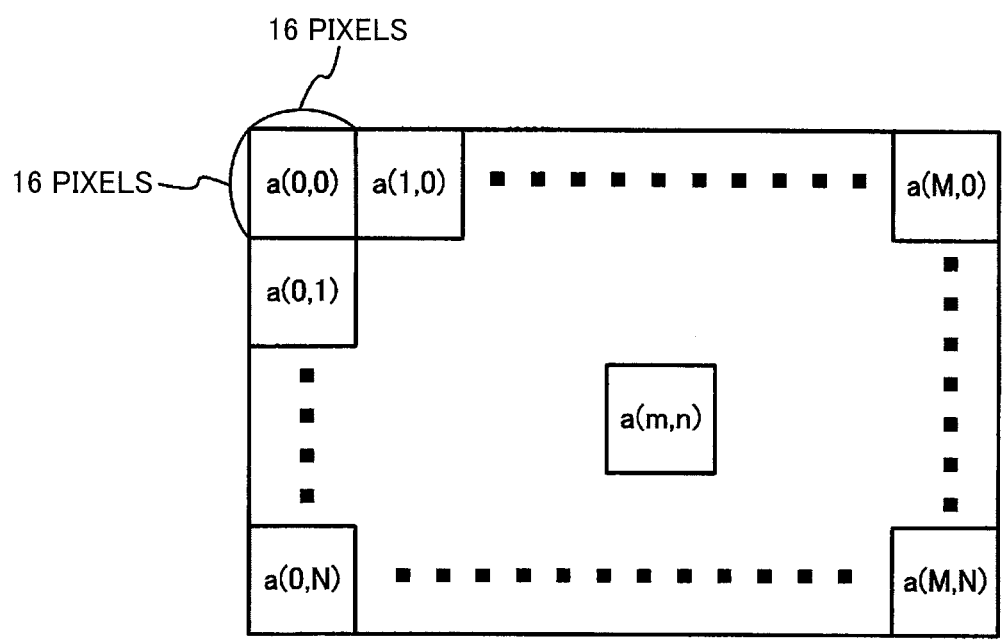
FIG. 13 is a view illustrating a local area setting method.

The local area setting section 3411 sets a plurality of local areas (blocks in a narrow sense) within the special light image output from the special light image acquisition section 330. For example, the local area setting section 3411 divides the special light image into a plurality of rectangular areas, and sets each rectangular areas as the local area. The size of each rectangular area may be appropriately set. For example, each local area includes 16×16 pixels (see FIG. 13). The special light image includes M×N local areas, and the coordinates of each local area are indicated by (m, n). The local area positioned at the coordinates (m, n) is indicated by a(m, n). The coordinates of the local area positioned at the upper left of the image are indicated by (0, 0). The rightward direction is the positive direction of the coordinate value m, and the downward direction is the positive direction of the coordinate value n. Note that the local area need not necessarily be rectangular. The special light image may be divided into a plurality of arbitrary polygonal areas, and each polygonal area may be set as the local area. The special light image may be divided into a plurality of local areas by applying a known area division algorithm (e.g., texture analysis). The local area may be arbitrarily set based on instructions from the user. In the example illustrated in FIG. 13, an area that includes a plurality of adjacent pixels is set as the local area in order to reduce the amount of calculations and remove noise. Note that one pixel may be set as the local area. In this case, the subsequent process is performed in the same manner as in the case where each local area includes a plurality of adjacent pixels. The information about each local area is output to the feature quantity calculation section 3412.

The feature quantity calculation section 3412 calculates the feature quantity of each local area. An example in which color information is used as the feature quantity is described below. In the narrow-band image used as the special light image, a lesion area such as epidermoid cancer is drawn as a brown area. Therefore, the lesion area can be detected by utilizing hue H as the feature quantity. The signal values of the R, G, and B channels are respectively referred to as r, g, and b, and indicated by 8 bits (0 to 255).

The hue H is calculated by the following expressions (3) to (8) using the signal values r, g, and b, for example.

$$\text{max}=\text{MAX}(r,g,b) \quad (3)$$

The MAX function outputs the maximum argument among a plurality of arguments.

When MAX is 0:

$$H=0 \quad (4)$$

When MAX is not 0:

$$d=\text{MAX}(r,g,b)-\text{MIN}(r,g,b) \quad (5)$$

The MIN function outputs the minimum argument among a plurality of arguments.

When r is a maximum among r, g, and b:

$$H=60*(g-b)/d \quad (6)$$

When g is a maximum among r, g, and b:

$$H=60*\{2+(b-r)\}/d \quad (7)$$

When b is a maximum among r, g, and b:

$$H=60*\{4+(r-g)\}/d \quad (8)$$

When the hue H is smaller than 0, 360 is added to the hue H. The hue H is considered to be 0 when the hue H is 360.

The number of brown pixels included in the local area positioned at the coordinates (m, n) is indicated by "Cha(m, n)", and is used as the feature quantity. Note that the feature quantity that indicates the likelihood of a lesion is not limited to the above example. For example, the feature quantity of the color, the feature quantity of the spatial frequency, the feature quantity of the shape, the feature quantity of the area, and the like may respectively be calculated, multiplied by a weighting coefficient, and linearly combined to obtain the feature quantity of each local area that indicates the likelihood of a lesion. The feature quantity Cha(m, n) is output to the classification section 3413.

The classification section 3413 compares the feature quantity Cha(m, n) of each local area with a given threshold value under control of the control section 350, and classifies each local area into one of a plurality of groups corresponding to the comparison results. The classification section 3413 uses a plurality of threshold values GrThi (i=0, 1, and L) that are set in advance, and classifies the local area positioned at the coordinates (m, n) into a group i when the feature quantity Cha(m, n) is equal to or larger than GrThi and less than GrThi+1. The following description is given on the assumption that GrTh0=200, GrThL=257, and GrThi<GrThi+1. Each local area is classified into one of groups 0 to L. A group into which a local area positioned at the coordinates (m, n) has been classified is indicated by i(m, n). The threshold value GrThi may be set by an arbitrary method. For example, the threshold value GrThi may be automatically set by the control section 350. Alternatively, the threshold value GrThi may be adaptively set based on the position within the special light image. The information about the group i(m, n) is output to the area setting section 3414.

Figure 14B:
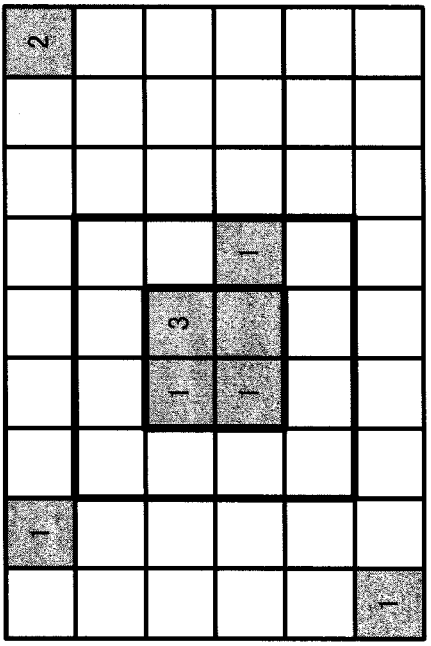
FIGS. 14A, 14B, 14C, and 14D are views illustrating a method that unites adjacent candidate attention areas.
Figure 14D:
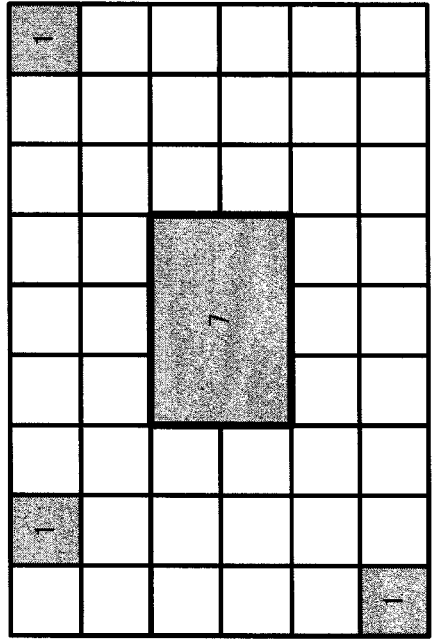
Figure 14A:
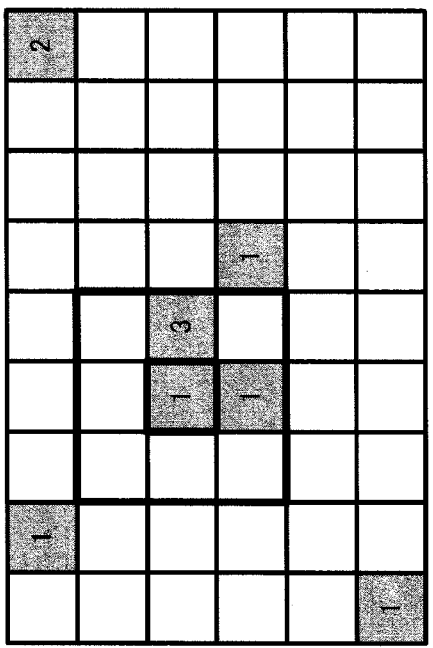
Figure 14C:
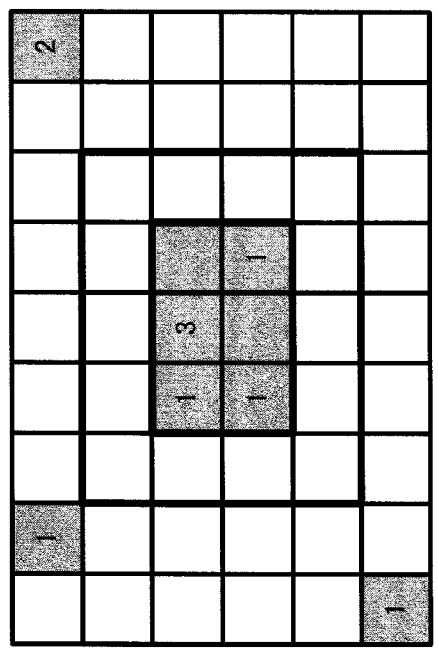

The area setting section 3414 detects an area that includes each local area that has been classified into at least one of a plurality of groups and a local area group adjacent thereto as the candidate attention area under control of the control section 350. FIGS. 14A, 14B, 14C, and 14D illustrate an example of a candidate attention area setting method. The numerical value written in each local area indicates the group into which the local area has been classified. As illustrated in FIG. 14A, a local area that has been classified into a group is searched within a range of eight local areas positioned around the local area enclosed by a thick frame. When a local area that has been classified into a group is present within the above range, a rectangular area that includes the local area that has been found is set as a local area group (see the inner thick frame in FIG. 14B). A local area that has been classified into a group is then searched within a range (enclosed by the outer thick frame) around the local area group. This process is repeated until a local area that has been classified into a group is not found within a range around the local area group (see FIG. 14C). When the search process has completed, the local areas included in the local area group are united (see FIG. 14D), and then classified into one of a plurality of groups as described above. Note that FIG. 14D illustrates an example in which the number of reddish brown pixels included in the united local area is equal to or more than GrTh7 and less than GrTh8 (i.e., the united local area is classified into the group 7). The united local area is set as the candidate attention area. Note that the local areas may be united by an arbitrary method. For example, the local areas may be united by applying a known clustering algorithm. In this case, the united local area need not necessarily have a rectangular shape, but may have an arbitrary shape. When the candidate attention area has been detected, the image signal and information about the coordinates of each pixel and the group into which the candidate attention area has been classified, are output to the reliability calculation section 342 and the display mode setting section 343.

The candidate attention area detection section may detect the candidate attention area from the first image using the feature quantity of each pixel included in the second image instead of detecting the candidate attention area from the second image using the feature quantity of each pixel included in the second image.

In this case, the local area setting section 3411 sets a plurality of local areas within the second image. The feature quantity calculation section 3412 calculates the feature quantity of each local area. The feature quantity calculation section 3412 performs the threshold process using the feature quantity of each pixel of the first image that corresponds to each pixel of the second image that is included in each local area (e.g., a pixel that is located at an identical pixel position in the first image and the second image). The area setting section 3414 sets the candidate attention area within the first image based on each local area within the first image that has been extracted by the threshold process. The area setting section 3414 may optionally unite adjacent local areas when setting the candidate attention area.

The local area setting section 3411 may set each pixel as the local area instead of setting an area that includes a plurality of (e.g., 16×16) pixels as the local area. In this case, the feature quantity calculation section 3412 calculates the feature quantity of each pixel, and the area setting section 3414 detects an attention pixel based on the feature quantity, and detects an area that includes the attention pixel as the candidate attention area.

The area setting section 3414 may reset the candidate attention area information so that attention area information that indicates an arbitrary shape (e.g., polygon or circle) is output even when detecting the candidate attention area using the attention pixel. In this case, the candidate attention area includes the attention pixel and a selected non-attention pixel. Note that the term "non-attention pixel" refers to a pixel that is included in the second image and has not been detected as the attention pixel, and the term "selected non-attention pixel" refers to a pixel that has been selected from the non-attention pixels (e.g., so that the candidate attention area has a given shape).

The area setting section 3414 may calculate the average luminance or intensity (saturation) of each local area by a known method instead of calculating the hue H, and may detect the candidate attention area using the average luminance or intensity as the feature quantity. The area setting section 3414 may calculate one feature quantity by arbitrarily combining the luminance information, the hue information, and the intensity information to detect the candidate attention area.

The reliability calculation section 342 discriminates between a plurality of candidate attention areas by adding tag information to each candidate attention area. For example, when two candidate attention areas have been detected (see FIG. 15A), the reliability calculation section 342 sets a tag value "1" to the local areas that belong to the candidate attention area 1, and sets a tag value "2" to the local areas that belong to the candidate attention area 2.

Figure 15A:
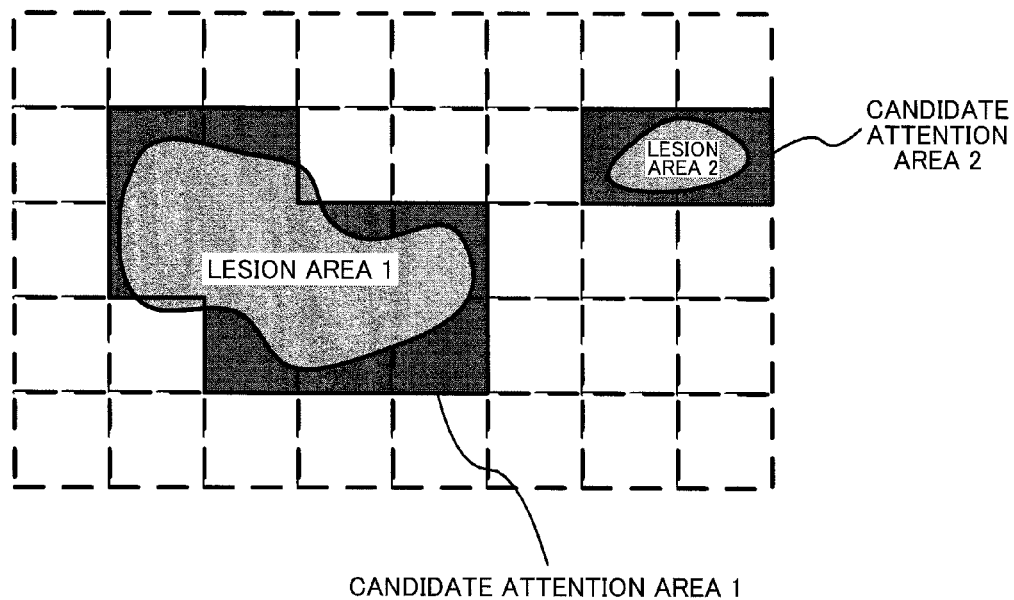
FIGS. 15A and 15B are views illustrating a candidate attention area setting method.

The reliability calculation section 342 calculates the area of each candidate attention area by calculating the number of local areas that belong to each candidate attention area based on information about the tag set to each local area, and calculates the reliability by performing a threshold process on the area of each candidate attention area. For example, the area d1 of the candidate attention area 1 and the area d2 of the candidate attention area 2 illustrated in FIG. 15A are respectively 9 and 2 when the area of one local area is 1. The reliability calculation section 342 sets the reliability of a candidate attention area having an area equal to or larger than 5 to "1", and sets the reliability of a candidate attention area having an area of less than 5 to "0", for example. The reliability calculation section 342 then outputs the reliability to the display mode setting section 343.

Note that the average hue, intensity, or luminance of each candidate attention area may be calculated, and the reliability of each candidate attention area may be calculated using the average hue, intensity, or luminance of the candidate attention area, instead of calculating the area of each candidate attention area from the number of local areas that belong to each candidate attention area, and calculating the reliability of each candidate attention area from the area of each candidate attention area. The reliability of each candidate attention area may also be calculated using the area and the hue, intensity, or luminance of each candidate attention area in combination.

The display mode setting section 343 sets an attention area using the candidate attention area information and the reliability. The display mode setting section 343 performs a processing process on the corresponding attention area within the normal light image. The display mode setting section 343 then selects an image displayed on the display section 400, and outputs the selected image. The display mode setting section 343 may optionally set an alert area in order from an attention area having a higher priority.

Figure 11:
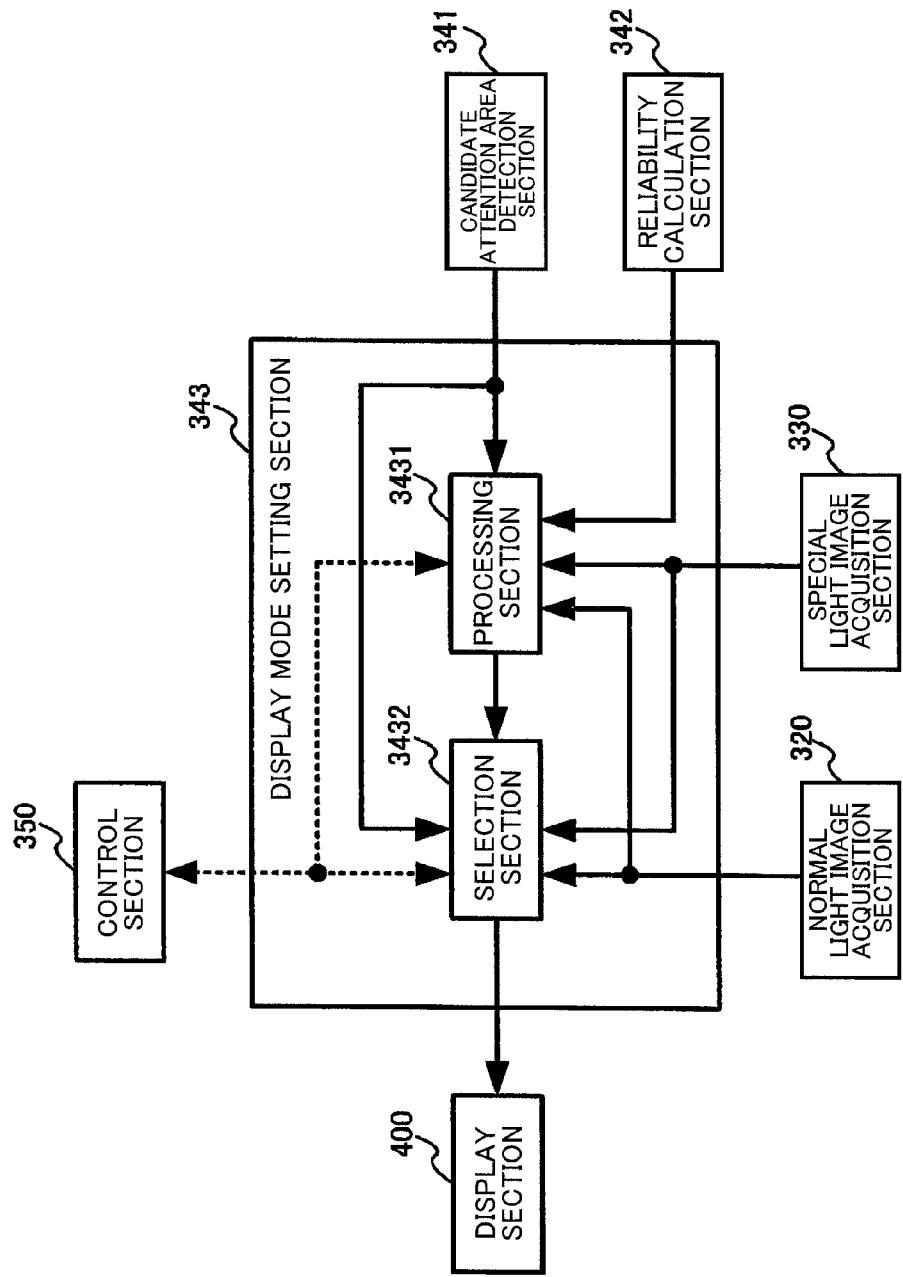
FIG. 11 illustrates a configuration example of a display mode setting section.

The configuration of the display mode setting section 343 is described below. FIG. 11 is a block diagram illustrating an example of the configuration of the display mode setting section 343 according to the first embodiment. The display mode setting section 343 includes a processing section 3431 and a selection section 3432.

The candidate attention area detection section 341 outputs the candidate attention area information to the processing section 3431. The candidate attention area detection section 341 outputs a control signal to the selection section 3432, the control signal indicating whether or not the candidate attention area has been detected. The image signal output from the normal light image acquisition section 320 is input to the processing section 3431 and the selection section 3432. The image signal output from the special light image acquisition section 330 is input to the processing section 3431 and the selection section 3432. The processing section 3431 processes the normal light image under control of the control section 350 using the candidate attention area information input from the candidate attention area detection section 341, and the reliability input from the reliability calculation section 342. The processing section 3431 outputs the processed normal light image to the selection section 3432. The control section 350 is bidirectionally connected to the processing section 3431 and the selection section 3432, and controls the processing section 3431 and the selection section 3432.

The processing section 3431 processes the corresponding attention area within the normal light image that corresponds to the detected attention area within the special light image based on the attention area detection result. The details of the processing section are described later.

The selection section 3432 selects the display image output to the display section 400 using the control signal input from the candidate attention area detection section 341. For example, the selection section 3432 selects the normal light image output from the normal light image acquisition section 320 as the display image when the candidate attention area has not been detected within the special light image, and selects the processed normal light image output from the processing section 3431 as the display image when the candidate attention area has been detected within the special light image. The selection section 3432 may select the normal light image output from the normal light image acquisition section 320 as the display image when the candidate attention area has not been detected within the special light image, and may select the special light image output from the special light image acquisition section 330 as the display image when the candidate attention area has been detected within the special light image. The user may determine in advance the image selected when the candidate attention area has been detected and the image selected when the candidate attention area has not been detected, and the selection section 3432 may be controlled based on the control signal input from the control section 350 to the selection section 3432, for example.

Figure 12:
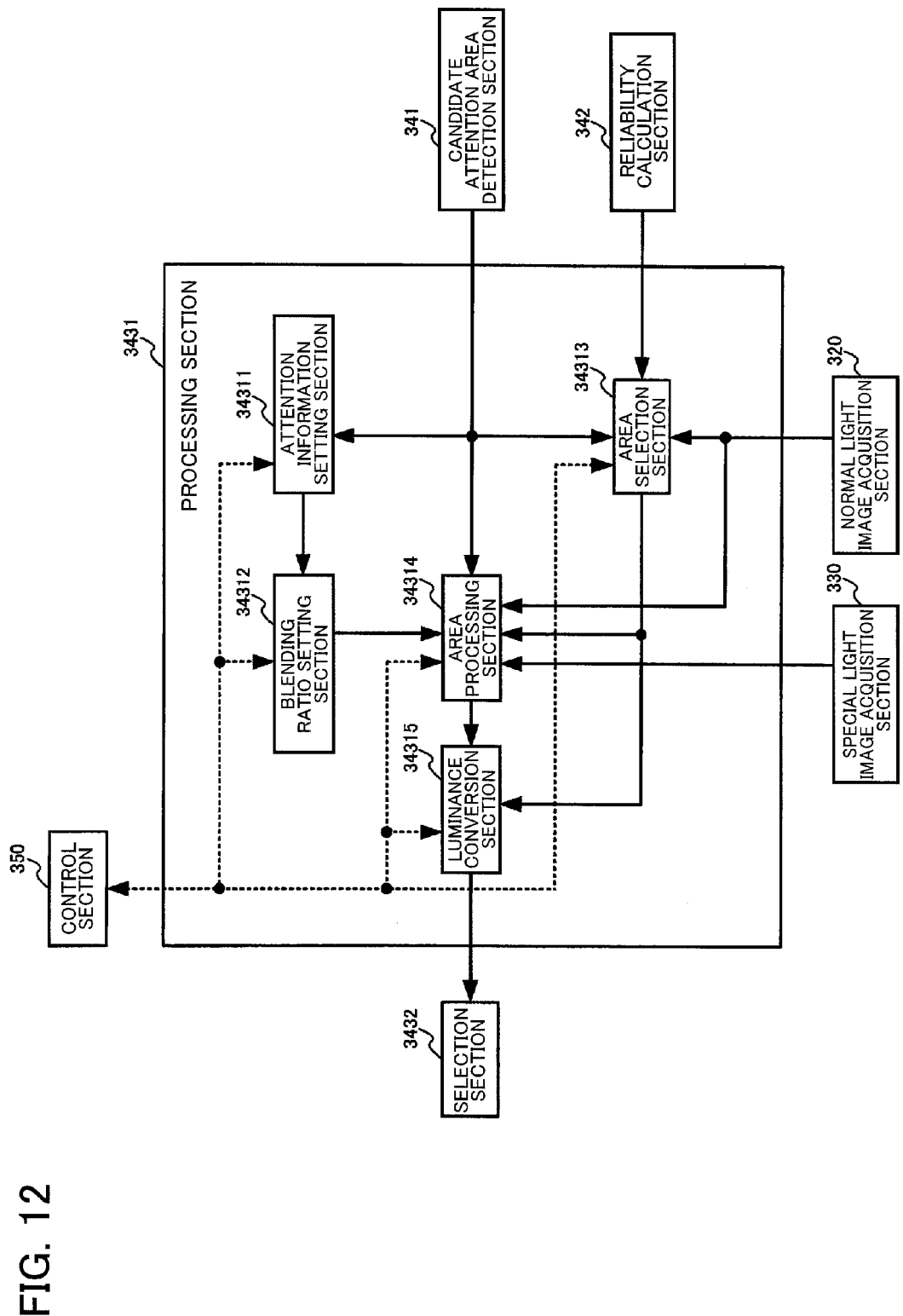
FIG. 12 illustrates a configuration example of a processing section.

The configuration of the processing section 3431 is described below. FIG. 12 is a block diagram illustrating an example of the configuration of the processing section 3431 according to the first embodiment. As illustrated in FIG. 12, the processing section 3431 includes an attention information setting section 34311, a blending ratio setting section 34312, an area selection section 34313, an area processing section 34314, and a luminance conversion section 34315.

The candidate attention area detection section 341 is connected to the attention information setting section 34311, the area selection section 34313, and the area processing section 34314. The reliability calculation section 342 is connected to the area selection section 34313. The attention information setting section 34311 is connected to the blending ratio setting section 34312. The blending ratio setting section 34312 is connected to the area processing section 34314. The normal light image acquisition section 320 is connected to the area selection section 34313. The area selection section 34313 is connected to the area processing section 34314 and the luminance conversion section 34315. The area processing section 34314 is connected to the luminance conversion section 34315. The luminance conversion section 34315 is connected to the selection section 3432. The control section 350 is bidirectionally connected to the attention information setting section 34311, the blending ratio setting section 34312, the area selection section 34313, the area processing section 34314, and the luminance conversion section 34315, and controls the attention information setting section 34311, the blending ratio setting section 34312, the area selection section 34313, the area processing section 34314, and the luminance conversion section 34315.

The attention information setting section 34311 sets the attention information that indicates the degree of attention corresponding to the detected candidate attention area under control of the control section 350. More specifically, the attention information setting section 34311 sets the degree of attention At corresponding to each candidate attention area based on the information about the group output from the candidate attention area detection section 341. The degree of attention At corresponding to each group is set as a look-up table AtLut(i) in advance. The look-up table AtLut(i) indicates the degree of attention corresponding to the group i (i.e., At=AtLut(i)). The degree of attention At corresponding to each group may be set by the user through the external I/F section 500. The calculated degree of attention At is output to the blending ratio setting section 34312 as the attention information about the candidate attention area.

The blending ratio setting section 34312 sets the blending ratio of the pixel value of the pixel within the candidate attention area and the pixel value of the pixel within the corresponding attention area, corresponding to the degree of attention indicated by the attention information, under control of the control section 350. More specifically, the blending ratio setting section 34312 calculates a blending ratio alpha using the following expression (9) based on the attention information (At) input from the attention information setting section 34311. Note that the blending ratio alpha is a value within the range from 0 to 1.

$$\text{alpha}=\text{alLut}(At) \tag{9}$$

Figure 16A:
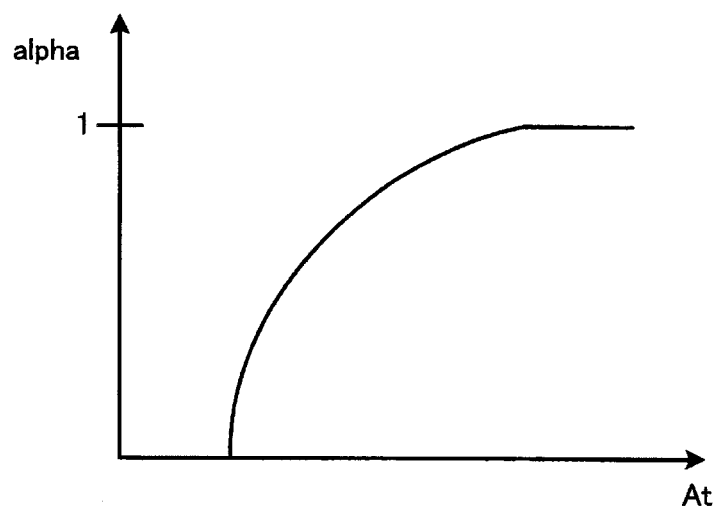
FIGS. 16A and 16B are views illustrating an example of the relationship between the degree of attention (At) and a blending ratio (alpha).
Figure 16B:
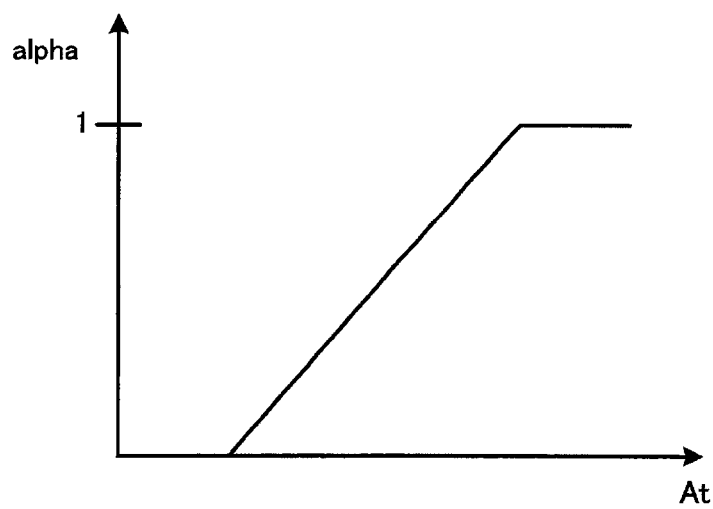

AlLut(x) is a blending ratio calculation look-up table (see FIG. 16A) set in advance, for example. The blending ratio may be calculated using an nth-order function. The following expression (10) is an example of a linear function used to calculate the blending ratio alpha.

$$\text{alpha}=a*At+b \tag{10}$$

where, a and b are constant terms. As illustrated in FIG. 16B, the blending ratio alpha is set to "0" when the blending ratio alpha is equal to or less than "0", and is set to "1" when the blending ratio alpha is equal to or more than "1". The blending ratio alpha is output to the area processing section 34314.

The area selection section 34313 selects the corresponding attention area within the normal light image that corresponds to the detected candidate attention area under control of the control section 350. Specifically, a calibration image is captured in advance, and a look-up table calLut(x, y) in which the position of each pixel within the normal light image is respectively linked to the position of each pixel within the special light image is generated by applying a known matching algorithm. The look-up table calLut(x, y) is designed so that the corresponding coordinates (x', y') within the normal light image are output by inputting the coordinates (x, y) of each pixel within the special light image. The area selection section 34313 selects the attention area from the candidate attention areas detected by the candidate attention area detection section 341 based on the reliability input from the reliability calculation section 342. More specifically, the area selection section 34313 extracts a candidate attention area having a reliability equal to or more than a preset threshold value as the attention area. The area selection section 34313 calculates the coordinates of the corresponding attention area using the look-up table calLut (x, y) and the coordinates of each pixel included in the attention area. Note that a plurality of pixel positions may be present corresponding to the attention area. When the pixel position corresponding to the attention area is present between pixels, a known interpolation algorithm (e.g., linear interpolation) may be applied. The coordinates of the corresponding attention area are output to the area processing section 34314.

The area processing section 34314 processes the corresponding attention area within the normal light image under control of the control section 350. More specifically, the area processing section 34314 performs a blending process on each pixel specified by the corresponding attention area information output from the area selection section 34313 using the following expression (11). Note that the signal value of the special light image is indicated by speImg(x, y), the signal value of the normal light image is indicated by whiImg(x, y), and the signal value of the blended image is indicated by bleImg(x, y).

$$bleImg(x',y')=alpha*speImg(x,y)+(1-alpha)*whiImg(x',y') \quad (11)$$

The normal light image is set as the blended image at pixels other than the pixels included in the corresponding attention area (see the following expression (12)).

$$bleImg(x',y')=whiImg(x',y') \quad (12)$$

The resulting blended image bleImg is output to the luminance conversion section 34315.

The luminance conversion section 34315 reduces the luminance of each pixel included in an area other than the corresponding attention area under control of the control section 350. More specifically, the luminance conversion section 34315 reduces the luminance of each pixel other than the pixels within the corresponding attention area selected by (output from) the area selection section 34313 using the following expression (13). Note that the signal value of the resulting processed image is indicated by procImg(x, y).

$$procImg(x',y')=c*bleImg(x',y') \quad (13)$$

where, c is a constant term within the range from 0 to 1. The resulting processed image progImg is output to the selection section 3432.

Note that each section of the image processing section 300 need not necessarily be implemented by hardware. For example, a CPU may perform the process of each section on an image acquired using an imaging apparatus such as a capsule endoscope. Specifically, the process of each section may be implemented by software by causing the CPU to execute a program. Alternatively, the process of each section may partially be implemented by software.

When separately providing the imaging section, and implementing the process of each section of the image processing section 300 by software, a known computer system (e.g., work station or personal computer) may be used as the image processing device. A program (image processing program) that implements the process of each section of the image processing section 300 may be provided in advance, and executed by the CPU of the computer system.

Figure 17:
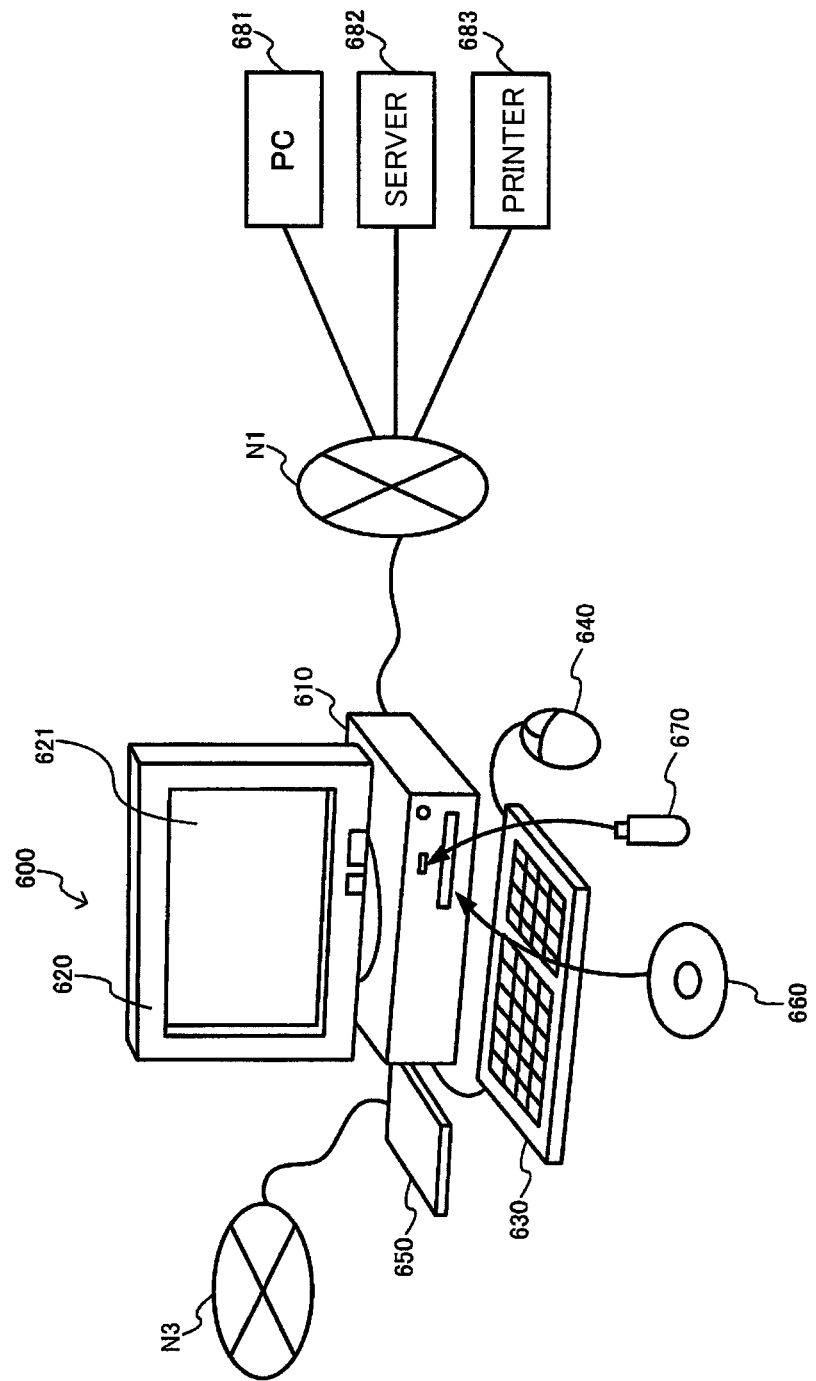
FIG. 17 illustrates a configuration example of a computer used for a software process.
Figure 18:
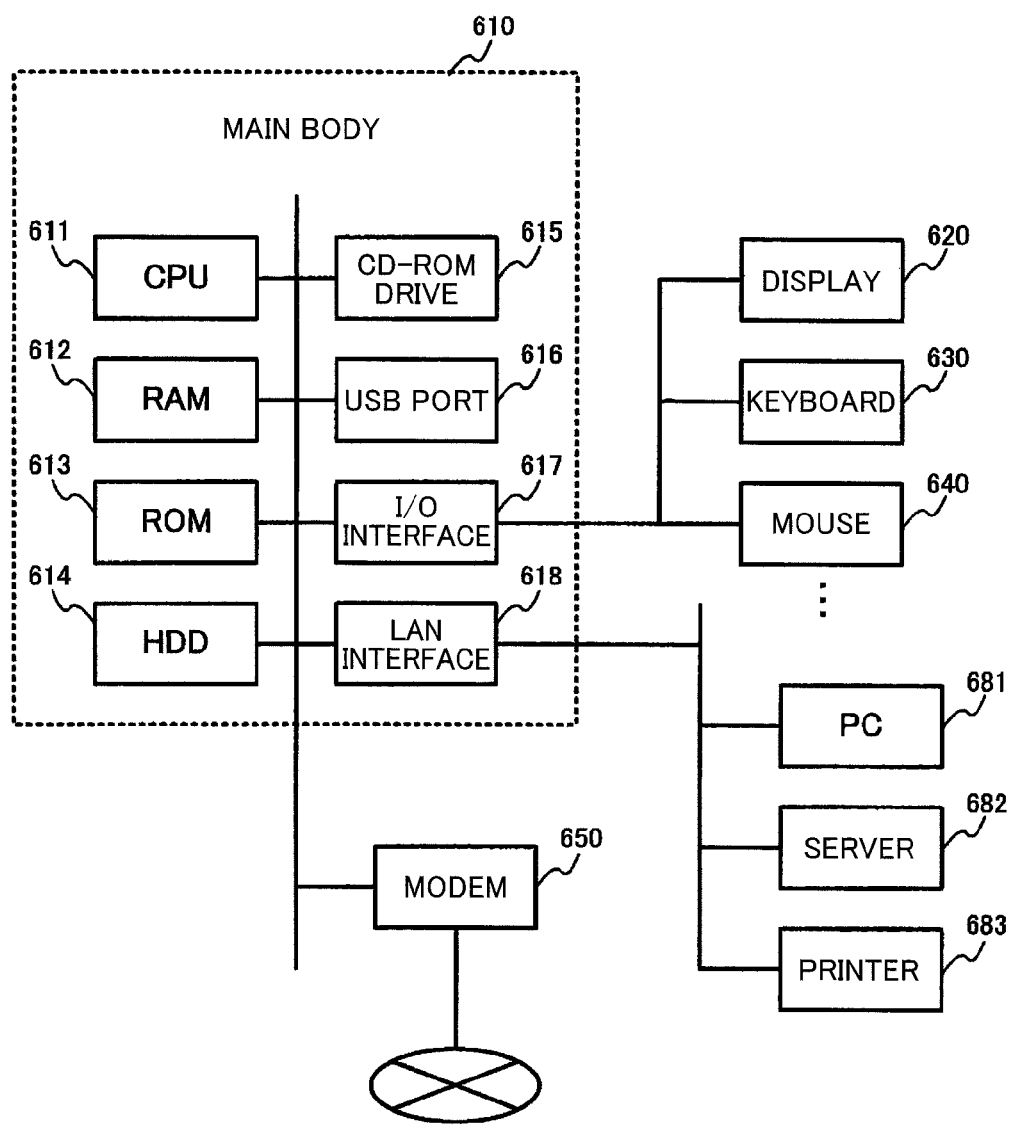
FIG. 18 illustrates a configuration example of a computer used for a software process.

FIG. 17 is a system configuration diagram illustrating the configuration of a computer system 600 according to such a modification. FIG. 18 is a block diagram illustrating the configuration of a main body 610 of the computer system 600. As illustrated in FIG. 17, the computer system 600 includes the main body 610, a display 620 that displays information (e.g., image) on a display screen 621 based on instructions from the main body 610, a keyboard 630 that allows the user to input information to the computer system 600, and a mouse 640 that allows the user to designate an arbitrary position on the display screen 621 of the display 620.

As illustrated in FIG. 18, the main body 610 of the computer system 600 includes a CPU 611, a RAM 612, a ROM 613, a hard disk drive (HDD) 614, a CD-ROM drive 615 that receives a CD-ROM 660, a USB port 616 to which a USB memory 670 is removably connected, an I/O interface 617 that connects the display 620, the keyboard 630, and the mouse 640, and a LAN interface 618 that is used to connect to a local area network or a wide area network (LAN/WAN) N1.

The computer system 600 is connected to a modem 650 that is used to connect to a public line N3 (e.g., Internet). The computer system 600 is also connected to personal computer (PC) 681 (i.e., another computer system), a server 682, a printer 683, and the like via the LAN interface 618 and the local area network or the large area network N1.

Figure 22:
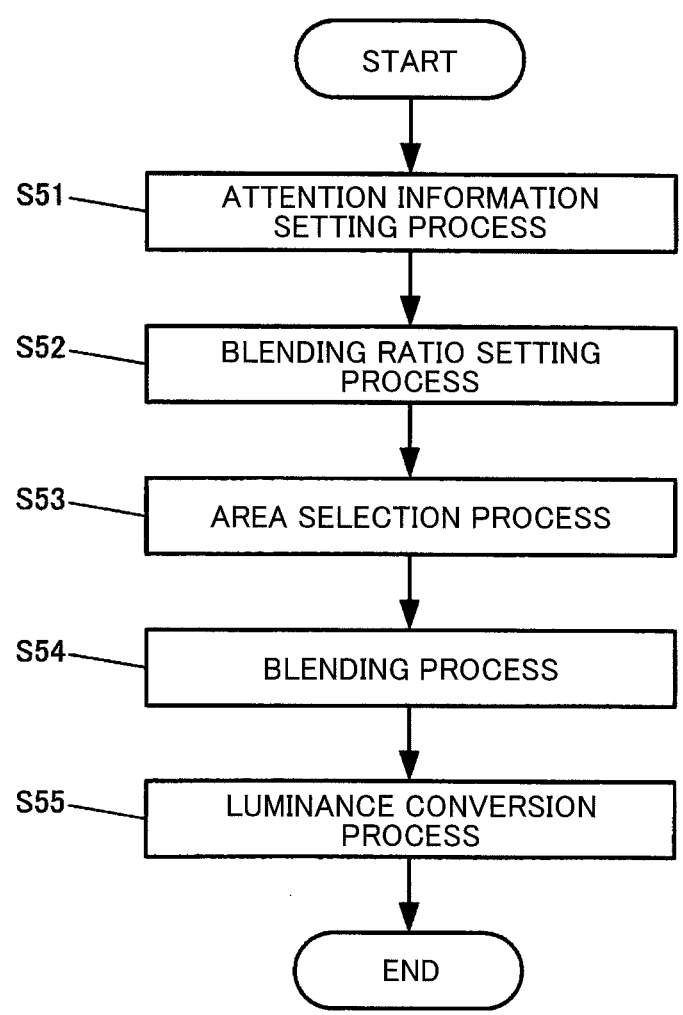
FIG. 22 is a flowchart illustrating a processing process.

The computer system 600 implements the functions of the image processing device by reading an image processing program (e.g., an image processing program that implements a process described below with reference to FIGS. 19 and 22) recorded on a given recording medium, and executing the image processing program. The given recording medium may be an arbitrary recording medium that records the image processing program that can be read by the computer system 600, such as the CD-ROM 660, the USE memory 670, a portable physical medium (e.g., MO disk, DVD disk, flexible disk (FD), magnetooptical disk, or IC card), a stationary physical medium (e.g., HDD 614, RAM 612, or ROM 613) that is provided inside or outside the computer system 600, or a communication medium that temporarily stores a program during transmission (e.g., the public line N3 connected via the modem 650, or the local area network or the wide area network N1 to which the computer system (PC) 681 or the server 682 is connected).

Specifically, the image processing program is recorded on a recording medium (e.g., portable physical medium, stationary physical medium, or communication medium) so that the image processing program can be read by a computer. The computer system 600 implements the functions of the image processing device by reading the image processing program from such a recording medium, and executing the image processing program. Note that the image processing program need not necessarily be executed by the computer system 600. The invention may be similarly applied to the case where the computer system (PC) 681 or the server 682 executes the image processing program, or the computer system (PC) 681 and the server 682 execute the image processing program in cooperation.

An example in which the process performed by the output image generation section 340 (see FIG. 9) on the normal light image and the special light image acquired in advance is implemented by software is described below using a flowchart illustrated in FIG. 19.

In a step S11, header information (e.g., capture mode and illumination light synchronization signal) is input (added) to the normal light image and the special light image captured in time series. The special light image and the normal light image are input to an image buffer allocated in advance (S12). The candidate attention area is detected from the special light image (described in detail below with reference to FIG. 20) (S13).

The area of each candidate attention area is calculated as the reliability of each candidate attention area (S14). The attention area is selected within the special light image (second image) based on the candidate attention area detection result, and the visibility of the corresponding attention area within the normal light image (first image) that corresponds to the selected attention area is improved (display mode setting process) (described in detail below with reference to FIG. 21) (S15). The image signal for which the display mode has been determined is then output (S16). Whether or not the final image captured in time series has been processed is then determined (S17). When it has been determined that the final image has not been processed, the above process is performed on the next image (signal) (S12). When it has been determined that the final image (signal) has been processed, the process ends.

The details of the candidate attention area detection process (S13 in FIG. 19) are described below with reference to FIG. 20.

In a step S41, the special light image is divided into a plurality of areas. For example, the special light image is divided into a plurality of rectangular areas. The size of each rectangular area may be appropriately set. For example, each rectangular area includes 16×16 pixels. The local areas are then sequentially extracted, and the feature quantity that indicates the likelihood of a lesion is calculated (see the expressions (3) to (8)) (S42). The feature quantity of each local area is compared with a given threshold value, and each local area is classified into one of a plurality of groups corresponding to the comparison results (S43). An area that includes each local area that has been classified into at least one of a plurality of groups and a local area group adjacent thereto is detected as the candidate attention area (S44). Flag information that indicates whether or not the candidate attention area has been detected is then output (S45).

The details of the display mode setting process (S15 in FIG. 19) are described below with reference to FIG. 21.

In a step S31, the attention area is selected within the special light image (second image) based on the candidate attention area detection result and the reliability, and the processing process that improves the visibility of the corresponding attention area within the normal light image (first image) that corresponds to the selected attention area is performed (described in detail below with reference to FIG. 22). The display mode of the output image is then selected (S32). More specifically, the output image when the attention area has been detected within the special light image is selected. The output image when the attention area has been detected, is selected by the user in advance from the special light image and the normal light image processed in the step S31.

The details of the processing process (S31 in FIG. 21) are described below with reference to FIG. 22. In a step S51, the attention information that indicates the degree of attention is set corresponding to the detected candidate attention area. For example, the attention information (At) is set corresponding to each candidate attention area based on the group calculated in the step S13. The degree of attention At corresponding to each group is set as the look-up table AtLut(i) in advance.

The blending ratio of the pixel value within the attention area (special light image) and the pixel value within the corresponding attention area (normal light image) is then set corresponding to the attention information (S52). For example, the blending ratio alpha is calculated using the expression (9) based on the attention information (At) set in the step S51. Note that the blending ratio alpha is a value within the range from 0 to 1.

The attention area is extracted from the special light image that includes the detected candidate attention area based on the reliability, and the corresponding attention area is selected from the normal light image (S53). For example, the lookup table calLut(x, y) in which the position of each pixel within the normal light image is respectively linked to the position of each pixel within the special light image is generated in advance, and the coordinates (x', y') within the normal light image that correspond to the coordinates (x, y) of each pixel within the special light image are calculated. A candidate attention area having a reliability equal to or more than a preset threshold value is then extracted as the attention area. Note that a plurality of pixel positions may be present corresponding to the attention area. When the pixel position corresponding to the attention area is present between pixels, a known interpolation algorithm (e.g., linear interpolation) may be applied.

The corresponding attention area within the normal light image is then processed based on the attention area detection result (S54). For example, a blended image is generated from the special light image and the normal light image (see the expressions (11) and (12)).

The luminance of each pixel included in an area other than the corresponding attention area is then reduced (see the expression (13)) (S55).

The above process makes it possible to display the normal light image and the special light image as a single image. Therefore, it is possible to provide an endoscope system that prevents a situation in which a lesion area is missed while reducing the burden on the doctor.

According to the first embodiment, the first image acquisition section (normal light image acquisition section 320 in a narrow sense) acquires the first image (normal light image in a narrow sense) that corresponds to the wavelength band of white light, and the second image acquisition section (special light image acquisition section 330 in a narrow sense) acquires the second image (special light image (e.g., narrow-band image or fluorescent image) in a narrow sense) that corresponds to the specific wavelength band (the wavelength band of narrow-band light or fluorescence in a narrow sense). The candidate attention area detection section 341 sets the candidate attention area based on the feature quantity of the second image. The reliability calculation section 342 calculates the reliability, and the display mode setting section 343 sets the display mode of the output image within the attention area based on the calculated reliability.

The term "attention area" used herein refers to an area for which the observation priority for the user is relatively higher than that of other areas. For example, when the user is a doctor, and desires to perform treatment, the attention area refers to an area that includes a mucosal area or a lesion area. If the doctor desires to observe bubbles or feces, the attention area refers to an area that includes a bubble area or a feces area. Specifically, the attention area for the user differs depending on the objective of observation, but necessarily has an observation priority relatively higher than that of other areas. The term "candidate attention area" used herein refers to a candidate for the attention area. The term "reliability" used herein refers to a measure that indicates the likelihood that the candidate attention area is the attention area. For example, the area of the candidate attention area is used as the reliability.

The above configuration makes it possible to acquire the normal light image (white light image) and the special light image (e.g., narrow-band image or fluorescent image), and set the candidate attention area within the special light image. The visibility of the attention area can be improved while improving the accuracy of the attention area (e.g., accuracy when determining a lesion area as the attention area) as compared with the case where the reliability is not used, by setting the attention area from the candidate attention area based on the reliability, and setting the display mode within the attention area (e.g., bringing the color of the attention area closer to the target color). Therefore, when observing in vivo tissue using an endoscope by utilizing normal light and special light, for example, it is possible to accurately detect a lesion area (that is difficult to detect using normal light) using special light, and display an area including the lesion area with high visibility as compared with the case where the method according to the first embodiment is not used. Therefore, the burden on the doctor can be reduced while preventing a situation in which the lesion area is missed.

The display mode setting section 343 performs the display mode setting process that sets the corresponding attention area within the first image so that the corresponding attention area corresponds to the attention area within the second image, and improves the visibility of the corresponding attention area. The term "corresponding attention area" used herein refers to an area within the first image that is located at a position corresponding to that of the attention area within the second image. For example, when the first image and the second image differ in position due to the difference in imaging element, the corresponding attention area is set after performing an appropriate calibration process.

This makes it possible to set the corresponding attention area within the first image so that the corresponding attention area corresponds to the attention area set within the second image. For example, it is possible to appropriately determine the position within the first image that corresponds to the lesion area that has been detected using the special light image. A situation in which the corresponding attention area (i.e., lesion area) is missed can be prevented by improving the visibility of the corresponding attention area as compared with the first image that has not been processed.

The display mode setting section 343 includes the processing section 3431 that processes the first image based on the reliability and the candidate attention area information obtained from the second image, and sets the first image that has been processed by the processing section 3431 to be the output image.

This makes it possible to select an image obtained by processing the normal light image as the output image, for example. The normal light image may be processed so that the color of the attention area is brought closer to a given target color (see FIG. 26C), or the attention area is enclosed by an area in a given target color (see FIG. 26D), for example. This makes it possible to improve the visibility of the lesion area (i.e., prevent a situation in which the lesion area is missed) while reducing the burden on the doctor.

The processing section 3431 performs a processing process that improves the visibility of the corresponding attention area within the first image when the reliability is high. The degree of reliability may be determined by comparing the reliability with a given threshold value, for example.

A situation in which a lesion area is missed can be prevented when the reliability is high (e.g., when it is likely that the candidate attention area is a lesion area) since the visibility of the corresponding attention area within the first image is improved.

The processing section 3431 may perform a blending process on the first image and the second image as the processing process.

In this case, the visibility of the corresponding attention area within the first image can be improved by the blending process. More specifically, the normal light image and the special light image are blended.

The processing section 3431 may include the area selection section 34313. The area selection section 34313 may select the candidate attention area detected by the candidate attention area detection section 341 as the attention area based on the reliability.

This makes it possible to select the attention area from the candidate attention areas using the reliability as a measure. The area, the hue, the intensity, or the luminance of each area, a combination thereof, or the like may be used as the reliability. Therefore, the attention area can be selected from various viewpoints (e.g., area, hue, intensity, and luminance).

The reliability calculation section 342 may calculate the reliability based on the area of the candidate attention area.

In this case, since a candidate attention area having a large area is detected as the attention area, and a candidate attention area having a small area is not detected as the attention area, the effects of noise can be reduced.

The reliability calculation section 342 may calculate the reliability based on the feature quantity of each pixel within the candidate attention area.

This makes it possible to calculate the reliability from various viewpoints (e.g., hue, luminance, or intensity).

The candidate attention area detection section 341 may include the local area setting section 3411 that divides the second image into given local areas, and the feature quantity calculation section 3412 that calculates the feature quantity of each local area using each pixel within each local area, and may detect the candidate attention area based on the feature quantity of each local area.

Specifically, the candidate attention area detection section 341 calculates the feature quantity of each local area to detect the candidate attention area. For example, when a 16×16 pixel area (see FIG. 13) is used as the local area, the amount of calculations can be reduced as compared with the case of calculating the feature quantity of each pixel. Moreover, since a lesion smaller than the local area is rarely detected as the candidate attention area, the effects of noise can be reduced.

The candidate attention area detection section 341 may include the local area setting section 3411 that divides the first image into given local areas, and the feature quantity calculation section 3412 that calculates the feature quantity of each local area using each pixel within the second image that corresponds to each pixel within each local area, and may detect the candidate attention area from the first image.

This makes it possible to set the candidate attention area within the first image, so that the flexibility of the process can be improved.

The candidate attention area detection section 341 may include the classification section 3413 that compares the feature quantity of each local area with a given threshold value, and classifies each local area into one of a plurality of groups. The candidate attention area detection section 341 may detect an area that includes each local area that has been classified into at least one group and a local area group adjacent thereto as the candidate attention area.

This makes it possible to classify each local area into one of a plurality of groups, unite adjacent local areas, and then detect the candidate attention area. Moreover, since the candidate attention area can be classified using the group, different information can be set corresponding to each group, or a different process can be performed corresponding to each group.

The candidate attention area detection section 341 may detect the attention pixel based on the feature quantity of each pixel within the second image, and may detect an area that includes the detected attention pixel as the candidate attention area.

This makes it possible to perform the process on each pixel without setting the local area. In this case, the local area setting section 3411 may be omitted, or may be allowed to remain so that the process can be performed on each local area or each pixel. It may be considered that the local area setting section 3411 sets a 1×1 pixel local area when the process is performed on each pixel. The term "attention pixel" used herein refers to a pixel that requires attention (e.g., a pixel that is included within a lesion area or the like).

The candidate attention area may be an area that includes the attention pixel and the selected non-attention pixel. More specifically, the non-attention pixels may be selected to form a given figure (e.g., polygon, circle, ellipse, arc, trapezoid, or point-symmetrical or line-symmetrical figure).

This makes it possible to prevent a situation in which the shape of the candidate attention area becomes complex (i.e., improve visibility) even when the process is performed on each pixel. The term "non-attention pixel" refers to a pixel that is included in the second image, and has not been detected as the attention pixel. The term "selected non-attention pixel" refers to a pixel that has been selected from the non-attention pixels as a pixel that forms the candidate attention area.

The processing section 3431 may perform a blending process that improves the visibility of the corresponding attention area within the first image when the reliability is high. The degree of reliability may be determined by comparing the reliability with a given threshold value, for example.

According to the above configuration, a situation in which a lesion area is missed can be prevented when the reliability is high (e.g., when it is likely that the candidate attention area is a lesion area) since the visibility of the corresponding attention area within the first image is improved by the blending process, for example.

The processing section 3431 may include the area selection section 34313, and the area selection section 34313 may select the attention area from the candidate attention areas based on the reliability. The area selection section 34313 may select the corresponding attention area within the first image that corresponds to the selected attention area. The processing section 3431 may perform the blending process on the corresponding attention area.

This makes it possible to appropriately select the corresponding attention area. The blending process can be performed on an appropriate area (e.g., an area that has been detected as a lesion) by performing the blending process on the corresponding attention area, so that a situation in which a lesion area is missed can be prevented, for example.

The processing section 3431 may include the attention information setting section 34311 and the blending ratio setting section 34312. The attention information setting section 34311 may set the attention information that indicates the degree of attention corresponding to each candidate attention area. The blending ratio setting section 34312 may set the blending ratio of the first image and the second image. The processing section 3431 may perform the blending process based on the blending ratio that has been set by the blending ratio setting section 34312.

This makes it possible to change the blending ratio corresponding to the degree of attention. For example, the ratio of the special light image increases in a lesion area that requires considerable attention, and the ratio of the normal light image increases in a lesion area that requires less attention (see FIGS. 16A and 16B). For example, the ratio of brown increases in a lesion area (e.g., epidermoid cancer) that requires considerable attention. Therefore, the user can easily determine the lesion area that requires considerable attention.

The specific wavelength band may be a band that is narrower than the wavelength band of white light. Specifically, the first image and the second image may be an in vivo image, and the specific wavelength band may be the wavelength band of light absorbed by hemoglobin in blood, for example. More specifically, the specific wavelength band may be 390 to 445 nm or 530 to 550 nm.

This makes it possible to observe the structure of a surface area of in vivo tissue and a blood vessel located in a deep area. A lesion area (e.g., epidermoid cancer) that cannot be easily observed using non light can be displayed in brown or the like by inputting the resulting signal to a given channel (R, G, or B), so that the lesion area can be reliably detected (i.e., a situation in which the lesion area is missed can be prevented). A wavelength band of 390 to 445 nm or 530 to 550 nm is selected from the viewpoint of absorption by hemoglobin and the ability to reach a surface area or a deep area of in vivo tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach a surface area or a deep area of in vivo tissue (living body)).

The first embodiment may also be applied to an electronic apparatus that includes an image processing device (image processing section).

For example, the image processing device according to the first embodiment may be provided in various types of electronic apparatus (i.e., an apparatus that operates using a power source (e.g., voltage or current)), such as an endoscope, a digital camera, a digital video camera, and a personal computer.

The first embodiment may also be applied to an endoscope system that includes a first light source, a second light source, a first image acquisition section (normal light image acquisition section 320 in a narrow sense), a second image acquisition section (special light image acquisition section 330 in a narrow sense), the candidate attention area detection section 341, the reliability calculation section 342, the display mode setting section 343, and the display section 400. The first light source applies white light to an in vivo object, and the second light source applies light within a specific wavelength band (e.g., narrow-band light or excitation light that generates fluorescence) to the in vivo object. The first image acquisition section acquires an image that includes an object image including information within the wavelength band of white light applied by the first light source as a first in vivo image, and the second image acquisition section acquires an image that includes an object image including information within the specific wavelength band of light applied by the second light source as a second in vivo image. The candidate attention area detection section 341 detects the candidate attention area that is a candidate for the attention area based on the feature quantity of each pixel within the second in vivo image. The reliability calculation section 342 calculates the reliability that indicates the likelihood that the candidate attention area is the attention area. The display mode setting section 343 sets the display mode of the output image corresponding to the reliability. The display section 400 displays the output image according to the display mode that has been set by the display mode setting section 343.

According to the above configuration, an in vivo image captured using white light (white light source), and an in vivo image captured using light within the specific wavelength band, are obtained. The feature quantity of each pixel within the second in vivo image is calculated, and the candidate attention area that is a candidate for the attention area (e.g., lesion area) is detected. The attention area can be selected with high accuracy (i.e., an attention area that is likely to be a lesion area can be selected) by selecting the attention area from the candidate attention areas corresponding to the reliability calculated by the reliability calculation section 342, and the display mode of the output image can be set thereafter. It is possible to present information to the user (i.e., doctor) of the system by displaying the output image on the display section 400 according to the display mode that has been set by the display mode setting section 343.

The first embodiment may also be applied to an image processing device that includes a first image acquisition section, a second image acquisition section, an attention area detection section, and the display mode setting section 343. The first image acquisition section acquires a first image that is an image that includes an object image including information within the wavelength band of white light, and the second image acquisition section acquires a second image that is an image that includes an object image including information within a specific wavelength band. The candidate attention area detection section detects the attention area that is an area that requires attention based on the feature quantity of each pixel within the second image. The display mode setting section 343 displays the alert area in the corresponding attention area within the output image that corresponds to the detected attention area, the alert area indicating information about the attention area detection result.

According to the above configuration, the first image and the second image are acquired, and the attention area is detected from the second image based on the feature quantity of each pixel within the second image. The corresponding attention area that corresponds to the detected attention area is detected from the output image, and the alert area is displayed. This makes it possible to improve the visibility of the corresponding attention area that corresponds to the attention area (e.g., lesion area) as compared with the case of merely displaying the first image. Note that the alert area may be selected corresponding to the priority, or may be selected without taking account of the priority.

The first embodiment may also be applied to a program that causes a computer to function as a first image acquisition section, a second image acquisition section, the candidate attention area detection section 341, the reliability calculation section 342, and the display mode setting section 343. The first image acquisition section acquires a first image that is an image that includes an object image including information within the wavelength band of white light, and the second image acquisition section acquires a second image that is an image that includes an object image including information within the specific wavelength band. The candidate attention area detection section 341 detects the candidate attention area from the second image based on the feature quantity of each pixel within the second image. The reliability calculation section 342 calculates the reliability that indicates the likelihood that the candidate attention area is the attention area. The display mode setting section 343 sets the display mode of the output image corresponding to the reliability.

This makes it possible to store image data in advance (e.g., capsule endoscope), and process the stored image data by software using a computer system (e.g., PC).

The first embodiment may also be applied to a program that causes a computer to function as a first image acquisition section, a second image acquisition section, an attention area detection section, and the display mode setting section 343. The first image acquisition section acquires a first image that is an image that includes an object image including information within the wavelength band of white light, and the second image acquisition section acquires a second image that is an image that includes an object image including information within a specific wavelength band. The candidate attention area detection section detects the attention area that is an area that requires attention based on the feature quantity of each pixel within the second image. The display mode setting section 343 displays the alert area in the corresponding attention area within the output image that corresponds to the detected attention area, the alert area indicating information about the attention area detection result.

This makes it possible to store image data in advance (e.g., capsule endoscope), and process the stored image data by software using a computer system (e.g., PC).

The first embodiment may also be also be applied to a computer program product that stores a program code that implements each section (e.g., first image acquisition section, second image acquisition section, candidate attention area detection section, reliability calculation section, display mode setting section, and processing section) according to the first embodiment.

The program code implements a first image acquisition section that acquires a first image that is an image that includes an object image including information within the wavelength band of white light, a second image acquisition section that acquires a second image that is an image that includes an object image including information within a specific wavelength band, a candidate attention area detection section that detects the candidate attention area from the second image based on the feature quantity of each pixel within the second image, and a display mode setting section that sets the display mode of the output image corresponding to the calculated reliability.

The term "computer program product" used herein refers to an information storage medium, a device, an instrument, a system, or the like that stores a program code, such as an information storage medium (e.g., optical disk medium (e.g., DVD), hard disk medium, and memory medium) that stores a program code, a computer that stores a program code, or an Internet system (e.g., a system including a server and a client terminal), for example. In this case, each element and each process according to the first embodiment are implemented by corresponding modules, and a program code that includes these modules is recorded (stored) in the computer program product.

3. Second Embodiment

A second embodiment of the invention is described below. The second embodiment differs from the first embodiment as to the configuration of the candidate attention area detection section 341 and the configuration of the processing section 3431.

Figure 23:
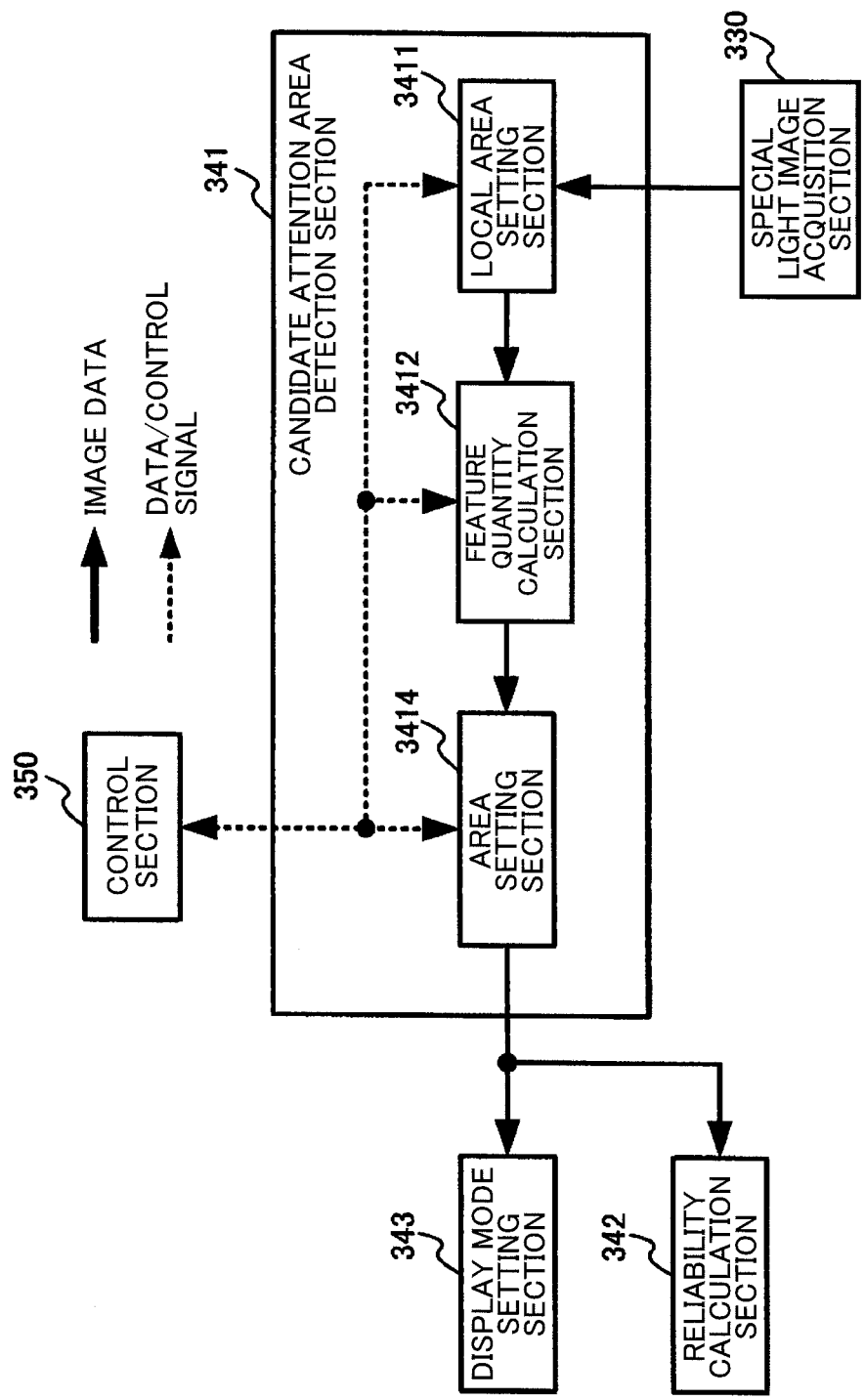
FIG. 23 illustrates another configuration example of a candidate attention area detection section.

The candidate attention area detection section 341 detects the candidate attention area (i.e., a candidate for an attention area) from the special light image under control of the control section 350. The configuration of the candidate attention area detection section 341 is described below. FIG. 23 is a block diagram illustrating an example of the configuration of the candidate attention area detection section 341 according to the second embodiment. As illustrated in FIG. 23, the candidate attention area detection section 341 includes a local area setting section 3411, a feature quantity calculation section 3412, and an area setting section 3414. The special light image acquisition section 330 is connected to the local area setting section 3411. The local area setting section 3411 is connected to the feature quantity calculation section 3412. The feature quantity calculation section 3412 is connected to the area setting section 3414. The area setting section 3414 is connected to the reliability calculation section 342 and the display mode setting section 343. The control section 350 is bidirectionally connected to the local area setting section 3411, the feature quantity calculation section 3412, and the area setting section 3414, and controls the local area setting section 3411, the feature quantity calculation section 3412, and the area setting section 3414.

The local area setting section 3411 sets a plurality of local areas within the special light image in the same manner as in the first embodiment.

The feature quantity calculation section 3412 calculates the feature quantity of each local area. For example, the feature quantity calculation section 3412 calculates the hue in the same manner as in the first embodiment.

The area setting section 3414 performs a threshold process using the hue H of each local area that has been calculated as described above, and sets a candidate attention area. When it is desired to set a brown area as the attention area, a local area having a hue H within the range of 5 to 35 is extracted, for example.

The area setting section 3414 unites extracted local areas that are adjacent to each other, and sets each area obtained by the above process as the candidate attention area. Note that the candidate attention area may be one local area. The area setting section 3414 calculates the position of each pixel included in the candidate attention area using the coordinates of each local area a(m, n) included in the candidate attention area and information about each pixel included in each local area, and outputs the calculated position of each pixel to the reliability calculation section 342 and the display mode setting section 343 as candidate attention area information.

Figure 15B:
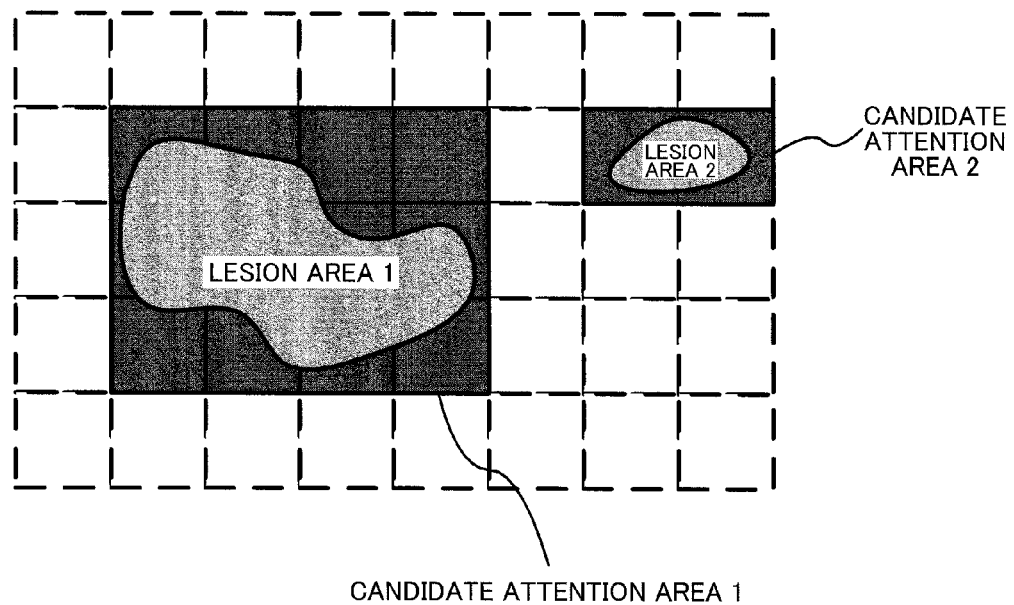

The area setting section 3414 may reset the candidate attention area information so that attention area information that indicates an arbitrary shape (e.g., polygon or circle) is output. FIGS. 15A and 15B illustrate an example in which the area setting section 3414 resets the candidate attention area information. FIGS. 15A and 15B illustrate the special light image. Each area enclosed by a dotted line indicates the local area. When it is desired that the candidate attention area information that corresponds to a candidate attention area 1 (see FIG. 15A) indicate a rectangular shape, the position of each pixel included in the candidate attention area 1 is calculated from the coordinates a(m, n) of each local area that belongs to the candidate attention area 1 and information about the pixels included in each local area, A rectangle that is circumscribed to the pixels is set as the candidate attention area, and the position of each pixel included in the candidate attention area is calculated, and output as the candidate attention area information that corresponds to the candidate attention area 1. The shape of the candidate attention area can thus be changed to a shape that can be easily observed (see FIG. 15B). This prevents a situation in which the candidate attention area has a complex shape (i.e., visibility can be improved).

The area setting section 3414 may calculate the average luminance or intensity (saturation) of each local area by a known method instead of calculating the hue H, and may detect the candidate attention area using the average luminance or intensity as the feature quantity. The area setting section 3414 may calculate one feature quantity by arbitrarily combining the luminance information, the hue information, and the intensity information to detect the candidate attention area.

Figure 24:
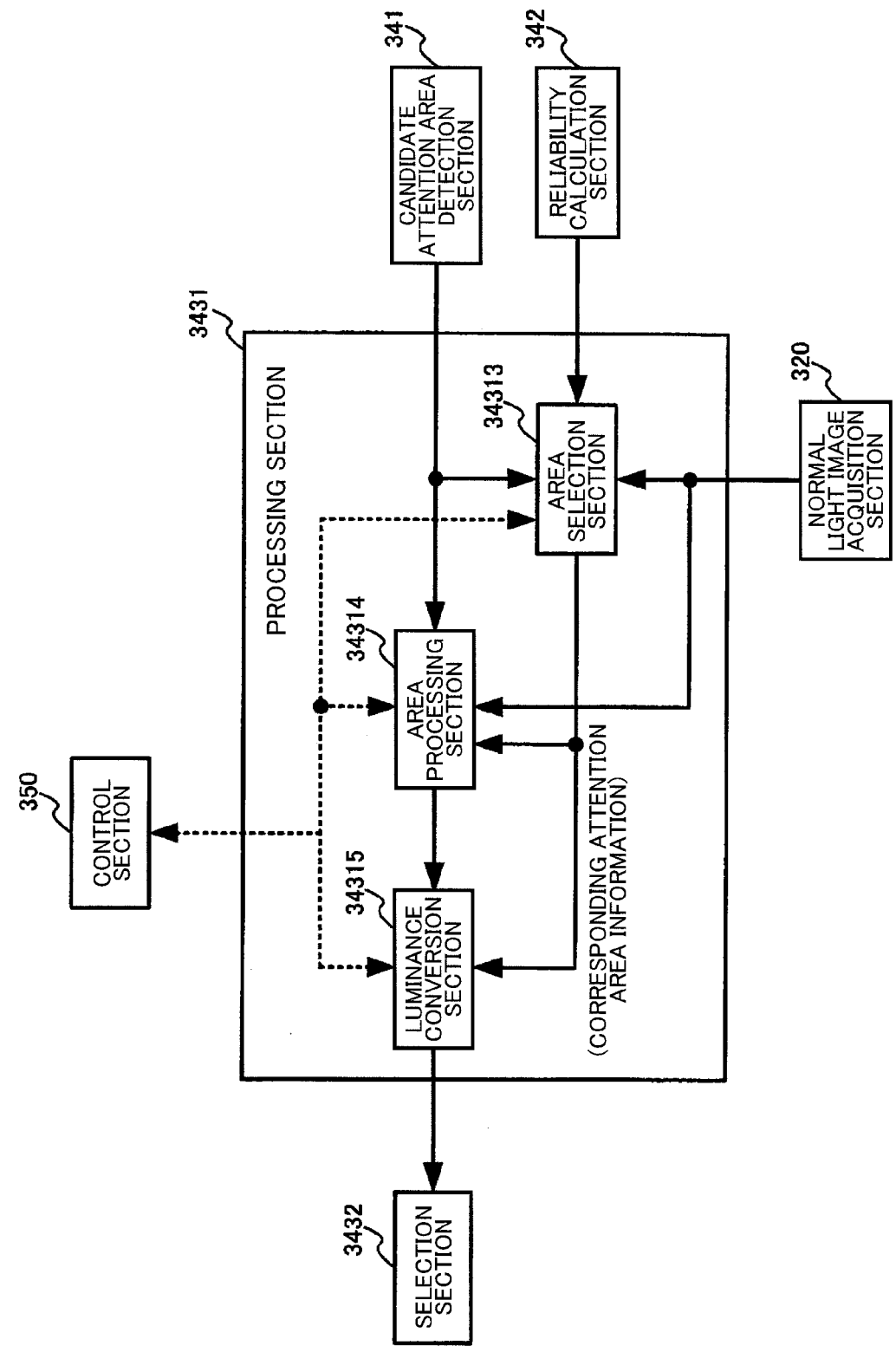
FIG. 24 illustrates another configuration example of a processing section.

The configuration of the processing section 3431 is described below. FIG. 24 is a block diagram illustrating an example of the configuration of the processing section 3431 according to the second embodiment. As illustrated in FIG. 24, the processing section 3431 includes an area selection section 34313, an area processing section 34314, and a luminance conversion section 34315.

The area selection section 34313 selects the attention area based on the candidate attention area information input from the candidate attention area detection section 341, and the reliability input from the reliability calculation section 342. More specifically, the area selection section 34313 extracts a candidate attention area having a reliability equal to or more than a preset threshold value from a plurality of candidate attention areas. For example, when the area selection section 34313 detects a candidate attention area having a reliability of "1" as the attention area, only the local areas that belong to the candidate attention area 1 (see FIG. 15A) are detected as the attention area. This makes it possible to exclude a candidate attention area having a small area as noise, and select an attention area having high reliability. The area selection section 34313 sets an area within the first image that corresponds to the selected attention area to be the corresponding attention area, and outputs information about each pixel within the corresponding attention area as corresponding attention area information.

The area processing section 34314 performs a color conversion process on each pixel that is included in the normal light image and is indicated by (input as) the corresponding attention area information using the following expressions (14) to (16), for example. Note that r(x, y), g(x, y), and b(x, y) are the signal values of the R, G, and B channels at the coordinates (x, y) of the normal light image before the color conversion process is performed, and r_out (x, y), g_out(x, y), and b_out(x, y) are the signal values of the R, G, and B channels at the coordinates (x, y) of the normal light image after the color conversion process has been performed. T_r, T_g, and T_b are R, G, and B signal values of an arbitrary target color, and gain is an arbitrary coefficient from 0 to 1.

$$r\_out(x,y) = \text{gain} * r(x,y) + (1-\text{gain}) * T\_r \quad (14)$$

$$g\_out(x,y) = \text{gain} * g(x,y) + (1-\text{gain}) * T\_g \quad (15)$$

$$b\_out(x,y) = \text{gain} * b(x,y) + (1-\text{gain}) * T\_b \quad (16)$$

Figure 26A:
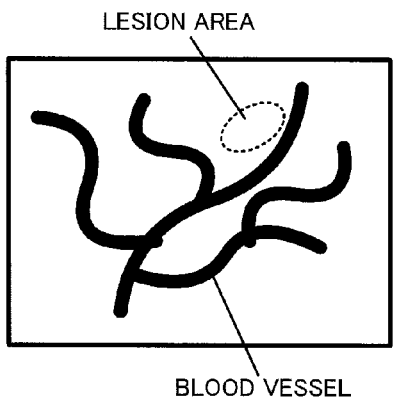
FIG. 26A illustrates an example of a normal light image.
Figure 26B:
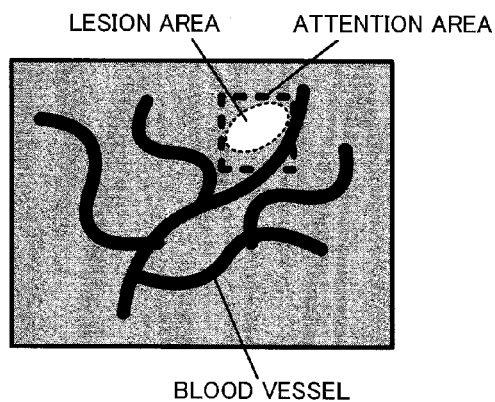
FIG. 26B illustrates an example of a special light image.
Figure 26C:
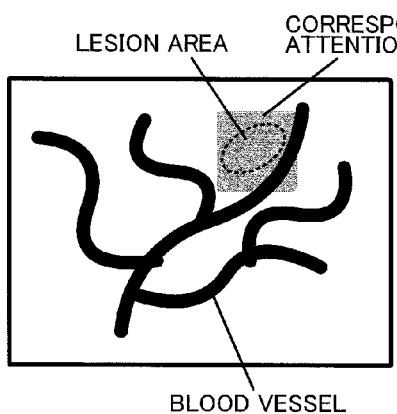
FIGS. 26C, 26D, 26E, and 26F illustrate examples of an output image.

The above color conversion process allows the attention area that is suspected to be a lesion area when observing the special light image illustrated in FIG. 26B to be displayed within the normal light image as an area in a different color (see FIG. 26C). This makes it possible to prevent a situation in which a lesion area is missed while reducing the burden on the doctor during a diagnosis that utilizes the normal light image and the special light image.

The area processing section 34314 may perform a color conversion process on each pixel that is included in the normal light image and forms the boundary of (with) the corresponding attention area using the following expressions (17) to (19), for example.

$$r\_out(x,y)=T\_r \quad (17)$$

$$g\_out(x,y)=T\_g \quad (18)$$

$$b\_out(x,y)=T\_b \quad (19)$$

Figure 26D:
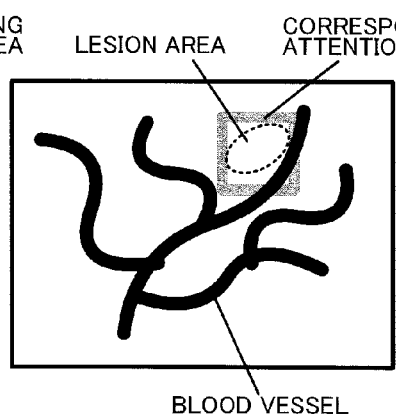

This makes it possible to display the corresponding attention area within the normal light image as an area that is enclosed by an area in an arbitrary target color (see FIG. 26D).

The luminance conversion section 34315 may perform a luminance conversion process on each pixel that is included in the normal light image and is not included in the corresponding attention area using the following expressions (20) to (22), for example.

$$r\_out(x,y)=gain*r(x,y) \quad (20)$$

$$g\_out(x,y)=gain*g(x,y) \quad (21)$$

$$b\_out(x,y)=gain*b(x,y) \quad (22)$$

This makes it possible to darken an area within the normal light image that is other than the corresponding attention area (see FIG. 26E) (i.e., the corresponding attention area can be displayed as a relatively bright area).

Figure 25:
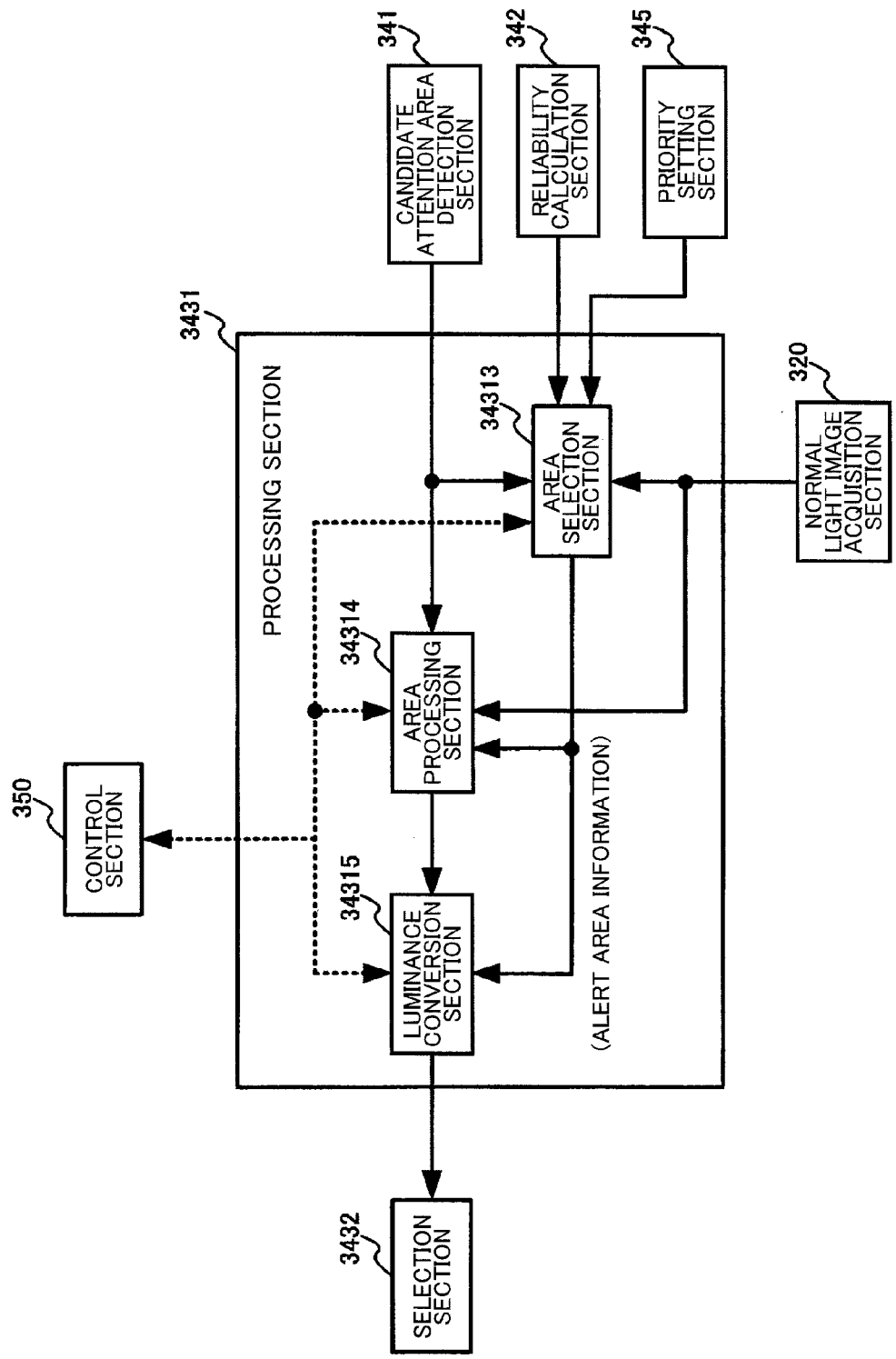
FIG. 25 illustrates another configuration example of a processing section.

The configuration of the processing section 3431 when setting the alert area based on the priority is described below. FIG. 25 is a block diagram illustrating an example of the configuration of the processing section 3431 when setting the alert area. As illustrated in FIG. 25, the processing section 3431 includes an area selection section 34313, an area processing section 34314, and a luminance conversion section 34315.

The area selection section 34313 selects the attention area based on the candidate attention area information input from the candidate attention area detection section 341, and the reliability input from the reliability calculation section 342. The area selection section 34313 sets an area within the first image that corresponds to the selected attention area to be the corresponding attention area. The area selection section 34313 sets an alert area based on the attention area and the priority input from the priority setting section 345 (not illustrated in FIG. 9) that is included in the output image generation section 340. The area selection section 34313 outputs information about each pixel within the alert area as alert area information.

The term "priority" used herein refers to a display priority. For example, the priority is set based on the reliability, the feature quantity of each pixel, the degree of attention, and the like. Note that the term "degree of attention" refers to information such as the information set by the attention information setting section 34311 (refer to the first embodiment).

The area selection section 34313 stores information about the upper limit of the number of alert areas. The area selection section 34313 does not further set the alert area when it is predicted that the number of alert areas exceeds the upper limit. This prevents a situation in which many alert areas that are difficult for the doctor to observe at one time are displayed on the screen.

The area processing section 34314 performs the above color conversion process (see the expressions (14) to (19)). The area processing section 34314 stores information about the processing priority assigned to each alert area. When a plurality of alert areas are present, the area processing section 34314 sequentially processes each alert area in order from an alert area having a higher processing priority.

Note that the processing section 3431 may process the corresponding attention area within the normal light image using an arbitrary luminance conversion process or color conversion process.

The processing section 3431 may display the attention area within the special light image in the vicinity of the normal light image (see FIG. 26F) instead of performing the luminance conversion process or the color conversion process on the corresponding attention area within the normal light image. The processing section 3431 may display the attention area within the special light image instead of the corresponding attention area within the normal light image.

Note that each section of the image processing section 300 need not necessarily be implemented by hardware. For example, a CPU may perform the process of each section on an image acquired using an imaging apparatus such as a capsule endoscope. Specifically, the process of each section may be implemented by software by causing the CPU to execute a program. Alternatively, the process of each section may partially be implemented by software.

Figure 19:
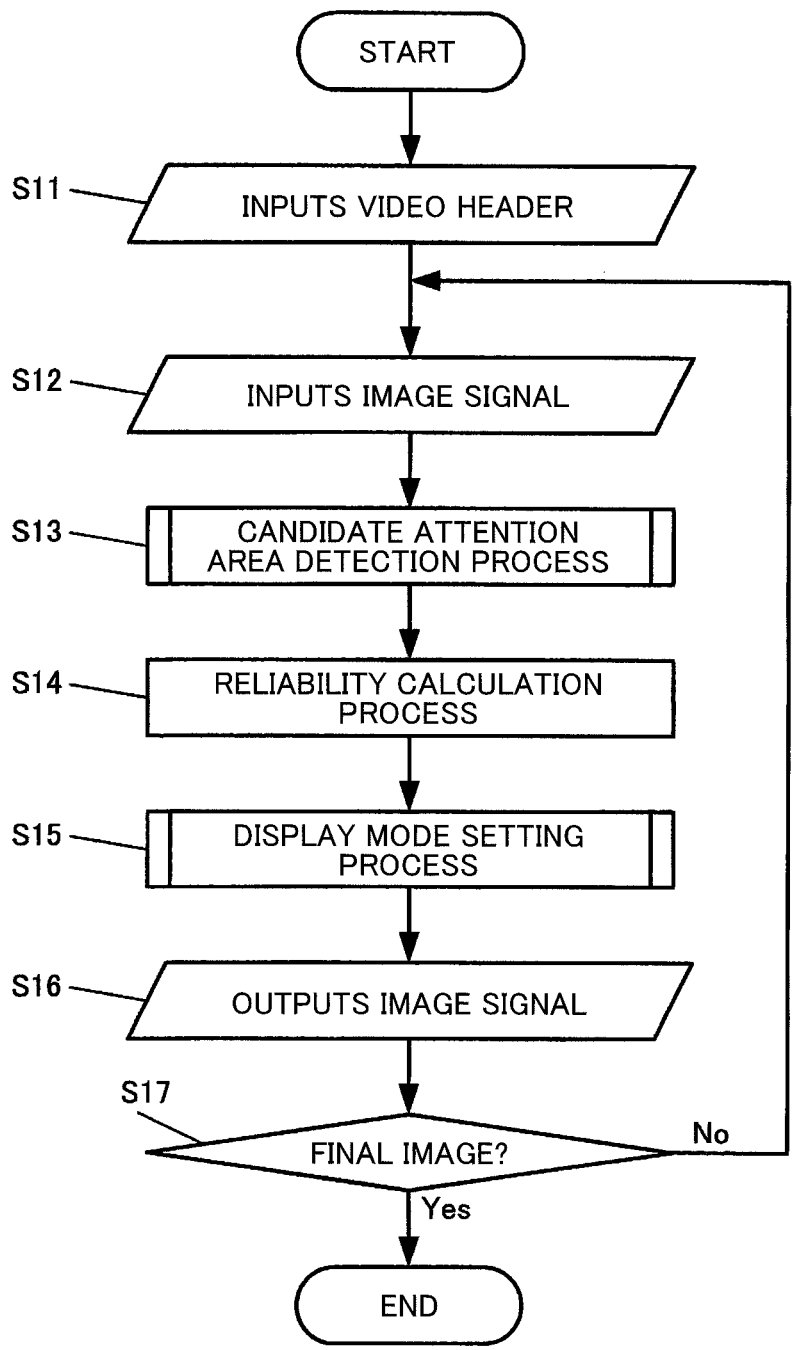
FIG. 19 is a flowchart illustrating a process according to one embodiment of the invention.
Figure 20:
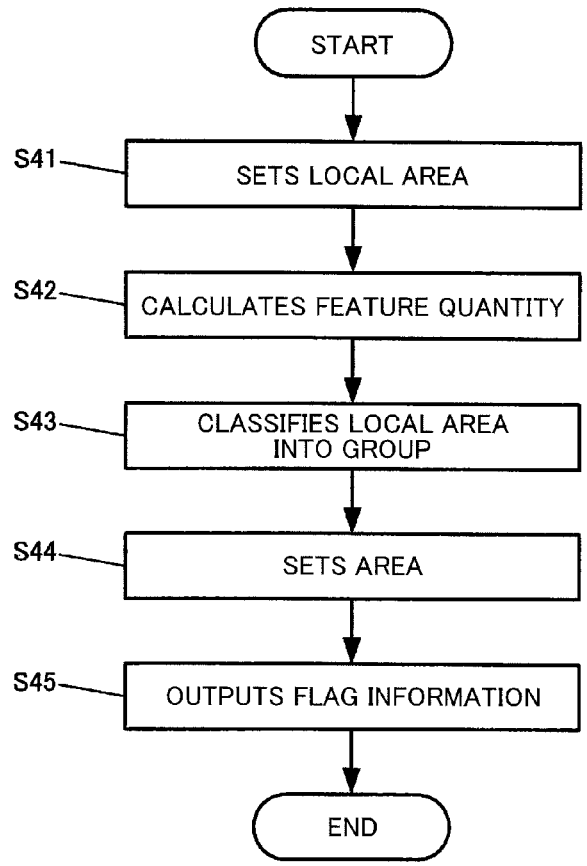
FIG. 20 is a flowchart illustrating a candidate attention area detection process.
Figure 21:
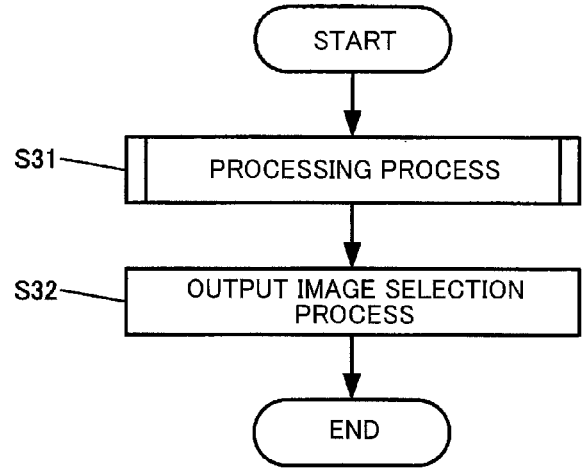
FIG. 21 is a flowchart illustrating a display mode setting process.

In this case, the process is performed in the same as in the first embodiment except for the candidate attention area detection step (S13) in FIG. 19 and the processing step (S31) in FIG. 21.

Figure 27:
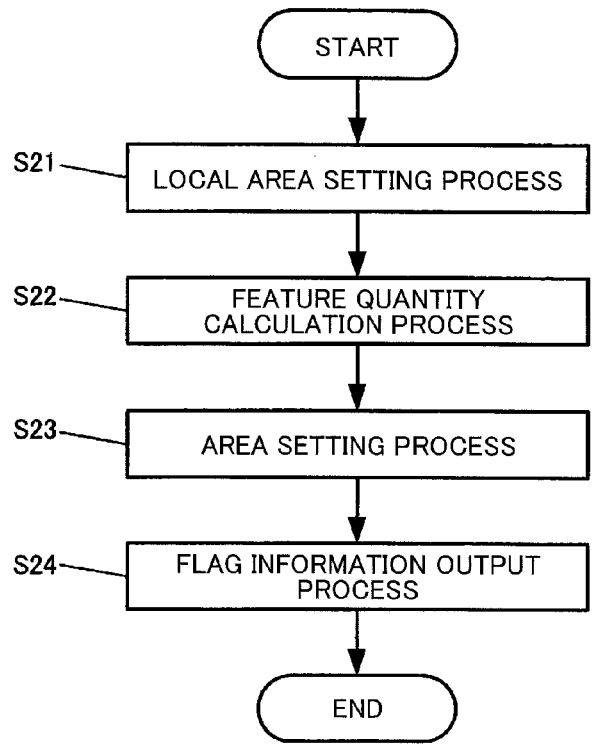
FIG. 27 is another flowchart illustrating a candidate attention area detection process.

The details of the candidate attention area detection process (S13 in FIG. 19) are described below with reference to FIG. 27. In a step S21, the special light image (second image) is divided into a plurality of local areas. For example, the special light image is divided into a plurality of rectangular areas. The size of each rectangular area may be appropriately set. For example, each rectangular area includes 16×16 pixels.

The local areas are then sequentially extracted, and the feature quantity that indicates the likelihood of a lesion is calculated (see the expressions (3) to (8)) (S22).

The feature quantity of each local area is compared with a given threshold value, and a local area that satisfies the threshold value condition is extracted. When adjacent local areas satisfy the threshold value condition, the adjacent local areas are united to form a local area group, and an area that includes the local area group (or one local area) is detected as the candidate attention area (S23). Flag information that indicates whether or not the candidate attention area has been detected is then output (S24).

The details of the processing process (S31 in FIG. 21) are described below with reference to FIG. 28. In a step S33, a candidate attention area having a reliability higher than a given threshold value is selected as the attention area from the detected candidate attention areas, and the corresponding attention area that corresponds to the selected attention area is extracted from the normal light image.

The visibility of the corresponding attention area within the normal light image that corresponds to the detected attention area within the special light image is improved based on the attention area detection result. For example, the color of the entire corresponding attention area may be brought closer to a given target color (see the expressions (14) to (16)), or the corresponding attention area may be enclosed by an area in a given target color (see the expressions (17) to (19)) (S34).

The luminance of each pixel included in an area other than the corresponding attention area may be reduced (see the expressions (20) to (22)) (S35).

The above process allows the attention area that is suspected to be a lesion area when observing the special light image illustrated in FIG. 26B to be displayed within the normal light image as an area in a different color (see FIG. 26C). An area other than the alert area is displayed more darkly (see FIG. 26E) when the process in the step S35 is performed. This makes it possible to prevent a situation in which a lesion area is missed, while reducing the burden on the doctor, during a diagnosis using the normal light image and the special light image.

An example in which the alert area is set based on the priority during the processing process (S31 in FIG. 21) is described below with reference to FIG. 29. In a step S36, a candidate attention area having a reliability higher than a given threshold value is selected as the attention area from the detected candidate attention areas, and the corresponding attention area that corresponds to the selected attention area is extracted from the normal light image. The extracted attention area is then extracted in descending order of priority. The number of attention areas to be extracted is set by the user in advance. The extracted attention area is set as the alert area (S37). The color conversion process in a step S38 is the same as the color conversion process in the step S34 in FIG. 28, and the luminance conversion process in a step S39 is the same as the luminance conversion process in the step S35 in FIG. 28.

According to the second embodiment, the processing section 3431 performs the conversion process as the processing process.

In this case, the visibility of the corresponding attention area within the first image can be improved by the conversion process. Examples of the conversion process include a color conversion process and a luminance conversion process. The details thereof are described later.

The processing section 3431 may perform a process that links the image of the attention area to the first image as the processing process.

In this case, the visibility of the corresponding attention area within the first image can be improved by the link process. Note that the process that links the image of the attention area to the first image may be implemented by displaying the image of the attention area in the vicinity of the first image, or replacing the image of the corresponding attention area within the first image with the image of the attention area within the second image, for example. The details thereof are described later.

The area selection section 34313 may select the attention area as the alert area based on the priority.

This makes it possible to select the alert area from a viewpoint other than the reliability, or select the alert area from an identical viewpoint (i.e., an area that is more appropriate for the objective can be selected).

The priority may be set using at least one piece of information selected from the reliability, the feature quantity of each pixel, and the degree of attention.

In this case, an area can be selected using the reliability, the feature quantity (e.g., intensity or luminance) of each pixel, or the degree of attention (the details of the degree of attention are described later in connection with an attention information setting section 34311) as a measure (i.e., an area can be selected from various viewpoints).

The area selection section 34313 may store information about the upper limit of the number of alert areas, and may not further set the attention area as the alert area when it is predicted that the number of alert areas exceeds the upper limit.

This prevents a situation in which the alert areas are displayed in a number that exceeds a desired number (e.g., the number of alert areas displayed is so large that the doctor cannot observe (determine) the alert areas at one time), so that smooth diagnosis, treatment, or the like can be implemented.

The processing section 3431 includes the area processing section 34314. The area processing section 34314 may store information about the processing priority assigned to each alert area, and may sequentially process each alert area in order from an alert area having a higher processing priority.

In this case, since the processing process is performed in order from an area having a higher processing priority (i.e., such an area is likely to be a lesion, or may be a serious lesion), efficient diagnosis or treatment can be implemented.

The processing section 3431 may perform the color conversion process that improves the visibility of the corresponding attention area within the first image when the reliability is high. The degree of reliability may be determined by comparing the reliability with a given threshold value, for example.

According to the above configuration, a situation in which a lesion area is missed can be prevented when the reliability is high (e.g., when it is likely that the candidate attention area is a lesion area) since the visibility of the corresponding attention area within the first image is improved by the color conversion process.

The processing section 3431 may include the area selection section 34313, and the area selection section 34313 may select the attention area from the candidate attention areas based on the reliability. The area selection section 34313 may select the corresponding attention area within the first image that corresponds to the selected attention area. The processing section 3431 may perform the color conversion process on the corresponding attention area.

This makes it possible to appropriately select the corresponding attention area. The color conversion process can be performed on an appropriate area (e.g., an area that has been detected as a lesion) by performing the color conversion process on the corresponding attention area, so that a situation in which a lesion area is missed can be prevented, for example.

The processing section 3431 may perform the color conversion process by weighting the color of each pixel included in the corresponding attention area with the target color.

This makes it possible to cause each pixel within the corresponding attention area to become translucent (see FIG. 26C), so that a situation in which a lesion area is missed can be prevented due to an improvement in visibility, for example.

The processing section 3431 may perform the color conversion process by changing the color of each pixel that is positioned in the periphery of the corresponding attention area to the target color.

This makes it possible to enclose the corresponding attention area with an area in the target color (see FIG. 26D), so that a situation in which a lesion area is missed can be prevented due to an improvement in visibility, for example.

The processing section 3431 may perform the luminance conversion process that improves the visibility of the corresponding attention area within the first image when the reliability is high. The degree of reliability may be determined by comparing the reliability with a given threshold value, for example.

According to the above configuration, a situation in which a lesion area is missed can be prevented when the reliability is high (e.g., when it is likely that the candidate attention area is a lesion area) since the visibility of the corresponding attention area within the first image is improved by the luminance conversion process, for example. For example, the corresponding attention area further stands out as a result of performing the luminance conversion process that improves the visibility of the corresponding attention area within the first image on the blended image (refer to the first embodiment).

The processing section 3431 may include the area selection section 34313, and the area selection section 34313 may select the attention area from the candidate attention areas based on the reliability. The area selection section 34313 may select the corresponding attention area within the first image that corresponds to the selected attention area. The processing section 3431 may perform the luminance conversion process on the corresponding attention area.

This makes it possible to appropriately select the corresponding attention area. The luminance conversion process can be performed on an area other than an appropriate area (e.g., an area that has been detected as a lesion) by performing the luminance conversion process on an area other than the corresponding attention area, so that a situation in which a lesion area is missed can be prevented, for example. For example, the corresponding attention area further stands out as a result of performing the luminance conversion process on an area of the blended image (refer to the first embodiment) other than the corresponding attention area.

The processing section 3431 may perform the luminance conversion process by reducing the luminance of each pixel that is included in an area other than the corresponding attention area.

Figure 26E:
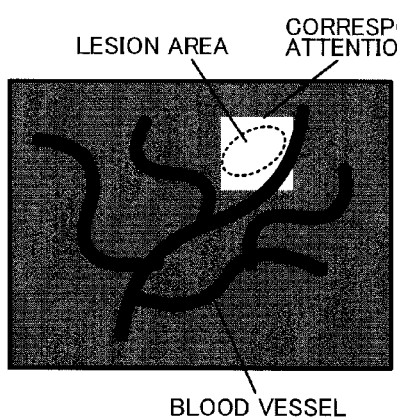

In this case, the luminance of an area other the corresponding attention area is reduced (i.e., an area other the corresponding attention area is displayed more darkly) (see FIG. 26E). Therefore, since the corresponding attention area is displayed more brightly (i.e., stands out), a situation in which the lesion area is missed can be prevented.

The processing section 3431 may perform a process that improves the visibility of the corresponding attention area within the first image when the reliability is high. The processing section 3431 may perform a process that links the image of the candidate attention area within the second image to the first image as the process that improves the visibility of the corresponding attention area within the first image. The degree of reliability may be determined by comparing the reliability with a given threshold value, for example.

According to the above configuration, a situation in which a lesion area is missed can be prevented when the reliability is high (e.g., when it is likely that the candidate attention area is a lesion area) since the image of the candidate attention area is linked to the first image as the process that improves the visibility of the corresponding attention area within the first image, for example. The details of the link process are described later.

The processing section 3431 may include the area selection section 34313, and the area selection section 34313 may select the attention area from the candidate attention areas based on the reliability. The area selection section 34313 may select the corresponding attention area within the first image that corresponds to the selected attention area. The processing section 3431 may display the image of the attention area in the vicinity of the first image as a process that links the image of the attention area to the first image.

Figure 26F:
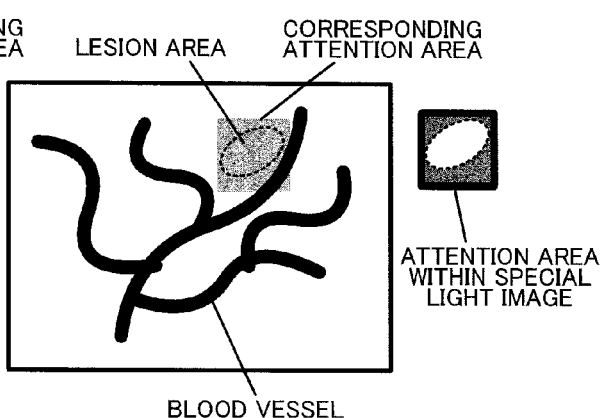

This makes it possible to display the output image as illustrated in FIG. 26F. In this case, the burden on the doctor when the doctor observes the output image is expected to be reduced as compared with the case where the first image and the second image are merely displayed side by side, for example. Moreover, since the image of the lesion area is displayed in the vicinity of the image of the attention area, a situation in which the lesion area is missed can be prevented.

The processing section 3431 may include the area selection section 34313, and the area selection section 34313 may select the attention area from the candidate attention areas based on the reliability. The area selection section 34313 may select the corresponding attention area within the first image that corresponds to the selected attention area. The processing section 3431 may replace the image of the corresponding attention area with the image of the attention area as a process that links the image of the attention area to the first image.

This makes it possible to display the output image in a state in which the image of the attention area within the second image is fitted into (incorporated in) the first image. This also makes it possible to observe the attention area (e.g., lesion area) with the second image (i.e., a special light image that allows easy observation of a lesion area), and observe the remaining area with the first image (i.e., a normal light image that is bright and easy to observe), so that a situation in which a lesion area is missed can be prevented, for example.

4. Third Embodiment

An endoscope system according to a third embodiment of the invention is described below. The third embodiment differs from the second embodiment as to the configuration of the candidate attention area detection section 341 and the configuration of the processing section 3431.

The configuration of the candidate attention area detection section 341 according to the third embodiment is described below. FIG. 10 is a block diagram illustrating an example of the configuration of the candidate attention area detection section 341 according to the third embodiment.

The local area setting section 3411 sets a plurality of local areas in the special light image in the same manner as in the second embodiment. The feature quantity calculation section 3412 calculates the feature quantity of each local area in the same manner as in the second embodiment. In the third embodiment, the hue $H(n)$ is used as the feature quantity.

The classification section 3413 compares the feature quantity $H(m)$ of each local area with a given threshold value under control of the control section 350, and classifies each local area into one of a plurality of groups corresponding to the comparison results. The classification section 3413 uses a plurality of threshold values $Thi$ ($i=0, 1, \ldots$, and L) that are set in advance, and classifies the local area $a(m, n)$ into a group i when the hue $H(m, n)$ is equal to or larger than $Thi$ and less than $Thi+1$. The classification section 3413 thus classifies each local area into one of groups 0 to $(L-1)$. The user may set the threshold value $Thi$ to an arbitrary value, or the threshold value $Thi$ may be automatically set to a value determined by the control section 350 in advance. The threshold value $Thi$ may also be adaptively set based on the position within the special light image. Local area information about each local area that has been classified into one of a plurality of groups is output to the area setting section 3414.

The area setting section 3414 detects the candidate attention area corresponding to the degree of attention. For example, the area setting section 3414 detects a plurality of local areas that have been classified into a group a by the classification section 3413 as a candidate attention area at an attention level a, and detects a plurality of local areas that have been classified into a group b by the classification section 3413 as a candidate attention area at an attention level b (a and b are arbitrary constants from 0 to L−1 (a≠b)). The area setting section 3414 calculates the position of each pixel included in the candidate attention area from the coordinates of each local area a(m, n) detected as the candidate attention area at each attention level and information about the pixels included in each local area, and outputs the calculated position of each pixel to the reliability calculation section 342 and the display mode setting section 343 as candidate attention area information at each attention level. The area setting section 3414 also outputs a control signal that indicates whether or not the candidate attention area has been detected within the special light image to the display mode setting section 343.

Note that the degree of attention may be set using an arbitrary number of attention levels instead of using the attention levels a and b.

The area setting section 3414 may set a new candidate attention area (e.g., set a rectangular candidate attention area in order to improve visibility) (refer to the second embodiment) corresponding to a plurality of local areas that have been detected as the candidate attention area at each attention level.

Figure 30:
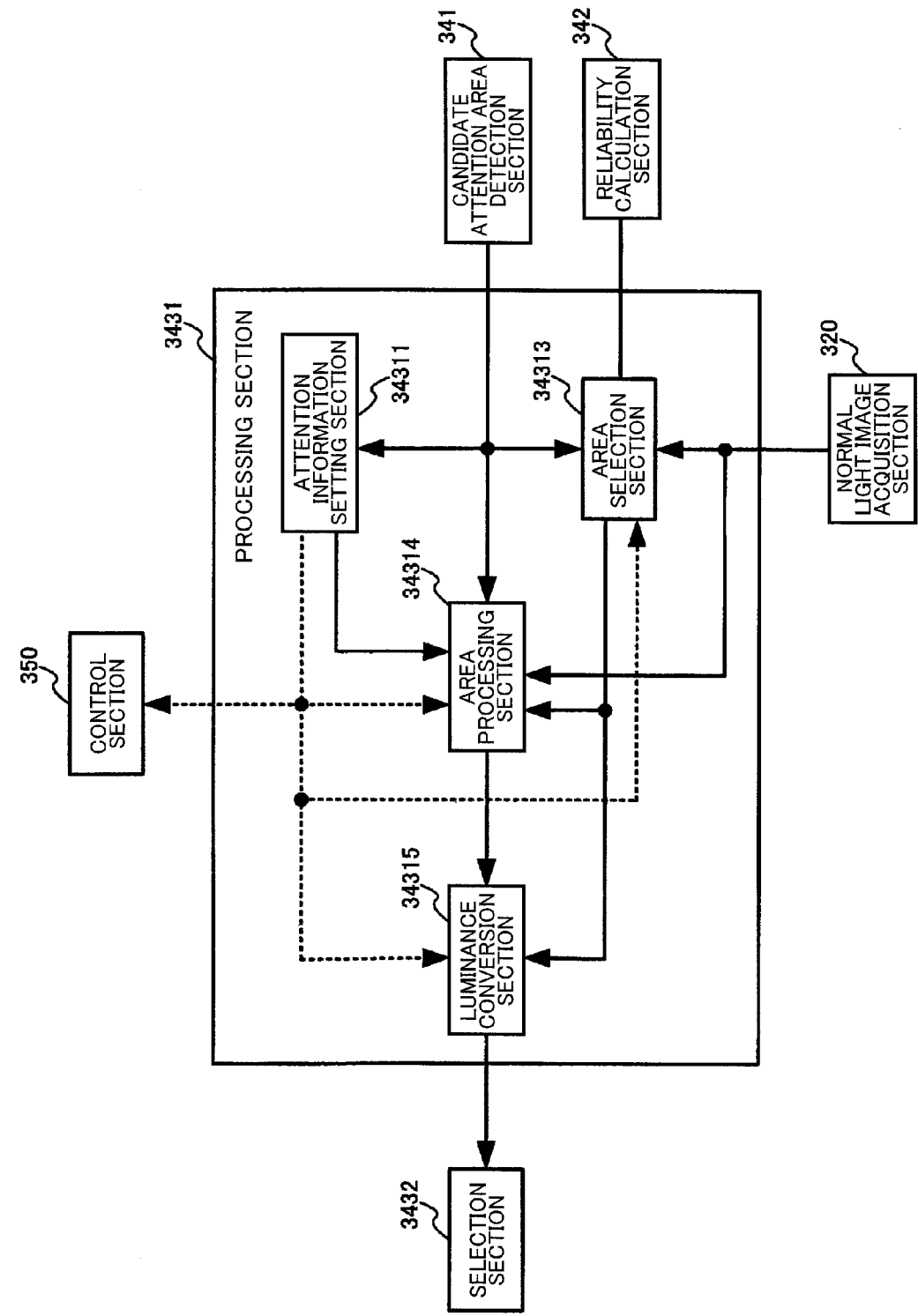
FIG. 30 illustrates another configuration example of a processing section.

The configuration of the processing section 3431 according to the third embodiment is described below. FIG. 30 is a block diagram illustrating an example of the configuration of the processing section 3431 according to the third embodiment. As illustrated in FIG. 30, the processing section 3431 includes an attention information setting section 34311, an area selection section 34313, an area processing section 34314, and a luminance conversion section 34315.

The attention information setting section 34311 sets attention information that indicates the degree of attention corresponding to each candidate attention area. For example, the degree of attention may be set to "a" when the candidate attention area belongs to the group a, and may be set to "b" when the candidate attention area belongs to the group b. Alternatively, the degree of attention may be set to "5" when the lesion is cancer, and may be set to "1" when the lesion is inflammation.

Figure 31B:
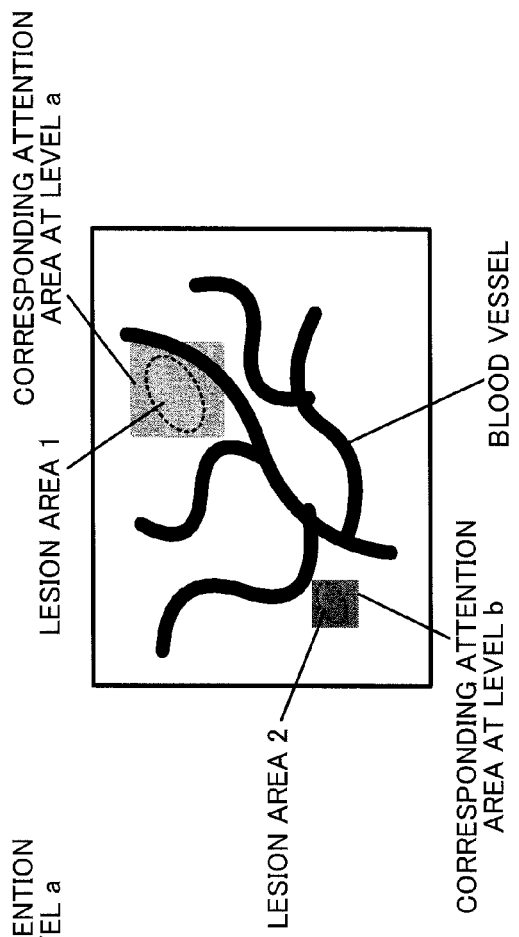
FIG. 31B illustrates an example in which a color conversion process has been performed on two corresponding attention areas using a different target color.
Figure 31A:
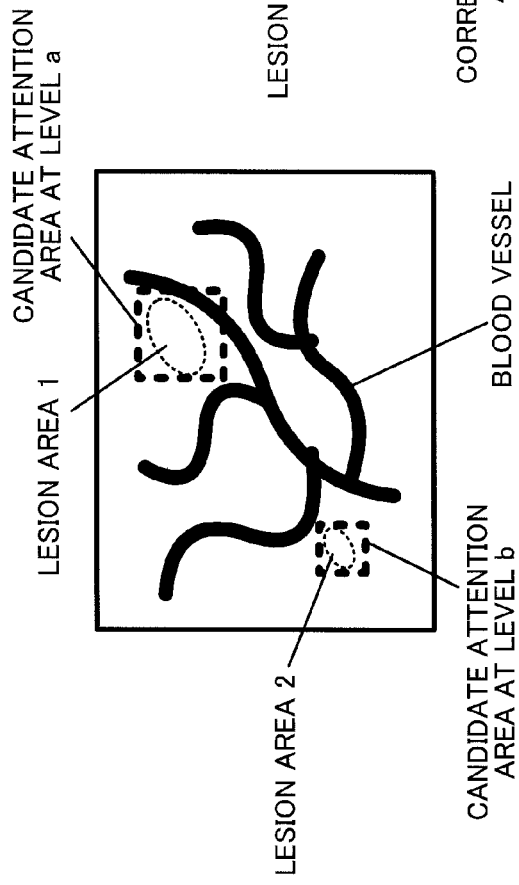
FIG. 31A illustrates an example of a normal light image and candidate attention area information.

FIG. 31A illustrates an example of the normal light image output from the normal light image acquisition section 320, and the candidate attention area information. Position information about each pixel included in the candidate attention area at the level a and each pixel included in the candidate attention area at the level b (indicated by a dotted line) is input to the area selection section 34313 as the candidate attention area information.

The area selection section 34313 sets the attention area and the corresponding attention area in the same manner as in the second embodiment. The area selection section 34313 may also set the alert area.

The area processing section 34314 processes the normal light image output from the normal light image acquisition section 320 using the candidate attention area information output from the candidate attention area detection section 341.

The area processing section 34314 performs a color conversion process on each pixel within the normal light image that is indicated by the corresponding attention area information input from the area selection section 34313 using the following expressions (23) to (28), for example. Note that r(x, y), g(x, y), and b(x, y) are the signal values of the R, G, and B channels at the coordinates (x, y) of the normal light image before the color conversion process is performed, and r_out(x, y), g_out(x, y), and b_out(x, y) are the signal values of the R, G, and B channels at the coordinates (x, y) of the normal light image after the color conversion process has been performed. Ta_r, Ta_g, and Ta_b are R, G, and B signal values of an arbitrary target color that corresponds to the corresponding attention area at the level a, and are determined based on the attention information set by the attention information setting section 34311. Tb_r, Tb_g, and Tb_b are R, G, and B signal values of an arbitrary target color that corresponds to the corresponding attention area at the level b, and are determined based on the attention information. "gain" is an arbitrary coefficient.

Corresponding attention area at level a $$r\_out(x,y)=gain*r(x,y)+(1-gain)*Ta\_r \tag{23}$$

$$g\_out(x,y)=gain*g(x,y)+(1-gain)*Ta\_g \tag{24}$$

$$b\_out(x,y)=gain*b(x,y)+(1-gain)*Ta\_b \tag{25}$$

Corresponding attention area at level b $$r\_out(x,y)=gain*r(x,y)+(1-gain)*Tb\_r \tag{26}$$

$$g\_out(x,y)=gain*g(x,y)+(1-gain)*Tb\_g \tag{27}$$

$$b\_out(x,y)=gain*b(x,y)\pm(1-gain)*Tb\_b \tag{28}$$

The above color conversion process allows the corresponding attention area that is suspected to be a lesion area to be displayed in a different color (see FIG. 31B). This makes it possible to prevent a situation in which a lesion area is missed while reducing the burden on the doctor during a diagnosis that utilizes the normal light image and the special light image.

Note that the area processing section 34314 may process the corresponding attention area within the normal light image corresponding to the degree of attention using a different color conversion process (refer to the second embodiment).

Note that each section of the image processing section 300 need not necessarily be implemented by hardware. For example, a CPU may perform the process of each section on an image acquired in advance in the same manner as in the first embodiment. Specifically, the process of each section may be implemented by software by causing the CPU to execute a program. Alternatively, the process of each section may partially be implemented by software.

Figure 28:
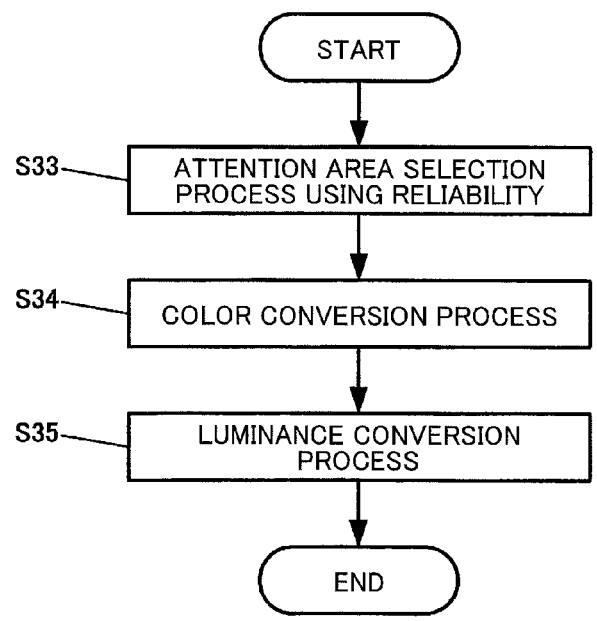
FIG. 28 is another flowchart illustrating a processing process.
Figure 29:
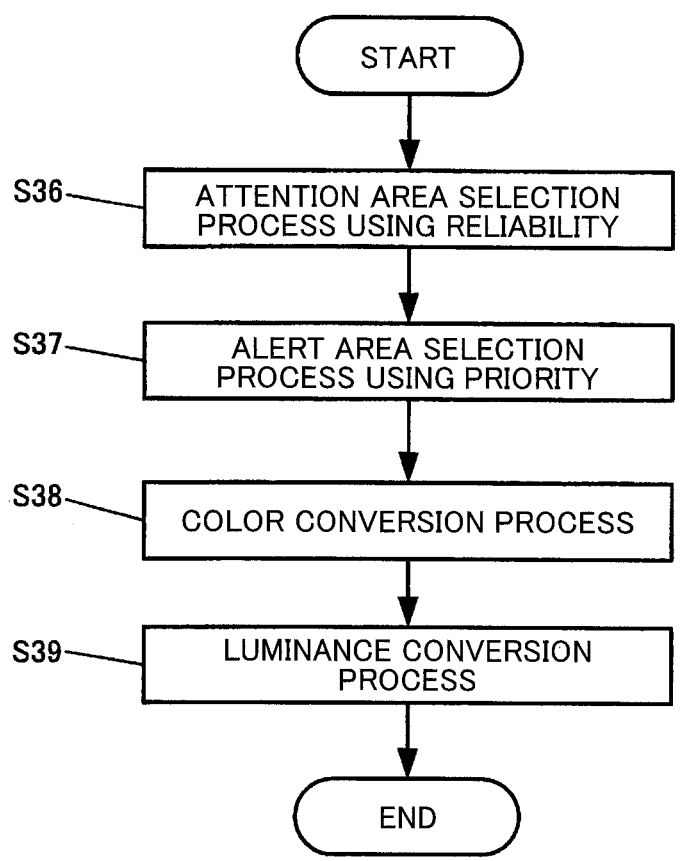
FIG. 29 is another flowchart illustrating a processing process.

In this case, the process is performed in the same as in the first embodiment except for the candidate attention area detection step (S13) in FIG. 19 and the color conversion step (S34) in FIG. 28. A specific process according to the third embodiment when implementing the attention area detection step (S13) in FIG. 19 is described below using the flowchart illustrated in FIG. 20.

In a step S41, a plurality of local areas are set within the special light image in the same manner as in the second embodiment. The feature quantity of each local area is calculated in the same manner as in the second embodiment (S42). In the third embodiment, the hue H is used as an example of the feature quantity. The hue H(m, n) of each local area is compared with the given threshold value Thi, and each local area is classified into one of a plurality of groups corresponding to the comparison results (S43). The candidate attention area is detected in the same manner as described above corresponding to the degree of attention. The position of each pixel included in the candidate attention area is calculated from the coordinates of each local area a(m, n) detected as the candidate attention area at each attention level and information about the pixels included in each local area, and the calculated position of each pixel is output as the candidate attention area information at each attention level (S44). Flag information that indicates whether or not the candidate attention area has been detected within the special light image is then output (S45).

In the color conversion step (see FIG. 28) according to the third embodiment, the normal light image is processed using a target color that differs depending on the attention level based on the candidate attention area information at each attention level that has been output in the candidate attention area detection step (see the expressions (23) to (28)).

The above color conversion process allows the corresponding attention area that is suspected to be a lesion area to be displayed in a different color (see FIG. 31B). This makes it possible to prevent a situation in which a lesion area is missed while reducing the burden on the doctor during a diagnosis that utilizes the normal light image and the special light image.

According to the third embodiment, the processing section 3431 includes the attention information setting section 34311 that sets the attention information that indicates the degree of attention corresponding to each candidate attention area. The processing section 3431 changes the target color used for the color conversion process corresponding to the degree of attention indicated by the attention information.

According to this configuration, when two or more lesion areas have been detected, these lesion areas can be displayed in a different color (see FIG. 31B). For example, a cancer area and an inflammation area may be displayed in a different color.

5. Fourth Embodiment

An endoscope system according to a fourth embodiment of the invention is described below with reference to FIG. 32. In the first to third embodiments, the normal light image and the special light image are acquired using two imaging elements. The fourth embodiment illustrates an example in which the normal light image and the special light image are acquired by image processing using only a first imaging element that includes a Bayer color filter array. The endoscope system according to the fifth embodiment includes a light source section 100, an insertion section 200, an image processing section 300, a display section 400, and an external I/F section 500. Note that description of the same elements as those described above in connection with the first to third embodiments is appropriately omitted.

The light source section 100 includes a white light source 110 and a condenser lens 120.

The insertion section 200 includes a light guide fiber 210 that guides light focused by the light source section 100, an illumination lens 220 that diffuses light that has been guided by the light guide fiber 210, and illuminates an observation target, an objective lens 230 that focuses light reflected by the observation target, and a first imaging element 250 that detects the focused reflected light. The first imaging element 250 includes a Bayer color filter array that is used to capture a normal light image, for example. The color filters of the first imaging element 250 have spectral characteristics illustrated in FIG. 4, for example.

The image processing section 300 includes an A/D conversion section 310, a normal light image acquisition section 320, a special light image acquisition section 330, an output image generation section 340, and a control section 350.

The external I/F section 500 is an interface that allows the user to input information to the endoscope system, for example.

The A/D conversion section 310 converts an analog signal output from the first imaging element 250 into a digital signal, and outputs the digital signal.

The normal light image acquisition section 320 acquires a normal light image from the digital signal output from the A/D conversion section 310. The special light image acquisition section 330 acquires a special light image from the digital signal output from the A/D conversion section 310.

The normal light image acquired by the normal light image acquisition section 320 and the special light image acquired by the special light image acquisition section 330 are output to the output image generation section 340. The output image generation section 340 generates one output image from the normal light image and the special light image, and outputs the output image to the image display section.

Figure 7:
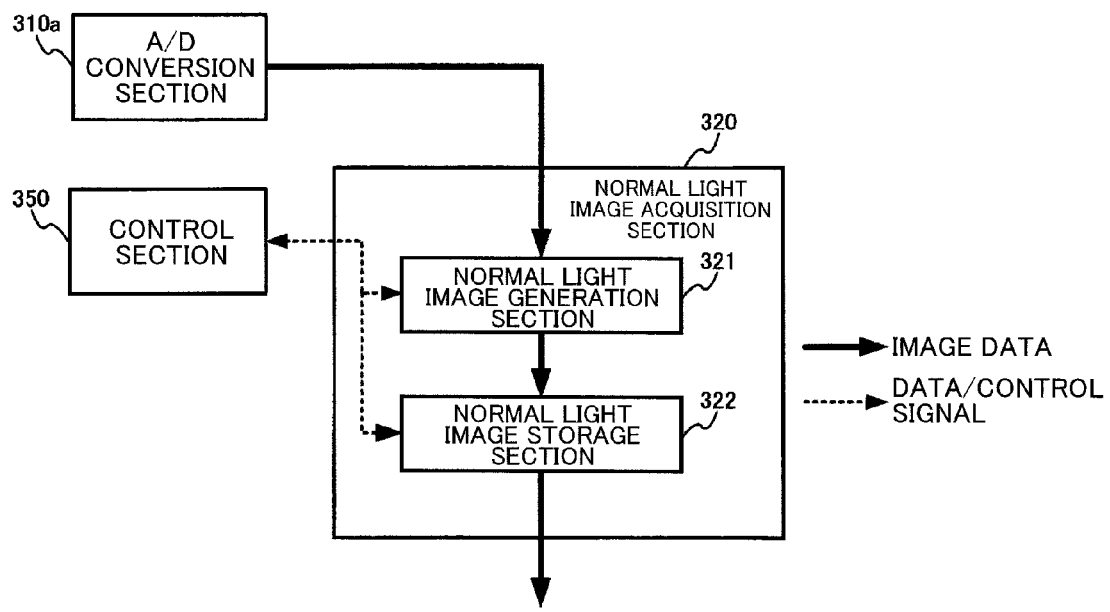
FIG. 7 illustrates a configuration example of a normal light image acquisition section.

The normal light image acquisition section 320 includes a normal light image generation section 321 and a normal light image storage section 322 (see FIG. 7). The function and the operation of each section (normal light image generation section 321 and normal light image storage section 322) are the same as those described above with reference to FIG. 7. Therefore, detailed description thereof is omitted.

Figure 33:
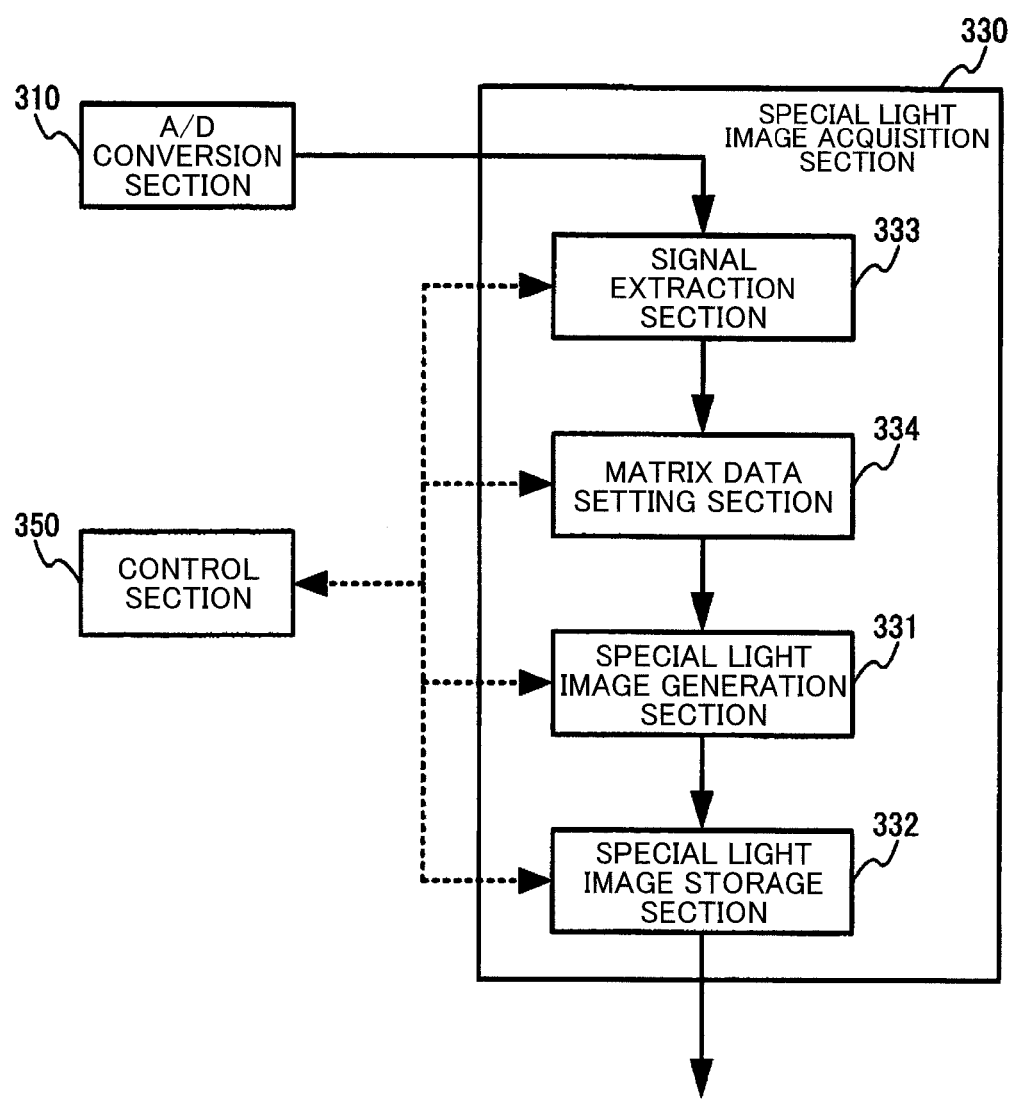
FIG. 33 illustrates another configuration example of a special light image acquisition section.

The special light image acquisition section 330 is described below with reference to FIG. 33. The special light image acquisition section 330 includes a special light image generation section 331, a special light image storage section 332, a signal extraction section 333, and a matrix data setting section 334. The special light image generation section 331 processes the digital image signal input from the A/D conversion section 310 to generate a special light image. In the first embodiment, the special light image is a narrow-band light image. The digital image signal input to the special light image generation section 331 is the same as the digital image signal input to the normal light image generation section 321.

The narrow-band light image is generated as described below using the signal extraction section 333, the matrix data setting section 334, and the special light image generation section 331. Specifically, a known interpolation process is performed on the input digital image signal to generate a color image that includes R, G, and B channels. The color image is obtained by capturing the object using the first imaging element 250 in a state in which white light is applied to the object. The spectral reflectivity of the object at each pixel of the color image is estimated using a known spectrum estimation technique. The details of the spectrum estimation technique are disclosed in paragraphs [0054] to [0065] of JP-A-2000-115553, for example. Spectral image information in which each pixel has the spectrum reflectivity $O(\lambda)$ ($\lambda$=380 to 780) of the object in the range from 380 nm to 780 nm at intervals of 10 nm is thus acquired. The spectrum reflectivity at the coordinates (x, y) within the image is indicated by $O(\lambda)x, y$. The spectral emissivity of the white light source is indicated by $E(\lambda)$, the spectral transmittance of the optical system is indicated by $L(\lambda)$, the spectral sensitivity of the pixel corresponding to the color filter g2 of the second imaging element 260 (refer to the first embodiment) is indicated by $g2(\lambda)$, and the spectral sensitivity of the pixel corresponding to the color filter b2 of the second imaging element 260 is indicated by $b2(\lambda)$. The signal values $G2'(x, y)$ and $B2'(x, y)$ at the coordinates (x, y) of the G2' image and the B2' image corresponding to the G2 image and the B2 image (refer to the first embodiment) are calculated by the following expressions (29) and (30), respectively.

$$G2'(x,y) = \int E(\lambda) \cdot O(\lambda) \cdot L(\lambda \cdot g2\lambda) d\lambda \qquad (29)$$

$$B2'(x,y) = \int E(\lambda) \cdot O(\lambda) \cdot L(\lambda \cdot b2\lambda) d\lambda \qquad (30)$$

The G2' image and the B2' image can be acquired from the image signal obtained by the first imaging element 250 by performing the above calculations over the entire image.

A color image that includes R, G, and B channels is generated from the G2' image and the B2' image in the same manner as in the first embodiment. For example, a color image is generated by inputting the G2 image to the R channel, and inputting the B2 image to the G channel and the B channel. The special light image generation section 331 performs a white balance process, a grayscale transformation process, and the like on the generated color image, and outputs the resulting color image as a narrow-band light image. The special light image storage section 332 stores the special light image output from the special light image generation section 331.

The process performed after the images have been acquired by the normal light image acquisition section 320 and the special light image acquisition section 330 is the same as that described above in connection with the first, second, or third embodiment.

According to the fourth embodiment, the second image acquisition section (special light image acquisition section 330 in a narrow sense) generates the second image based on the first image. More specifically, the second image acquisition section includes the signal extraction section 333 and the matrix data setting section 334. The signal extraction section 333 extracts a signal within the wavelength band of white light. The matrix data setting section 334 sets matrix data for calculating a signal within the specific wavelength band. The second image acquisition section calculates a signal within the specific wavelength band from the signal extracted by the signal extraction section 333 using the matrix data to generate the second image.

Figure 32:
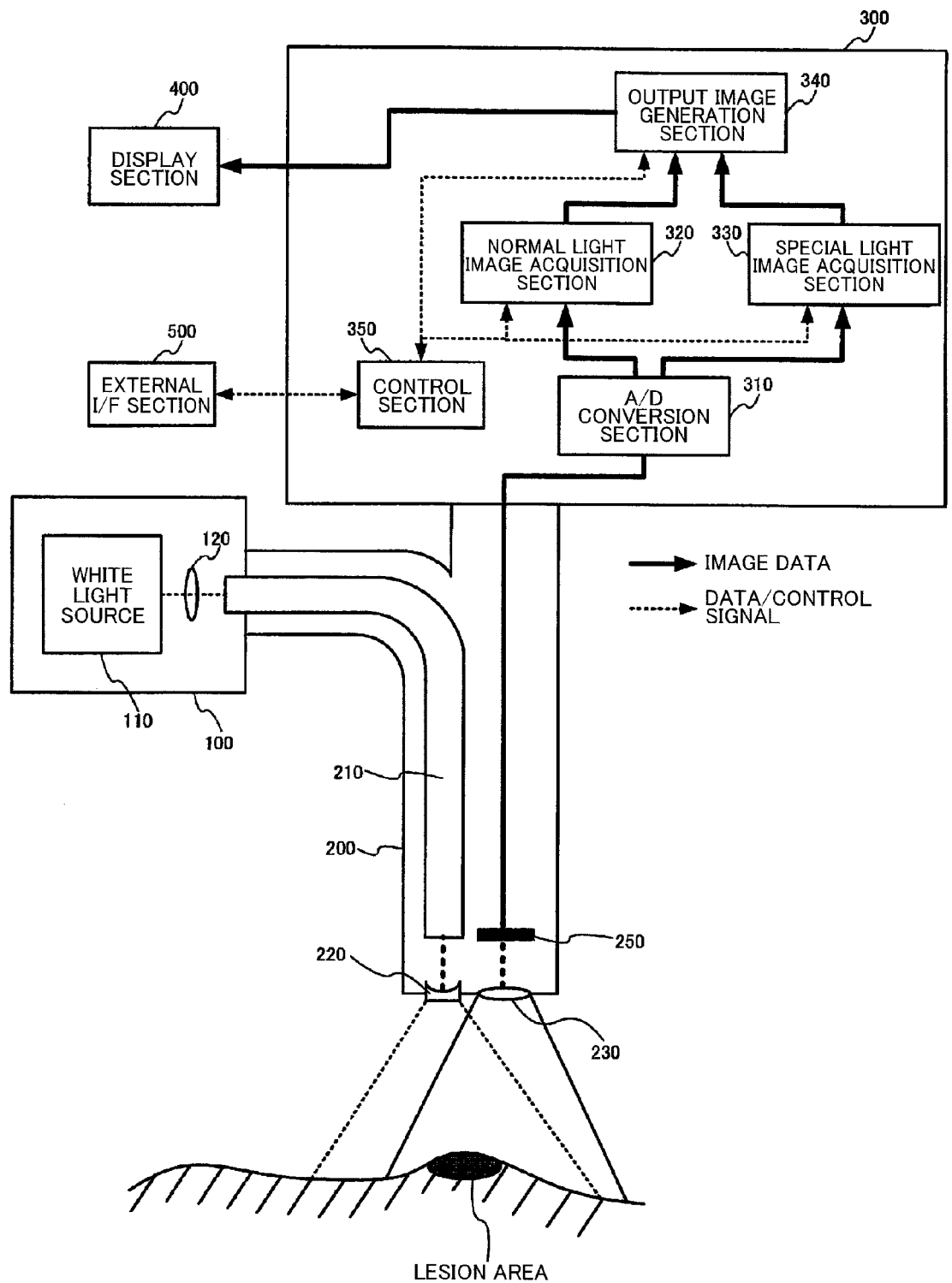
FIG. 32 illustrates another system configuration example according to one embodiment of the invention.

Since the second image can be generated based on the first image, an endoscope system can be implemented using only one imaging element, and the insertion section 200 can be reduced in size (see FIG. 32). Moreover, since the number of parts can be reduced, a reduction in cost can be achieved.

6. Fifth Embodiment

Figure 34:
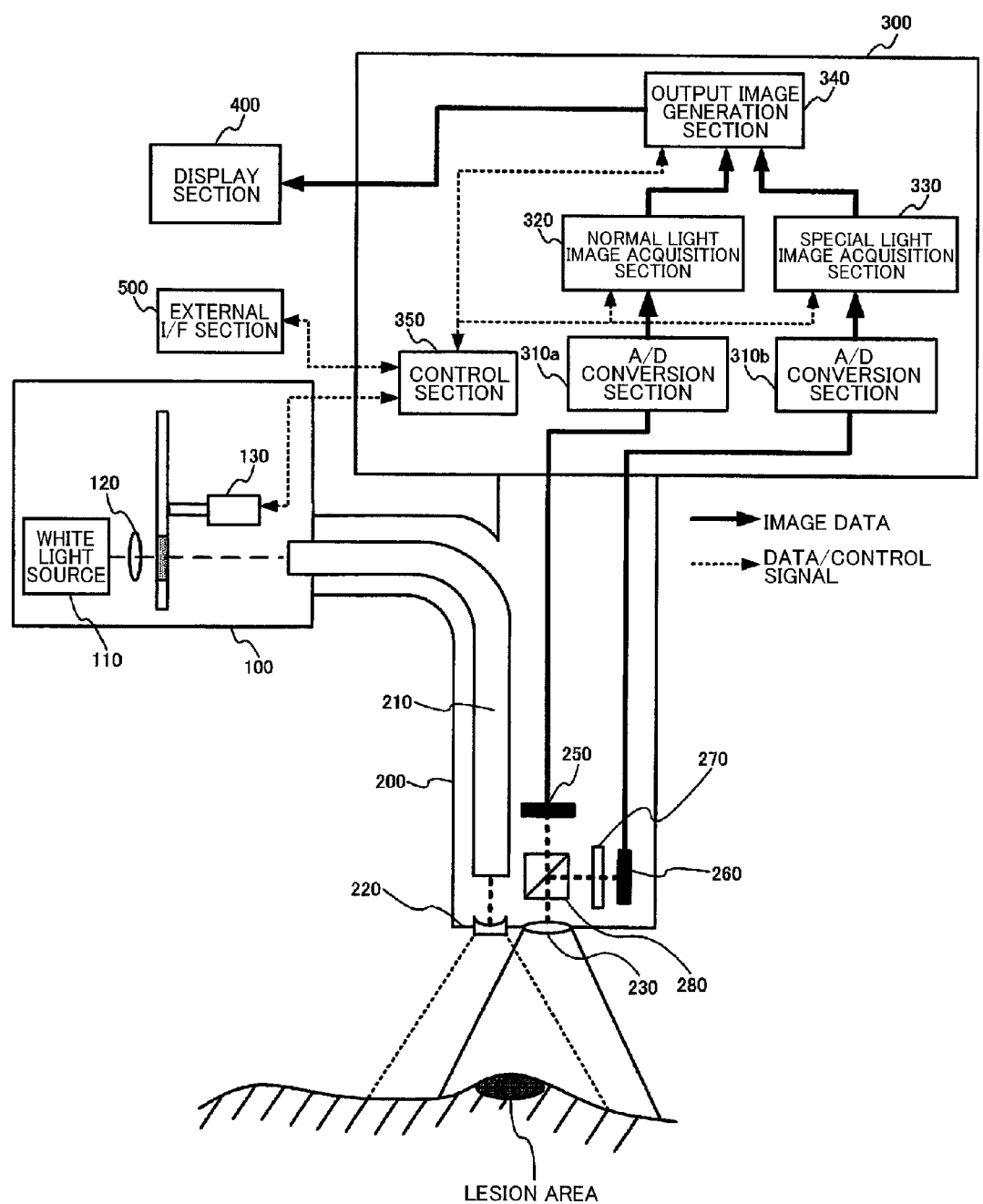
FIG. 34 illustrates another system configuration example according to one embodiment of the invention.

An endoscope system according to a fifth embodiment of the invention is described below with reference to FIG. 34. The endoscope system according to the fifth embodiment includes a light source section 100, an insertion section 200, an image processing section 300, a display section 400, and an external I/F section 500.

The light source section 100 includes a white light source 110 that emits white light, a condenser lens 120 that focuses light emitted from the light source on a light guide fiber 210, and a rotary filter 130 that extracts light within a specific wavelength band from white light.

Figure 35:
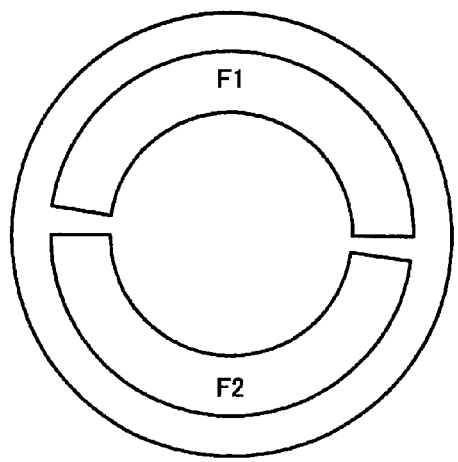
FIG. 35 illustrates an example of a rotary filter.
Figure 36:
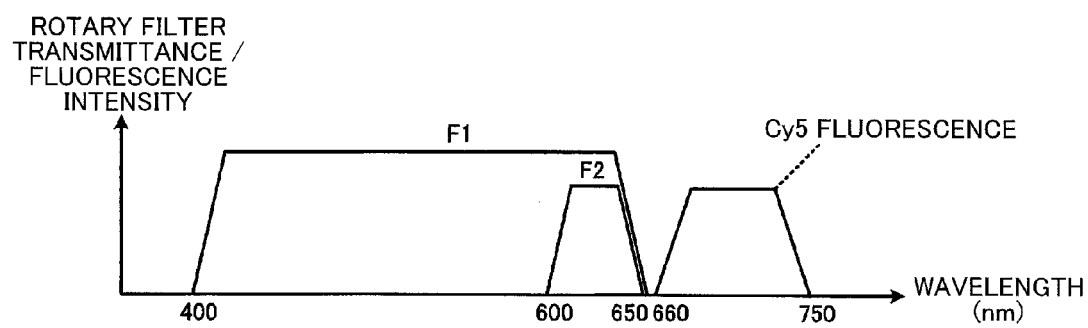
FIG. 36 illustrates an example of the characteristics of filters F1 and F2 and fluorescence.

As illustrated in FIG. 35, the rotary filter 130 includes two color filters F1 and F2 that differ in transmittance characteristics. As illustrated in FIG. 36, the filter F1 allows light within a wavelength band of 400 to 650 nm to pass through, and the filter F2 allows light within a wavelength band of 600 to 650 nm to pass through, for example. The filter F1 allows white light to pass through. Light within a wavelength band of 600 to 650 nm that is extracted by the filter F2 excites a fluorescent agent (e.g., Cy5) to produce fluorescence within a wavelength band of 660 to 750 nm. The fluorescent agent is specifically accumulated in a lesion area (e.g., tumor). The insertion section 200 is formed to be elongated and flexible (i.e., can be curved (bent)) so that the insertion section 200 can be inserted into a body cavity or the like.

Figure 37:
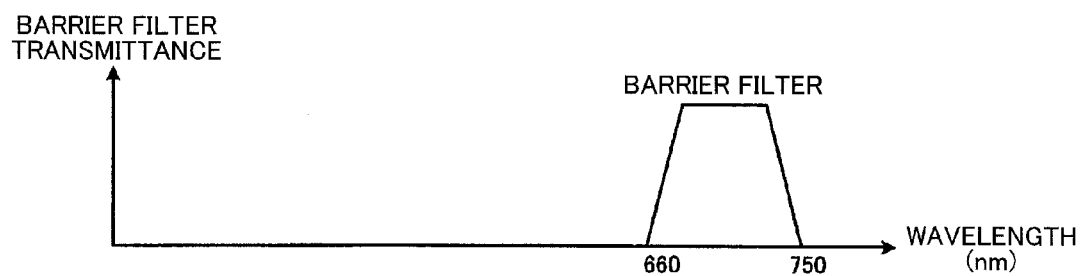
FIG. 37 illustrates an example of the characteristics of a barrier filter.

The insertion section 200 includes the light guide fiber 210 that guides light has been focused by the light source section, an illumination lens 220 that diffuses light that has been guided by the light guide fiber 210, and illuminates an observation target, an objective lens 230 that focuses light reflected by the observation target, a dichroic mirror 280 that splits the focused reflected light and fluorescence into different optical paths, a barrier filter 270 that blocks excitation light included in the fluorescence split by the dichroic mirror 280, a first imaging element 250 that detects the reflected light split by the dichroic mirror 280, and a second imaging element 260 that detects the fluorescence that has passed through the barrier filter 270. As illustrated in FIG. 37, the barrier filter 270 allows only light split from the reflected light by the dichroic mirror 280 and having a wavelength band of 660 to 750 nm (fluorescence) to pass through, and blocks the remaining light. The first imaging element 250 is a Bayer color imaging element having R, G, and B spectral characteristics illustrated in FIG. 4, for example. The second imaging element 260 is a monochrome imaging element that has relatively high sensitivity in a wavelength band of 660 to 750 nm, for example.

The image processing section 300 includes an A/D conversion section 310, a normal light image acquisition section 320, a special light image acquisition section 330, an output image generation section 340, and a control section 350. The control section 350 is bidirectionally connected to a normal light image acquisition section 320, a special light image acquisition section 330, and an output image generation section 340, and controls the normal light image acquisition section 320, the special light image acquisition section 330, and the output image generation section 340.

The control section 350 is also bidirectionally connected to the rotary filter 130. The rotary filter 130 causes illumination light to be applied to the observation target (i.e., tissue inside a body cavity) while sequentially switching the filters F1 and F2 by driving (rotating) a motor based on a signal output from the control section 330. The control section 350 outputs information about the filters F1 and F2 disposed in an optical path to the normal light image acquisition section 320, the special light image acquisition section 330, and the output image generation section 340 as a trigger signal.

The external I/F section 500 is an interface that allows the user to input information to the endoscope system, for example.

The A/D conversion section 310 converts an analog signal output from the first imaging element 250 and the second imaging element 260 into a digital signal, and outputs the digital signal.

The normal light image acquisition section 320 acquires a normal light image from the digital signal output from the A/D conversion section 310. The special light image acquisition section 330 acquires a special light image from the digital signal output from the A/D conversion section 310.

The normal light image acquired by the normal light image acquisition section 320 and the special light image acquired by the special light image acquisition section 330 are output to the output image generation section 340. The output image generation section 340 generates one output image from the normal light image and the special light image, and outputs the output image to the image display section.

As illustrated in FIG. 7, the normal light image acquisition section 320 includes a normal light image generation section 321 and a normal light image storage section 322. The normal light image generation section 321 specifies a period in which the filter F1 is positioned within the optical path based on the trigger signal transmitted from the control section 350, and processes the digital signal converted from the analog signal transmitted from the first imaging element in a period in which the filter F1 is positioned within the optical path to generate a normal light image. More specifically, the normal light image generation section 321 performs an interpolation process, a white balance process, a color conversion process, a grayscale transformation process, and the like on the digital signal to generate a normal light image, and outputs the normal light image. The normal light image storage section 322 stores the normal light image output from the normal light image generation section 321.

Figure 8:
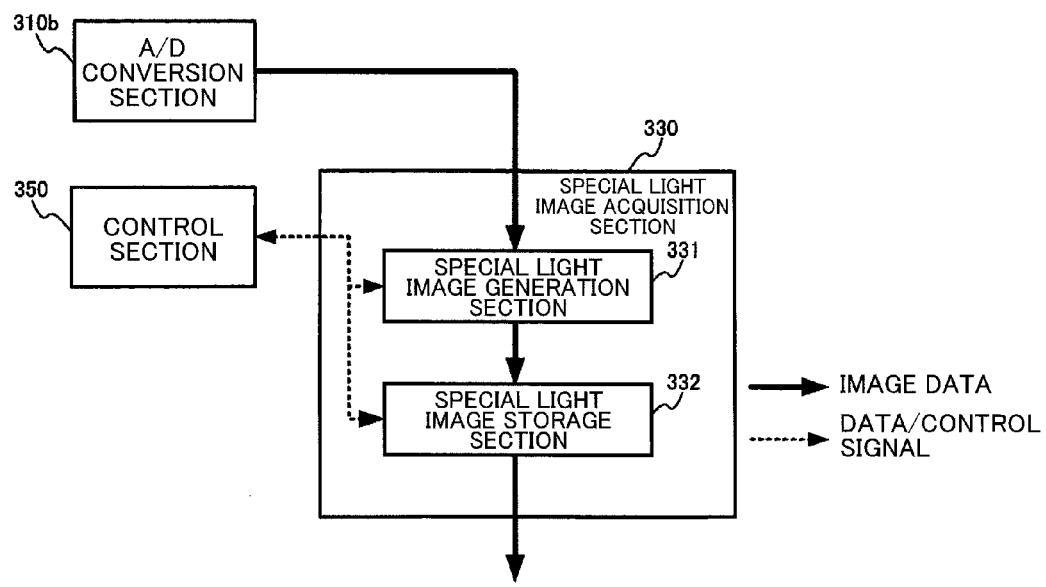
FIG. 8 illustrates a configuration example of a special light image acquisition section.

As illustrated in FIG. 8, the special light image acquisition section 330 includes a special light image generation section 331 and a special light image storage section 332. The special light image generation section 331 specifies a period in which the filter F2 is positioned within the optical path based on the trigger signal transmitted from the control section 350, and processes the digital signal converted from the analog signal transmitted from the second imaging element in a period in which the filter F2 is positioned within the optical path to generate a special light image. In the fifth embodiment, the special light image is a monochrome fluorescent image. More specifically, the special light image generation section 331 performs an interpolation process, a gain control process, a grayscale transformation process, and the like on the image signal that indicates fluorescence produced from a lesion area where the fluorescent agent is accumulated to generate a monochrome special light image, and outputs the special light image. The special light image storage section 332 stores the special light image output from the special light image generation section 331.

Figure 40:
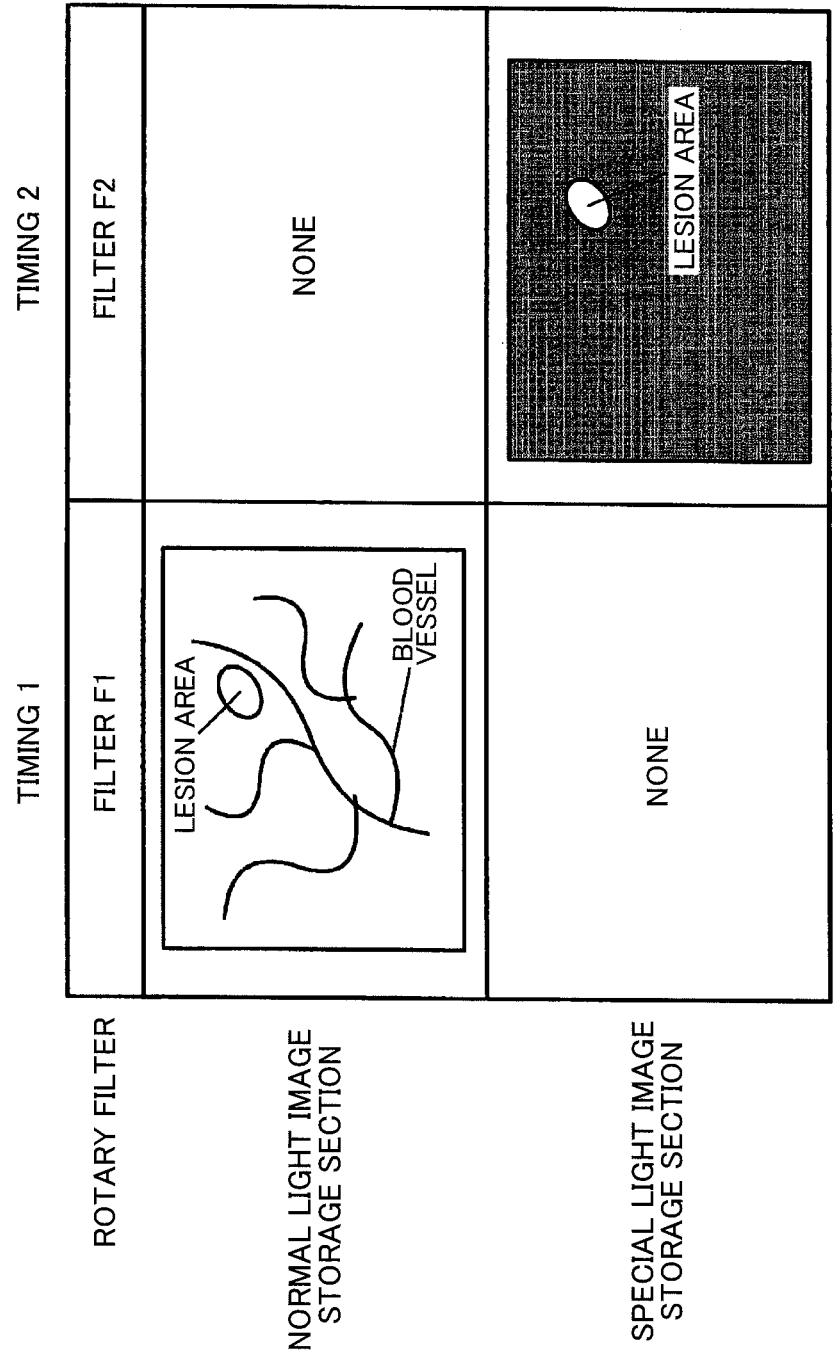
FIG. 40 illustrates an example of a combination of a filter and the resulting image at each timing.

FIG. 40 is a view illustrating the type of filter positioned within the optical path, and images stored in the normal light image storage section 322 and the special light image storage section 332. As illustrated in FIG. 40, the filter F1 is inserted into the optical path at a timing 1. In this case, white light is emitted as the illumination light. The normal light image is stored in the normal light image storage section 322 as a color image, and an image is not stored in the special light image storage section 332. The filter F2 is inserted into the optical path at a timing 2. In this case, excitation light is emitted as the illumination light. Fluorescence produced from a lesion area where the fluorescent agent is accumulated is stored in the special light image storage section 332 as a monochrome image, and an image is not stored in the normal light image storage section 322. The normal light image storage section 322 and the special light image storage section 332 can store a plurality of images.

Figure 38:
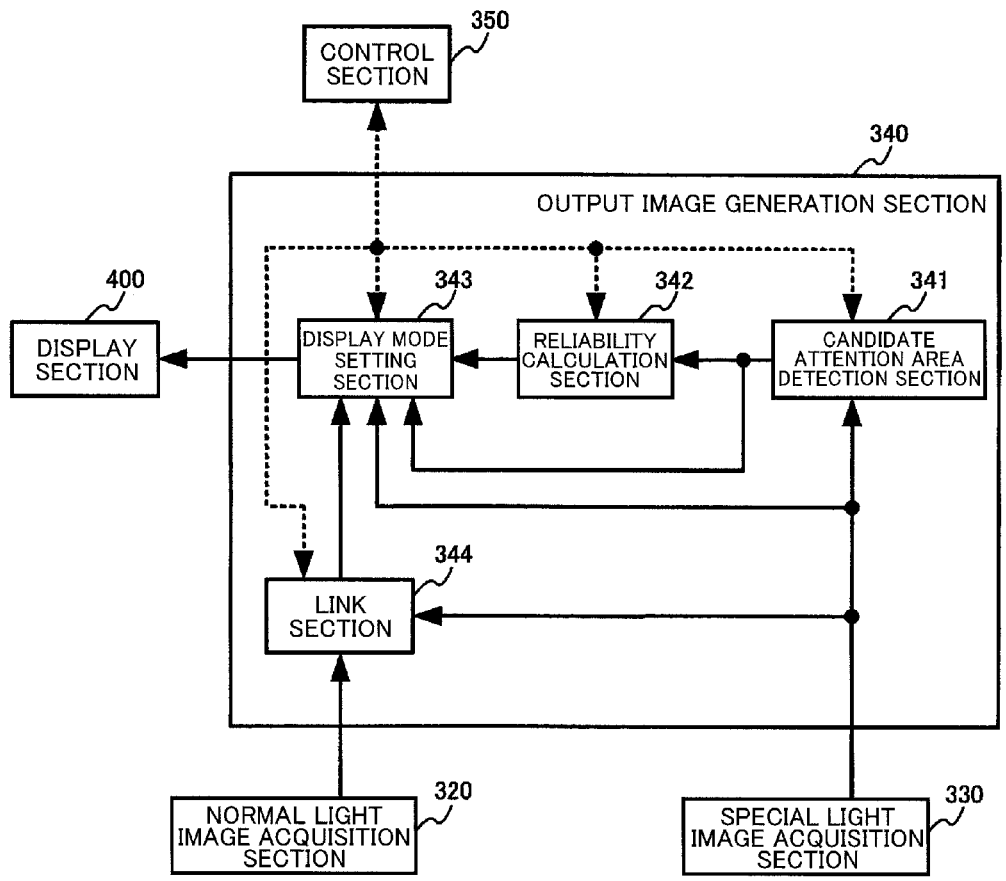
FIG. 38 illustrates another system configuration example of an output image generation section.

The configuration of the output image generation section 340 according to the fifth embodiment is described below. FIG. 38 is a block diagram illustrating an example of the configuration of the output image generation section 340. The output image generation section 340 includes a candidate attention area detection section 341, a reliability calculation section 342, a display mode setting section 343, and a link section 344.

In the fifth embodiment, since the normal light image and the special light image are alternately acquired by the normal light image acquisition section 320 and the special light image acquisition section 330, the link section 344 links the normal light image and the special light image.

Figure 39:
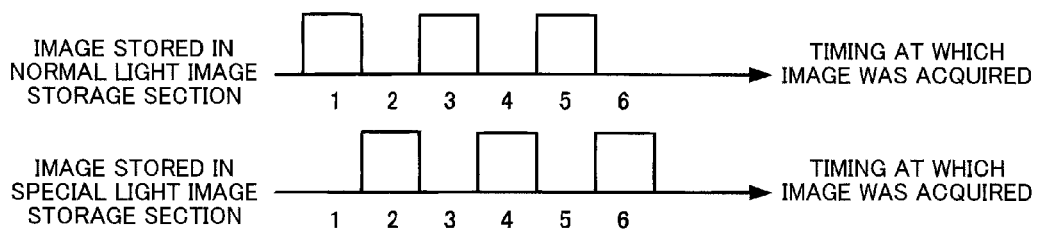
FIG. 39 illustrates an example of acquisition timings of a normal light image and a special light image.

The process performed by the link section 344 according to the fifth embodiment is described in detail below. FIG. 39 is a view illustrating a timing at which an image stored in the normal light image storage section 322 was acquired, and a timing at which an image stored in the special light image storage section 332 was acquired. The link section 344 sequentially reads the normal light image and the special light image that are linked so that the difference in image acquisition timing becomes a minimum from the normal light image storage section 322 and the special light image storage section 332 according to a control signal input from the control section 350. Specifically, the link section 344 reads the normal light image acquired at the timing 1 and the special light image acquired at the timing 2, and then reads the normal light image acquired at the timing 2 and the special light image acquired at the timing 3. The link section 344 thus acquires the normal light image and the special light image at the same interval as the image acquisition interval.

Figure 41:
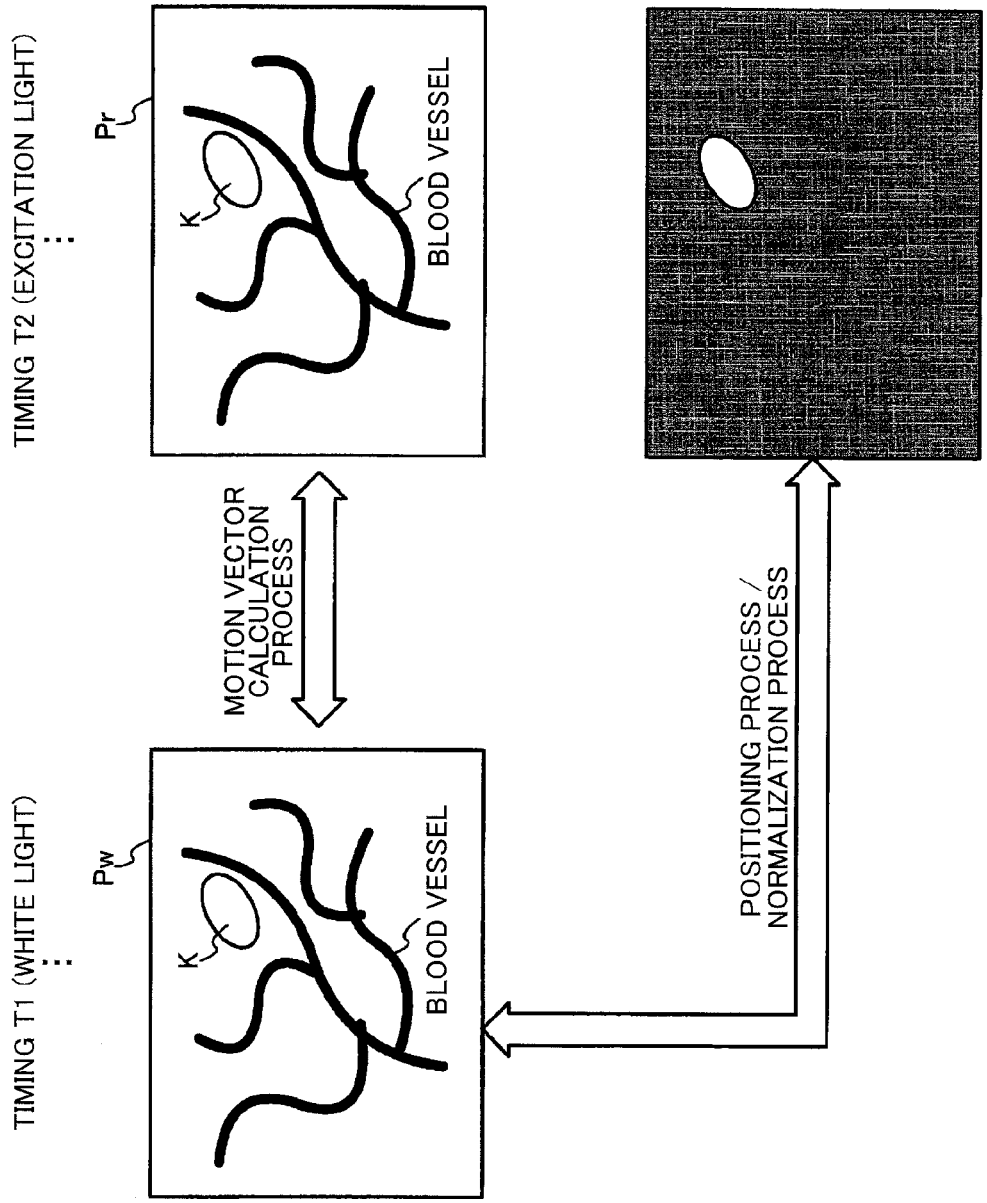
FIG. 41 is a view illustrating a method that links a normal light image and a special light image using a motion vector.
Figure 42:
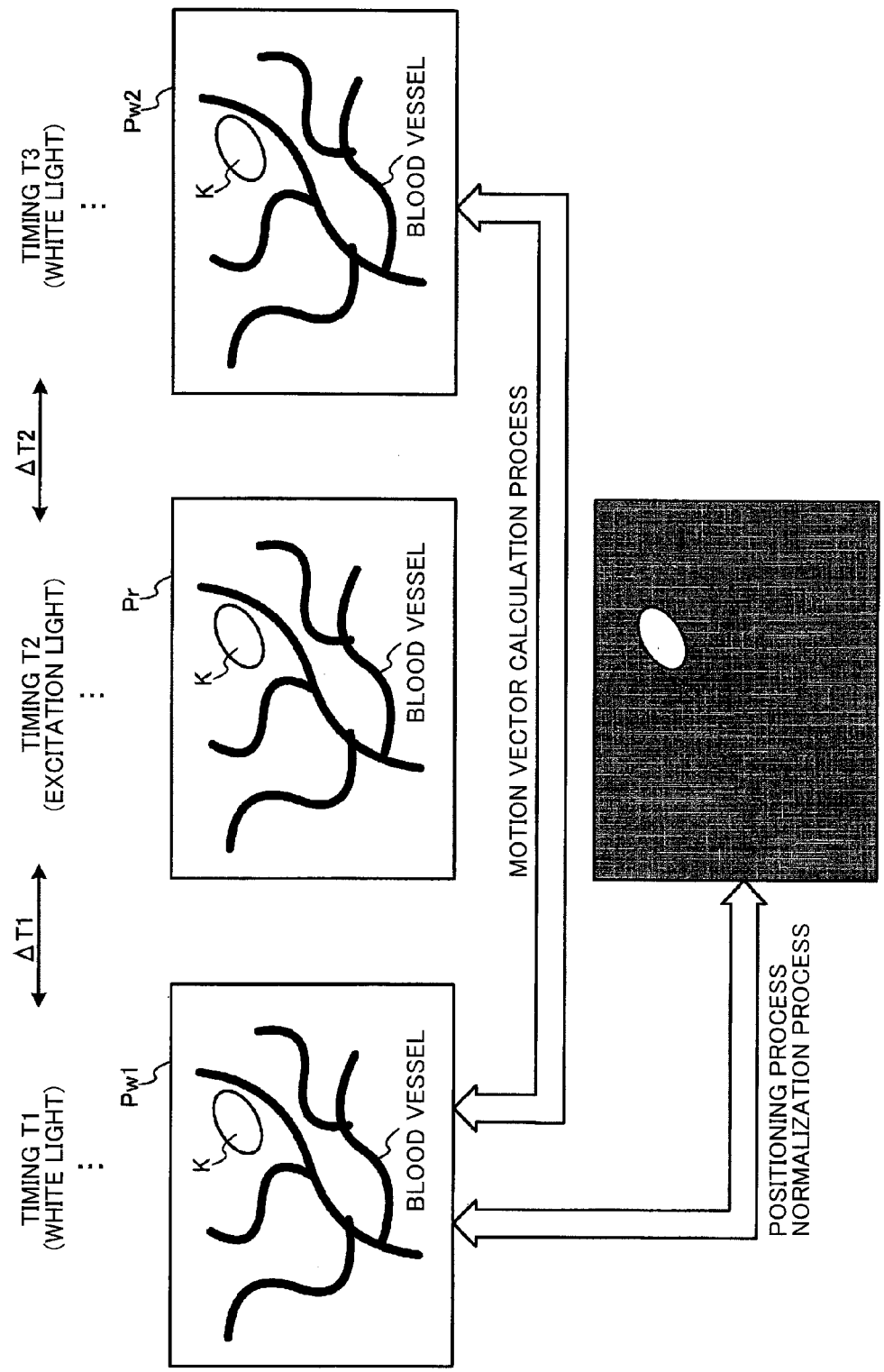
FIG. 42 is a view illustrating a method that links a normal light image and a special light image using a motion vector.

The link section 344 may perform the link process using a known method, FIGS. 41 and 42 illustrate a specific link method. In FIG. 41, white light is emitted at a timing T1, and excitation light is emitted at a timing T2. Therefore, a normal light image is acquired at the timing T1, and a special light image is acquired at the timing T2. A normal light image may also be acquired at the timing T2 using the first imaging element 250 (not illustrated in FIG. 40). The normal light image acquired at the timing T1 and the special light image acquired at the timing T2 can be linked by calculating the motion vector between the normal light image acquired at the timing T1 and the normal light image acquired at the timing T2.

As illustrated in FIG. 42, the motion vector between the normal light image acquired at the timing T1 and the normal light image acquired at the timing T3 by applying white light may be calculated. In this case, the motion vector can be calculated even if a normal light image has not been acquired at the timing T2. The normal light image acquired at the timing T1 and the special light image acquired at the timing T2 can be linked by utilizing timing intervals $\Delta T1$ and $\Delta T2$.

The normal light image that has been linked to the special light image is output to the display mode setting section 343. The special light image that has been linked to the normal light image is output to the candidate attention area detection section 341 and the display mode setting section 343. The candidate attention area detection section 341 detects the attention area using the special light image output from the special light image acquisition section 330, and outputs the attention area information to the reliability calculation section 342 and the display mode setting section 343. The reliability calculation section 342 is connected to the display mode setting section 343. The control section 350 is bidirectionally connected to the candidate attention area detection section 341, the reliability calculation section 342, the display mode setting section 343, and the link section 344, and controls the candidate attention area detection section 341, the reliability calculation section 342, the display mode setting section 343, and the link section 344. The display mode setting section 343 selects the normal light image output from the normal light image acquisition section 320 or the special light image output from the special light image acquisition section 330, and outputs the selected image to the display section 400. The display mode setting section 343 may process the normal light image or the special light image based on the attention area information output from the candidate attention area detection section 341, and may output the processed image to the display section 400.

The candidate attention area detection section 341, the reliability calculation section 342, and the display mode setting section 343 are configured in the same manner as in the first, second or third embodiment. In the fifth embodiment, since the special light image is a monochrome fluorescent image, the luminance of the fluorescent image may be used as the feature quantity utilized by the candidate attention area detection section 341, for example.

Figure 43:
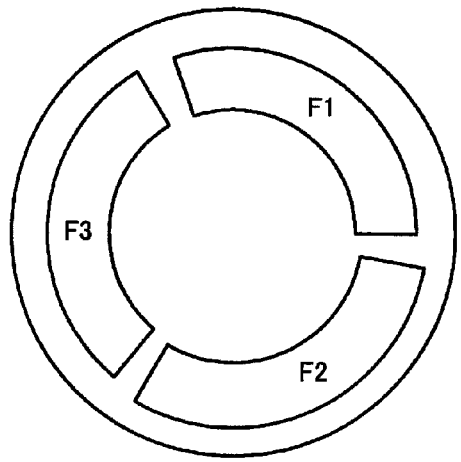
FIG. 43 illustrates another example of a rotary filter.

Although the fifth embodiment utilizes two types of illumination light, three or more types of illumination light may also be used. For example, a rotary filter illustrated in FIG. 43 may be used. In FIG. 43, a filter F1 allows white light to pass through, a filter F2 allows first excitation light due to a fluorescent agent such as Cy5 to pass through, and a filter F3 allows second excitation light due to another fluorescent agent to pass through. In this case, a special light image can be generated by performing a pseudo-color process on a fluorescent image acquired by the second imaging element when the first excitation light is emitted and a fluorescent image acquired by the second imaging element when the second excitation light is emitted, for example. The feature quantity utilized by the candidate attention area detection section 341 may be the hue H in the same manner as in the first and the second embodiments, or may be luminance/color information other than the hue H. In this case, it is necessary to use a barrier filter that blocks the first excitation light and the second excitation light, but allows fluorescence due to the first excitation light and the second excitation light to pass through.

Although the fifth embodiment utilizes the fluorescent agent, intrinsic fluorescence produced from collagen in in vivo tissue may be observed (e.g., autofluorescence imaging (AFI)), for example. In this case, light within a wavelength band of 390 to 470 nm may be used as the excitation light, and a barrier filter that allows light within a wavelength band of 490 to 625 nm to pass through may be used. Light within a wavelength band of 540 to 560 nm that is absorbed by hemoglobin in blood may be used as the illumination light, and a pseudo-color image may be generated from the reflected light image and the intrinsic fluorescence image, and used as the special light image.

Light within a wavelength band of 790 to 820 nm and light within a wavelength band of 905 to 970 nm (infrared light) may be used as the illumination light after intravenously injecting indocyanine green (ICG), and a pseudo-color image may be generated from the reflected light images, and used as the special light image (e.g., infrared imaging (IRI)).

Note that each section of the image processing section 300 need not necessarily be implemented by hardware. For example, a CPU may perform the process of each section on an image acquired in advance in the same manner as in the first embodiment. Specifically, the process of each section may be implemented by software by causing the CPU to execute a program. Alternatively, the process of each section may partially be implemented by software.

Figure 44:
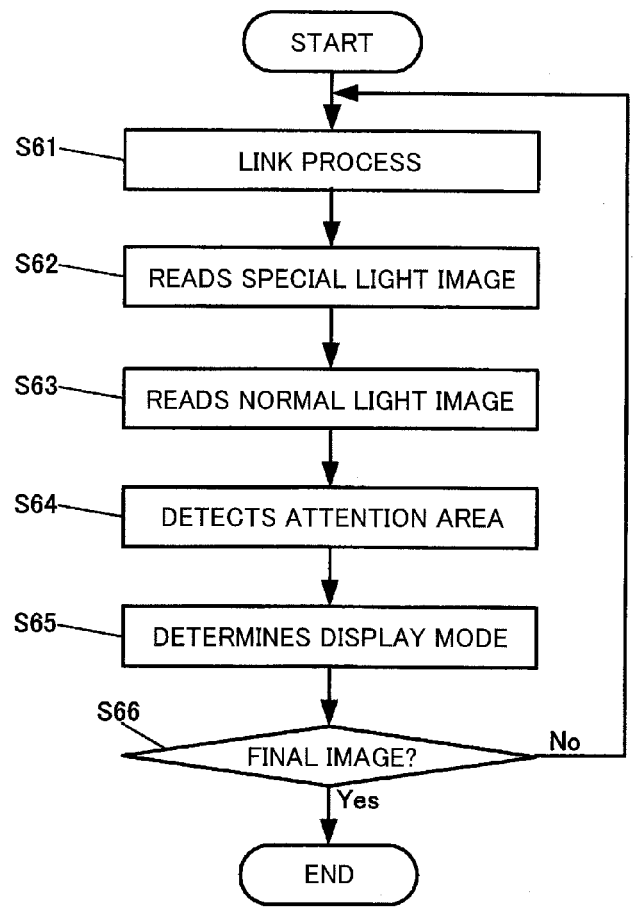
FIG. 44 is another flowchart illustrating a process according to one embodiment of the invention.

An example in which the process performed by the output image generation section 340 (see FIG. 38) on the normal light image and the special light image acquired in advance is implemented by software is described below using a flowchart illustrated in FIG. 44.

In a step S61, the normal light image and the special light image that have been alternately acquired are linked based on image acquisition timing information. The special light image is written into the memory (S62), and the normal light image linked to the special light image is written into the memory (S63). An attention area detection step (S64) and a display mode determination step (S65) are the same as those described above in connection with the first, second, or third embodiment. The process is terminated when all of the images have been processed, and is continuously performed when all of the images have not been processed (S66).

According to the fifth embodiment, the output image generation section 340 includes the link section 344 that links the first image and the second image based on first identification information that identifies the first image and second identification information that identifies the second image.

This makes it possible to link the first image and the second image even if the first image and the second image differ in acquisition (capture) timing. It is desirable to link the first image and the second image since the attention area (i.e., lesion area) is detected from the second image, and the first image is processed. Specifically, when it is desired to process the lesion area within the first image, an undesired area of the first image may be processed if the first image and the second image are shifted (differ in position). Therefore, it is desirable to link the first image and the second image when the first image and the second image cannot be acquired at the same time.

The first image acquisition section may acquire a white light image, and the second image acquisition section may acquire an image obtained using a light source that emits light within a specific wavelength band. The first identification information may be information about a timing at which the first image was captured, and the second identification information may be information about a timing at which the second image was captured. The link section may link the first image and the second image that were captured at close timings.

This makes it possible to link two images that were captured at close timings. In the example illustrated in FIG. 39, the normal light image acquired at the timing T1 and the special light image acquired at the timing T2 are linked, and the special light image acquired at the timing T2 and the normal light image acquired at the timing T3 are linked. This makes it possible to reduce a shift in position, and process an appropriate area (position) of the first image.

The first image and the second image may be an in vivo image. The specific wavelength band included in the in vivo image may be the wavelength band of fluorescence emitted from a fluorescent substance. Specifically, the specific wavelength band may be 490 to 625 nm.

This enables autofluorescence imaging (AFT). Intrinsic fluorescence from a fluorescent substance (e.g., collagen) can be observed by applying excitation light (390 to 470 nm). In this case, a lesion area can be highlighted in a color differing from that of a normal mucous membrane, so that a situation in which a lesion area is missed can be prevented, for example. A wavelength band of 490 to 625 nm is the wavelength band of fluorescence emitted from a fluorescent substance (e.g., collagen) when excitation light is applied. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence emitted from a fluorescent substance). A pseudo-color image may be generated by simultaneously applying light within a wavelength band (540 to 560 nm) that is absorbed by hemoglobin.

The first image and the second image may be an in vivo image. The specific wavelength band included in the in vivo image may be the wavelength band of infrared light. Specifically, the specific wavelength band may be 790 to 820 nm or 905 to 970 nm.

This enables infrared imaging (IRI). Information about a vessel or the blood flow in a deep area of a mucous membrane that is difficult to observe visually, can be highlighted by intravenously injecting indocyanine green (ICG) (infrared marker) that easily absorbs infrared light, and applying infrared light within the above wavelength band, so that the depth of cancer invasion or the therapeutic strategy can be determined, for example. An infrared marker exhibits maximum absorption in a wavelength band of 790 to 820 nm, and exhibits minimum absorption in a wavelength band of 905 to 970 nm. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for absorption by the infrared marker).

The first to fifth embodiments of the invention and the modifications thereof have been described above. Note that the invention is not limited to the first to fifth embodiments and the modifications thereof. Various modifications and variations may be made without departing from the scope of the invention. A plurality of elements described above in connection with the first to fifth embodiments and the modifications thereof may be appropriately combined. For example, some elements may be omitted from the elements described above in connection with the first to fifth embodiments and the modifications thereof. Some of the elements described above in connection with different embodiments or modifications thereof may be appropriately combined. Specifically, various modifications and applications are possible without materially departing from the novel teachings and advantages of the invention.

Any term (e.g., normal light image or special light image) cited with a different term (e.g., first image or second image) having a broader meaning or the same meaning at least once in the specification and the drawings may be replaced by the different term in any place in the specification and the drawings.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. An image processing device comprising:
a processor comprising hardware, the processor being configured to implement:
a first image acquisition section that acquires a first image, the first image being a color image that includes a plurality of channels, and includes an object image including information within a wavelength band of white light;
a second image acquisition section that acquires a second image, the second image being an image that includes an object image including information within a specific wavelength band, and differs from the plurality of channels included in the first image;
a candidate attention area detection section that detects a candidate attention area based on a feature quantity of each pixel within the second image, the candidate attention area being a candidate for an attention area;
a reliability calculation section that calculates reliability that indicates a likelihood that the candidate attention area detected by the candidate attention area detection section is the attention area; and
a display mode setting section that performs a display mode setting process that sets a display mode of an output image corresponding to the reliability calculated by the reliability calculation section;
the display mode setting section including a processing section that performs a processing process on the first image based on the reliability calculated by the reliability calculation section and the first image;
the display mode setting section setting an area within the first image that corresponds to the attention area for which it has been determined that the reliability is high to be a corresponding attention area, and performing the processing process on the corresponding attention area; and
the processing section performing a blending process on the first image and the second image based on the reliability as the processing process to set the display mode of the output image;
wherein:
the processing section includes an area selection section that selects the candidate attention area detected by the candidate attention area detection section as the attention area based on the reliability, and selects a corresponding attention area within the first image that corresponds to the selected attention area; and
the processing section performs the blending process on the first image and the second image within the corresponding attention area; and
wherein:
the processing section includes an attention information setting section that sets attention information that indicates a degree of attention corresponding to the candidate attention area detected by the candidate attention area detection section, and a blending ratio setting section that sets a blending ratio of a pixel value of each pixel included in the candidate attention area within the second image and a pixel value of each pixel included in the corresponding attention area within the first image, corresponding to the degree of attention indicated by the attention information, and
the processing section performs the blending process that blends the pixel value of each pixel included in the candidate attention area within the second image with the pixel value of each pixel included in the corresponding attention area within the first image according to the blending ratio set by the blending ratio setting section.

2. The image processing device as defined in claim 1, the display mode setting section performing the display mode setting process that improves visibility of the corresponding attention area within the first image that corresponds to the attention area within the second image.

3. The image processing device as defined in claim 1, the processing section performing the processing process that improves visibility of the corresponding attention area within the first image that corresponds to the candidate attention area for which it has been determined that the reliability is high.

4. The image processing device as defined in claim 1,
the area selection section selecting the attention area as an alert area based on a priority.

5. The image processing device as defined in claim 4,
the priority being set using at least one piece of information selected from the reliability, the feature quantity of each pixel, and a degree of attention.

6. The image processing device as defined in claim 1,
the area selection section storing information about an upper limit of a number of alert areas;
the area selection section not selecting the attention area as the alert area when it is predicted that the number of alert areas exceeds the upper limit; and
the area selection section selecting the attention area as the alert area when it is not predicted that the number of alert areas exceeds the upper limit.

7. The image processing device as defined in claim 6,
the processing section including an area processing section, the area processing section storing information about a processing priority assigned to each alert area, and sequentially performing the processing process on each alert area in order from an alert area having a higher processing priority.

8. The image processing device as defined in claim 1,
the reliability calculation section calculating the reliability based on a size of the candidate attention area detected by the candidate attention area detection section.

9. The image processing device as defined in claim 1,
the reliability calculation section calculating the reliability based on the feature quantity of each pixel within the candidate attention area detected by the candidate attention area detection section.

10. The image processing device as defined in claim 1,
the candidate attention area detection section including a local area setting section that divides the second image into a plurality of local areas, and a feature quantity calculation section that calculates the feature quantity of each of the plurality of local areas using information about each pixel within each of the plurality of local areas, and
the candidate attention area detection section detecting the candidate attention area based on the feature quantity of each of the plurality of local areas calculated by the feature quantity calculation section.

11. The image processing device as defined in claim 1,
the candidate attention area detection section including a local area setting section that divides the first image into a plurality of local areas, and a feature quantity calculation section that calculates the feature quantity of each of the plurality of local areas using information about each pixel within the second image that respectively corresponds to each pixel within each of the plurality of local areas, and
the candidate attention area detection section detecting the candidate attention area based on the feature quantity of each of the plurality of local areas calculated by the feature quantity calculation section.

12. The image processing device as defined in claim 10,
the candidate attention area detection section including a classification section that compares the feature quantity of each of the plurality of local areas with a given threshold value, and classifies each of the plurality of local areas into one of a plurality of groups corresponding to comparison results, and
the candidate attention area detection section detecting an area that includes a local area among the plurality of local areas that has been classified into at least one group among the plurality of groups and a local area group adjacent thereto as the candidate attention area.

13. The image processing device as defined in claim 1,
the candidate attention area detection section including a feature quantity calculation section that calculates the feature quantity of each pixel within the second image using information about each pixel within the second image, and
the candidate attention area detection section detecting an attention pixel based on the feature quantity of each pixel calculated by the feature quantity calculation section, and detecting an area that includes at least the detected attention pixel as the candidate attention area.

14. The image processing device as defined in claim 13,
the candidate attention area including the attention pixel detected by the candidate attention area detection section and a selected non-attention pixel that is a pixel selected from non-attention pixels, the non-attention pixels being pixels that are included in the second image, and have not been detected as the attention pixel.

15. The image processing device as defined in claim 14,
the candidate attention area detection section selecting the selected non-attention pixel so that the candidate attention area that includes the attention pixel and the selected non-attention pixel forms a given figure.

16. The image processing device as defined in claim 1,
the processing section performing a luminance conversion process on an image obtained by the blending process, the luminance conversion process improving visibility of the corresponding attention area within the first image that corresponds to the candidate attention area for which it has been determined that the reliability is high.

17. The image processing device as defined in claim 1,
the processing section performing a luminance conversion process on an image obtained by the blending process in an area other than the corresponding attention area.

18. The image processing device as defined in claim 17,
the processing section performing the luminance conversion process by reducing a luminance of each pixel included in an area other than the corresponding attention area.

19. The image processing device as defined in claim 1,
the processing section performing the blending process that improves visibility of the corresponding attention area within the first image that corresponds to the candidate attention area for which it has been determined that the reliability is high.

20. The image processing device as defined in claim 1,
wherein the processor is further configured to implement:
a link section that links the first image and the second image based on first identification information that identifies the first image and second identification information that identifies the second image.

21. The image processing device as defined in claim 20,
the first image acquisition section acquiring the first image that was captured using a white light source,
the second image acquisition section acquiring the second image that was captured using a light source that emits light within the specific wavelength band,
the first identification information being information about a timing at which the first image was captured, the second identification information being information about a timing at which the second image was captured, and the link section linking the first image and the second image that were captured at close timings.

22. The image processing device as defined in claim 1, the specific wavelength band being narrower than the wavelength band of white light.

23. The image processing device as defined in claim 22, each of the first image and the second image being an in vivo image, and the specific wavelength band included in each in vivo image being a wavelength band of a light absorbed by hemoglobin in blood.

24. The image processing device as defined in claim 23, the specific wavelength band being 390 to 445 nm or 530 to 550 nm.

25. The image processing device as defined in claim 1, each of the first image and the second image being an in vivo image, and the specific wavelength band included in each in vivo image being a wavelength band of fluorescence emitted from a fluorescent substance.

26. The image processing device as defined in claim 25, the specific wavelength band being 490 to 625 nm.

27. The image processing device as defined in claim 1, each of the first image and the second image being an in vivo image, and the specific wavelength band included in each in vivo image being a wavelength band of infrared light.

28. The image processing device as defined in claim 27, the specific wavelength band being 790 to 820 nm or 905 to 970 nm.

29. The image processing device as defined in claim 1, the second image acquisition section generating the second image based on the first image acquired by the first image acquisition section.

30. The image processing device as defined in claim 29, the second image acquisition section including a signal extraction section that extracts a signal within the wavelength band of white light from the first image, and the second image acquisition section generating the second image that includes a signal within the specific wavelength band based on the signal extracted by the signal extraction section.

31. The image processing device as defined in claim 30, the second image acquisition section including a matrix data setting section that sets matrix data for calculating the signal within the specific wavelength band from the signal within the wavelength band of white light, and the second image acquisition section calculating the signal within the specific wavelength band from the signal within the wavelength band of white light using the matrix data set by the matrix data setting section to generate the second image.

32. An electronic apparatus comprising the image processing device as defined in claim 1.

33. An endoscope system comprising:

a first light source that applies white light to an in vivo object;

a second light source that applies light within a specific wavelength band to an in vivo object; and a processor comprising hardware, the processor being configured to implement:

a first image acquisition section that acquires a first in vivo image, the first in vivo image being an image that is obtained using the first light source and includes an object image including information within a wavelength band of white light;

a second image acquisition section that acquires a second in vivo image, the second in vivo image being an image that is obtained using the second light source and includes an object image including information within the specific wavelength band;

a candidate attention area detection section that detects a candidate attention area based on a feature quantity of each pixel within the second in vivo image, the candidate attention area being a candidate for an attention area;

a reliability calculation section that calculates reliability that indicates a likelihood that the candidate attention area detected by the candidate attention area detection section is the attention area;

a display mode setting section that performs a display mode setting process that sets a display mode of an output image corresponding to the reliability calculated by the reliability calculation section; and a display section that displays the output image according to the display mode set by the display mode setting section;

the display mode setting section including a processing section that performs a processing process on the first in vivo image based on the reliability calculated by the reliability calculation section and the first in vivo image;

the display mode setting section setting an area within the first in vivo image that corresponds to the attention area for which it has been determined that the reliability is high to be a corresponding attention area, and performing the processing process on the corresponding attention area; and the processing section performing a blending process on the first in vivo image and the second in vivo image based on the reliability as the processing process to set the display mode of the output image;

wherein:

the processing section includes an area selection section that selects the candidate attention area detected by the candidate attention area detection section as the attention area based on the reliability, and selects a corresponding attention area within the first in vivo image that corresponds to the selected attention area; and the processing section performs the blending process on the first in vivo image and the second in vivo image within the corresponding attention area; and wherein:

the processing section includes an attention information setting section that sets attention information that indicates a degree of attention corresponding to the candidate attention area detected by the candidate attention area detection section, and a blending ratio setting section that sets a blending ratio of a pixel value of each pixel included in the candidate attention area within the second in vivo image and a pixel value of each pixel included in the corresponding attention area within the first in vivo image, corresponding to the degree of attention indicated by the attention information, and the processing section performs the blending process that blends the pixel value of each pixel included in the candidate attention area within the second in vivo image with the pixel value of each pixel included in the corresponding attention area within the first in vivo image according to the blending ratio set by the blending ratio setting section.

34. An information storage device storing a program that causes a computer to function as:
- a first image acquisition section that acquires a first image, the first image being a color image that includes a plurality of channels, and includes an object image including information within a wavelength band of white light;
- a second image acquisition section that acquires a second image, the second image being an image that includes an object image including information within a specific wavelength band, and differs from the plurality of channels included in the first image;
- a candidate attention area detection section that detects a candidate attention area based on a feature quantity of each pixel within the second image, the candidate attention area being a candidate for an attention area;
- a reliability calculation section that calculates reliability that indicates a likelihood that the candidate attention area detected by the candidate attention area detection section is the attention area; and
- a display mode setting section that performs a display mode setting process that sets a display mode of an output image corresponding to the reliability calculated by the reliability calculation section;
- the display mode setting section including a processing section that performs a processing process on the first image based on the reliability calculated by the reliability calculation section and the first image;
- the display mode setting section setting an area within the first image that corresponds to the attention area for which it has been determined that the reliability is high to be a corresponding attention area, and performing the processing process on the corresponding attention area; and
- the processing section performing a blending process on the first image and the second image based on the reliability as the processing process to set the display mode of the output image;

wherein:
- the processing section includes an area selection section that selects the candidate attention area detected by the candidate attention area detection section as the attention area based on the reliability, and selects a corresponding attention area within the first image that corresponds to the selected attention area; and
- the processing section performs the blending process on the first image and the second image within the corresponding attention area; and wherein:
- the processing section includes an attention information setting section that sets attention information that indicates a degree of attention corresponding to the candidate attention area detected by the candidate attention area detection section, and a blending ratio setting section that sets a blending ratio of a pixel value of each pixel included in the candidate attention area within the second image and a pixel value of each pixel included in the corresponding attention area within the first image, corresponding to the degree of attention indicated by the attention information, and
- the processing section performs the blending process that blends the pixel value of each pixel included in the candidate attention area within the second image with the pixel value of each pixel included in the corresponding attention area within the first image according to the blending ratio set by the blending ratio setting section.

* * * * *